United States Patent
Lorenz et al.

[11] Patent Number: 6,069,114
[45] Date of Patent: May 30, 2000

[54] 2-AMINO-4-BICYCLOAMINO-1,3,5-TRIAZINES, THEIR PREPARATION, AND THEIR USE AS HERBICIDE AND PLANT GROWTH REGULATORS

[75] Inventors: Klaus Lorenz, Weiterstadt; Klemens Minn, Hattersheim; Lothar Willms, Hofheim; Klaus Bauer, Hanau; Hermann Bieringer, Eppstein; Christopher Rosinger, Hofheim, all of Germany

[73] Assignee: Hoechst Schering AgrEvo GmbH, Berlin, Germany

[21] Appl. No.: 08/805,576

[22] Filed: Feb. 25, 1997

[30] Foreign Application Priority Data

Feb. 28, 1996 [DE] Germany ............... 196 07 450

[51] Int. Cl.⁷ ............... A01N 43/70; C07D 403/12; C07D 405/12

[52] U.S. Cl. ............... 504/232; 544/197; 544/198; 544/113; 544/83; 544/208; 544/209; 544/204; 544/206; 544/207; 544/205; 544/183; 544/5; 544/11; 544/48; 544/49; 544/50; 544/51; 544/52; 544/55; 544/58.5; 544/62; 544/65; 544/66; 544/67; 544/68; 544/90; 544/91; 544/92; 544/95; 544/96; 544/105; 540/598; 540/481; 540/460; 540/455; 540/468; 540/469; 540/473; 540/490; 540/501; 540/502; 540/503; 540/504; 540/523; 540/569; 540/594; 504/232; 504/233; 504/234; 504/219; 504/220; 504/225; 504/228; 504/229; 504/230; 504/221; 504/223

[58] Field of Search ............... 544/208, 209, 544/204, 206, 207, 205, 197, 83, 5, 49, 52, 62, 67, 91, 96; 504/232, 233, 234; 540/598, 455, 473, 502, 523

[56] References Cited

U.S. PATENT DOCUMENTS

| | | | |
|---|---|---|---|
| 3,816,419 | 6/1974 | Cross | 260/249.9 |
| 3,932,167 | 1/1976 | Cross | 71/93 |
| 4,932,998 | 6/1990 | Takematsu | 504/230 |
| 5,290,754 | 3/1994 | Nishii | 504/232 |
| 5,403,815 | 4/1995 | Nishii | 504/230 |
| 5,527,954 | 6/1996 | Adachi | 560/227 |

FOREIGN PATENT DOCUMENTS

| | | |
|---|---|---|
| 0 283 522 | 2/1991 | European Pat. Off. . |
| 0 411 153 | 2/1991 | European Pat. Off. . |
| 0 509 544 | 10/1992 | European Pat. Off. . |
| 0 492 615 | 3/1995 | European Pat. Off. . |
| WO88/02368 | 4/1988 | WIPO . |
| WO90/09378 | 8/1990 | WIPO . |
| WO94/24086 | 10/1994 | WIPO . |
| WO 97/00254 | 1/1997 | WIPO . |

OTHER PUBLICATIONS

Chemical Abstracts, vol. 125, No. 17, Oct. 21, 1996, Abstract No. 221878, Kuboto et al., entitled "Triazine Derivatives as Active Agents in Herbicides".

*Primary Examiner*—John M. Ford
*Attorney, Agent, or Firm*—Frommer Lawrence & Haug LLP

[57] ABSTRACT

Compounds of the formula (I) and their salts

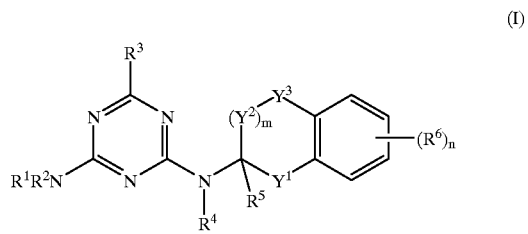

in which $R^1$ to $R^6$, $Y^1$, to $Y^2$, $Y^3$, m and n are as defined in claim 1 are suitable as herbicides and plant growth regulators. They can be prepared analogously to known processes using intermediates of the formula (V) (cf. claim 6).

7 Claims, No Drawings

2-AMINO-4-BICYCLOAMINO-1,3,5-TRIAZINES, THEIR PREPARATION, AND THEIR USE AS HERBICIDE AND PLANT GROWTH REGULATORS

The invention relates to the technical field of the herbicides and plant growth regulators, in particular the herbicides for selectively controlling broad-leaved weeds and grass weeds in crops of useful plants.

It has been disclosed that 2-amino-4-cyclohexylamino-6-perhaloalkyl-1,3,5-triazines (U.S. Pat. No. 3,816,419 and U.S. Pat. No. 3,932,167) or 2-amino-4-alkylamino-6-haloalkyl-1,3,5-triazines (WO 90/09378 (EP-A411153), WO 88102368 (EP-A-283522), WO 94/24086, EP-A-509544, EP-A492,615) have herbicidal and plant-growth-regulating properties. Frequently, the use of a large number of the known derivatives of this type are selective herbicides for controlling harmful plants or as plant growth regulators in a variety of crops of useful plants requires an outdated rate of application or leads to undesired damage of the useful plants. Surprisingly, there have now been found novel 2-amino-4-bicycloamino-1,3,5-triazines which can advantageously be employed as herbicides and plant growth regulators. For example, when employing the compounds according to the invention, the crop plants are in many cases not damaged, or damaged to a lesser extent than in the case of known active substances of a similar type.

The present invention relates to compounds of the formula (I) and salts thereof

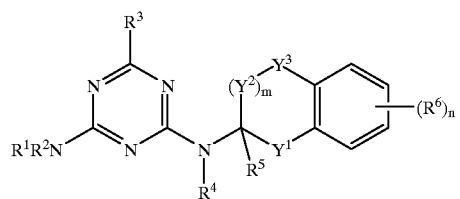

(I)

in which

R$^1$ and R$^2$ independently of one another are hydrogen, amino, alkylamino or dialkylamino having in each case 1 to 6 carbon atoms in the alkyl radical, an acyclic or cyclic hydrocarbon radical or hydrocarbon-oxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 6 ring atoms and 1 to 3 hetero ring atoms selected from the group consisting of N, O and S, each of the five last-mentioned radicals being unsubstituted or substituted, or an acyl radical, or R$^1$ and R$^2$ together with the nitrogen atom of the group NR$^1$R$^2$ are a heterocyclic radical having 3 to 6 ring atoms and 1 to 4 hetero ring atoms, the optional further hetero ring atoms, besides the nitrogen atom, being selected from the group consisting of N, O and S and the radical being unsubstituted or substituted, R$^3$ is halogen, cyano, thiocyanato, nitro or a radical of the formula —Z$^1$—R$^7$, R$^4$ is hydrogen, amino, alkylamino or dialkylamino having in each case 1 to 6 carbon atoms in the alkyl radical, an acyclic or cyclic hydrocarbon radical or hydrocarbon-oxy radical having in each case 1 to 10 carbon atoms, preferably 1 to 6 carbon atoms, or a heterocyclyl radical, heterocyclyloxy radical or heterocyclylamino radical having in each case 3 to 6 ring atoms and 1 to 3 hetero ring atoms selected from the group consisting of N, O and S, each of the five last-mentioned radicals being unsubstituted or substituted, or an acyl radical, R$^5$ is halogen, cyano, thiocyanato, nitro or a radical of the formula —Z$^2$—R$^8$, R$^6$, if n=1, or the radicals R$^6$ in each case independently of one another, if n is greater than 1, is, or are, halogen, cyano, thiocyanato, nitro or a group of the formula —Z$^3$—R$^9$, R$^7$, R$^8$, R$^9$ in each case independently of one another are hydrogen or an acyclic hydrocarbon radical, for example having in each case 1 to 20 carbon atoms, preferably 1 to 10 carbon atoms, it being possible for carbon atoms in the chain to be substituted by hetero atoms selected from the group consisting of N, O and S, or a cyclic hydrocarbon radical, preferably having 3 to 8 carbon atoms, in particular 3 to 6 carbon atoms, or a heterocyclic radical, preferably having 3 to 9 ring atoms and 1 to 3 hetero ring atoms selected from the group consisting of N, O and S, each of the last-mentioned 3 radicals being unsubstituted or substituted, Z$^1$, Z$^2$, Z$^3$ in each case independently of one another are a direct bond or a divalent group of the formula —O—, —S(O)$_p$—, —S(O)$_p$—O—, —O—S(O)$_p$—, —CO—, —CS—, —S—CO—, —CO—S—, —O—CS—, —CS—O—, —S—CS—, —CS—S—, —O—CO—, —CO—O—, —NR'—, —O—NR'—, —NR'—O—, —NR'—CO— or —CO—NR'—, p being 0, 1 or 2 and R' being hydrogen, alkyl having 1 to 6 carbon atoms, phenyl, benzyl, cycloalkyl having 3 to 6 carbon atoms or alkanoyl having 1 to 6 carbon atoms, Y$^1$, Y$^2$, Y$^3$ and further groups Y$^2$, if m is 2, 3 or 4 are in each case independently of one another a divalent group of the formula CR$^a$R$^b$, R$^a$ and R$^b$ being identical or different and in each case a radical selected from the group consisting of the radicals which are possible for R$^7$ to R$^9$, or a divalent group of the formula —O—, —CO—, CS, —CH(OR*)—, —C(=NR*)—, S(O)$_q$—, —NR*— or —N(O)—, q being 0, 1 or 2 and R* being hydrogen or alkyl having 1 to 4 carbon atoms, or Y$^1$ or Y$^3$ are a direct bond, two oxygen atoms of the groups Y$^2$ and Y$^3$ not being adjacent, m is 1, 2, 3 or 4, in particular 1 or 2, n is 0, 1, 2, 3 or 4, in particular 0, 1 or 2.

By adding a suitable inorganic or organic acid such as HCl, HBr, H$_2$SO$_4$ or HNO$_3$, but also oxalic acid or sulfonic acids, onto a basic group, for example amino or alkylamino, the compounds of the formula (I) can form salts. Suitable substituents which can exist in deprotonated form, for example sulfonic acids or carboxylic acids, can form internal salts with groups which can be protonated themselves, for example amino groups. Equally, salts can be formed by replacing the hydrogen in suitable substituents, for example sulfonic acids or carboxylic acids, by a cation which is suitable for agriculture. Examples of these salts are metal salts, in particular alkali metal salts or alkaline earth metal salts, in particular sodium and potassium salts, or else ammonium salts, or salts with organic amines.

In formula (I) and all subsequent formulae, the radicals alkyl, alkoxy, haloalkyl, haloalkoxy, alkylamino and alkylthio and the corresponding unsaturated and/or substituted radicals can be in each case straight-chain or branched in the carbon skeleton. Unless specifically indicated, the lower carbon skeletons, for example those having 1 to 6 carbon atoms or, in the case of unsaturated groups, 2 to 6 carbon atoms, are preferred for these radicals.

Alkyl radicals, also in the composite meanings such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meanings of the unsaturated radicals which are possible and which correspond to the alkyl radicals.

Alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Alkenyl in the form of $(C_3–C_4)$alkenyl is preferably an alkenyl radical having 3 or 4 carbon atoms in which the multiple bond is not positioned between C-1 and C-2, C-1 denoting the carbon atom with the position of "yl". The same applies analogously to $(C_3–C_4)$alkynyl.

Cycloalkyl is a carbocyclic saturated ring system having preferably 3–8 carbon atoms, for example cyclopropyl, cyclopentyl or cyclohexyl.

Halogen is, for example, fluorine, chlorine, bromine or iodine. Haloalkyl, -alkenyl and -alkynyl is alkyl, alkenyl or alkynyl which is partially or fully substituted by halogen, preferably by fluorine, chlorine and/or bromine, in particular by fluorine or chlorine, for example monohaloalkyl (=monohalogenoalkyl), perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, OCF3, $OCHF_2$, $OCH_2F$, $CF_3CF_2O$, $OCH_2CF_3$ and $OCH_2CH_2Cl$; the same applies analogously to haloalkenyl and other halogen-substituted radicals.

A hydrocarbon radical is a straight-chain, branched or cyclic saturated or unsaturated aliphatic or aromatic hydrocarbon radical, for example alkyl, alkenyl, alkynyl, cycloalkyl, cycloalkenyl or aryl; aryl is, in this context, a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms, or phenyl; the same applies analogously to a hydrocarbon radical in a hydrocarbon-oxy radical.

A cycle is a carbocyclic or heterocyclic radical which is saturated or unsaturated, the term "unsaturated" also including partially unsaturated and aromatic cycles.

Accordingly, a heterocyclic radical or ring (heterocyclyl) can be saturated or unsaturated or, especially, heteroaromatic; it preferably contains one or more hetero units in the ring, i.e. hetero atoms or ring members which also include substituted hetero atoms, preferably selected from the group consisting of N, O, S, SO, $SO_2$; it is preferably an aliphatic heterocyclyl radical having 3 to 7 ring atoms or a heteroaromatic radical having 5 or 6 ring atoms and contains 1, 2 or 3 hetero units. For example, the heterocyclic radical can be a heteroaromatic radical or ring (heteroaryl), for example a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidyl, piperidyl, piperazinyl, dioxolanyl, morpholinyl, tetrahydrofuryl.

Suitable substituents for a substituted heterocyclic radical are the substituents mentioned further below, and additionally also oxo. The oxo group can also be located on the hetero ring atoms which can exist at various oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; the term "substituted radicals", such as substituted alkyl and the like, includes, as substituents, in addition to the abovementioned saturated hydrocarbon-containing radicals corresponding unsaturated aliphatic and aromatic radicals, such as optionally substituted alkenyl, alkynyl, alkenyloxy, alkynyloxy, phenyl, phenoxy and the like. Amongst radicals having carbon atoms, those having 1 to 4 carbon atoms, in particular 1 or 2 carbon atoms are preferred. Preferred are, as a rule, substituents selected from the group consisting of halogen, for example fluorine and chlorine, $(C_1–C_4)$alkyl, preferably methyl or ethyl, $(C_1–C_4)$ haloalkyl, preferably trifluoromethyl, $(C_1–C_4)$alkoxy, preferably methoxy or ethoxy, $(C_1–C_4)$haloalkoxy, nitro and cyano. Especially preferred in this context are the substituents methyl, methoxy and chlorine.

Mono- or disubstituted amino is a chemically stable radical selected from the group consisting of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is, in this context, preferably phenyl or substituted phenyl; acyl is as defined further below, preferably $(C_1–C_4)$alkanoyl. The same applies analogously to substituted hydroxylamino or hydrazino.

Optionally substituted phenyl is preferably phenyl which is unsubstituted or mono- or polysubstituted, preferably up to trisubstituted, by identical or different radicals selected from the group consisting of halogen, $(C_1–C_4)$alkyl, $(C_1–C_4)$alkoxy, $(C_1–C_4)$haloalkyl, $(C_1–C_4)$haloalkoxy and nitro, for example o-, m- and p-tolyl, dimethylphenyls, 2-, 3- and 4-chlorophenyl, 2-, 3- and 4-trifluoro- und -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid and radicals of acids derived therefrom, such as thiocarboxylic acid, optionally N-substituted iminocarboxylic acids or the radical of carboxylic monoesters, or of optionally N-substituted carbamic acid, of sulfonic acids, sulfinic acids, phosphonic acids and phosphinic acids. Acyl is, for example, formyl, alkylcarbonyl such as $[(C_1–C_4)$alkyl]-carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. In this context, the radicals can in each case be substituted even further in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned further above in general terms for substituted phenyl.

The invention also relates to all stereoisomers which are embraced by formula (I) and to their mixtures. Such compounds of the formula (I) contain one or more asymmetric carbon atoms or else double bonds which are not separately indicated in formula (I). The stereoisomers which are possible and which are defined by their specific spatial form, such as enantiomers, diastereomers and Z and E isomers, are all embraced by formula (I) and can be obtained from mixtures of the stereoisomers by customary methods, or else prepared by stereoselective reactions in combination with the use of stereochemically pure starting materials. Formula (I) also embraces more or less stable tautomers formed by the shift of one or more double bonds in the triazine ring to the amino substituents, resulting in the formation of imine-type structures if the amino substituent in question, in the formula (I), has contained an N—H bond ($R^1$, $R^2$ and/or $R^4$=H). Examples are the tautomeric structures of the formula (I*) and (I**) of the formula (I) where $R^1$=H and $R^4$=H.

phenyl which is unsubstituted or substituted by one or more radicals selected from the group consisting of halogen, cyano, thiocyanato, nitro and radicals of the formula —$Z^5$—$R^{11}$, or a heterocyclic radical having 3 to 9 ring atoms and 1 to 3 hetero ring atoms selected from the group consisting of N, O and S, the radical being unsubstituted or substituted by one or more radicals selected from the group consisting of halogen, cyano, thiocyanato, nitro and radicals of the formula —$Z^6R^{12}$, $Z^1$, $Z^2$, $Z^3$, $Z^4$, $Z^5$, $Z^6$ in each case independently of one another are a direct bond or a divalent group of the formula —O—, —S(O)$_p$—, —S(O)$_p$—O—, —O—S(O)$_p$—, —CO—, —CS—, —S—CO—, —CO—S—, —O—CO—, —CO—O—, —NR'—, —O—NR'—, —NR'—O—, —NR'—CO— or —CO—NR'—, p being 0, 1 or 2 and R' being hydrogen, alkyl having 1 to 6 carbon atoms, phenyl, benzyl, cycloalkyl having 3 to 6 carbon atoms or alkanoyl having 1 to 6 carbon atoms, preferably a divalent group of the formula —O—, —S—, SO—, SO$_2$—, —CO—, —O—CO—, —CO—O—, —NR'—, NR'—CO— or —CO—NR'—, R' being hydrogen, alkyl having 1 to 4 carbon atoms or alkanoyl having 1 to 4 carbon atoms, in particular —O—, —CO—, —O—CO—, —CO—O—, —NR'—, NR'—CO— or

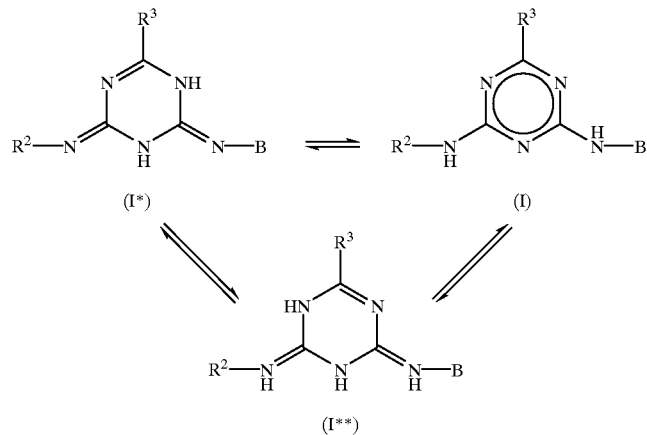

(Bicyclic structure B as in formula (I))

Compounds of the abovementioned formula (I) according to the invention or salts thereof which are of particular interest, mainly because of more potent herbicidal activity, better selectivity and/or because they can be prepared more easily are those in which $R^7$, $R^8$, $R^9$ in each case independently of one another are hydrogen or
($C_1$–$C_6$)alkyl, ($C_2$–$C_6$)alkenyl, ($C_2$–$C_6$)alkynyl, each of the last-mentioned 3 radicals being unsubstituted or substituted by one or more radicals selected from the group consisting of halogen, cyano, thiocyanato, nitro and radicals of the formula —$Z^4$—$R^{10}$, or
($C_3$–$C_8$)cycloalkyl which is unsubstituted or substituted by one or more radicals selected from the group consisting of halogen, ($C_1$–$C_6$)alkyl, ($C_1$–$C_6$)haloalkyl, ($C_1$–$C_6$)haloalkoxy, ($C_1$–$C_6$)alkoxy, ($C_1$–$C_6$)alkylthio, ($C_2$–$C_6$)alkenyl, ($C_2$–$C_6$)alkynyl, ($C_3$–$C_4$)alkenyloxy and ($C_3$–$C_4$)alkynyloxy, or —CO—NR'—, R' being hydrogen or alkyl having 1 to 4 carbon atoms, and $R^{10}$, $R^{11}$, $R^{12}$ in each case independently of one another are hydrogen, ($C_1$–$C_6$)alkyl, ($C_2$–$C_6$)alkenyl, ($C_2$–$C_6$)alkynyl, each of the last-mentioned 3 radicals being unsubstituted or substituted by one or more radicals selected from the group consisting of halogen, ($C_1$–$C_4$)alkoxy and ($C_1$–$C_4$)alkylthio, or are ($C_3$–$C_8$)cycloalkyl, phenyl, heterocyclyl having 3 to 9 ring atoms and 1 to 3 hetero ring atoms selected from the group consisting of N, O and S, each of the last-mentioned 3 cyclic radicals being unsubstituted or substituted, preferably unsubstituted or substituted by one or more radicals selected from the group consisting of halogen, cyano, thiocyanato, nitro, ($C_1$–$C_6$)alkyl, ($C_1$–$C_6$)haloalkyl, ($C_1$–$C_6$)haloalkoxy, ($C_1$–$C_6$)alkoxy, ($C_1$–$C_6$)alkylthio, ($C_2$–$C_6$)alkenyl, ($C_2$–$C_6$)alkynyl, ($C_3$–$C_4$)alkenyloxy, ($C_3$–$C_4$)alkynyloxy, ($C_1$–$C_6$)alkanoyl, ($C_1$–$C_6$)alkoxycarbonyl, mono- and di[($C_1$–$C_6$)]amino, or in each case two radicals —$Z^4$—$R^{10}$ or —$Z^5$—$R^{11}$ or —$Z^6$—$R^{12}$ together with the linkage element or the respective linkage elements are a cycle having 3 to 8 ring atoms which is carbocyclic or contains hetero ring atoms selected from the group consisting of O, S and N and which is unsubstituted or substituted by one or more radicals selected from the group consisting of halogen, ($C_1$–$C_4$)alkyl and oxo.

Also of special interest are compounds of the formula (I) according to the invention or salts thereof in which $R^1$ and $R^2$ in each case independently of one another are hydrogen, amino, alkylamino or dialkylamino having in each case 1 to 6 carbon atoms in the alkyl radical or an acyclic or cyclic hydrocarbon radical or hydrocarbon-oxy radical having in each case 1 to 6 carbon atoms or a heterocyclyl radical, heterocyclyloxy radical or heterocyclylamino radical having in each case 3 to 9 ring atoms, preferably 3 to 6 ring atoms, and 1 to 3 hetero ring atoms selected from the group consisting of N, O and S, each of the five last-mentioned radicals being unsubstituted or substituted by one or more radicals selected from the group consisting of halogen, ($C_1$–$C_4$)alkoxy, ($C_1$–$C_4$)haloalkoxy, ($C_1$–$C_4$)alkylthio, ($C_2$–$C_4$)alkenyl, ($C_2$–$C_4$)alkynyl, ($C_2$–$C_4$)alkenyloxy, ($C_2$–$C_4$)alkynyloxy, hydroxyl, amino, acylamino, mono- and dialkylamino, nitro, carboxyl, cyano, azido, [($C_1$–$C_4$)alkoxy]carbonyl, [($C_1$–$C_4$)alkyl]carbonyl, formyl, carbamoyl, mono- and di[($C_1$–$C_4$)alkyl]aminocarbonyl, phenylcarbonyl, phenoxycarbonyl, ($C_1$–$C_4$)alkylsulfinyl, ($C_1$–$C_4$)haloalkylsulfinyl, ($C_1$–$C_4$)alkylsulfonyl, ($C_1$–$C_4$)haloalkylsulfonyl and, in the case of cyclic radicals, also ($C_1$–$C_4$)alkyl and ($C_1$–$C_4$)haloalkyl or substituted by an unsubstituted or substituted radical selected from the group consisting of phenyl, phenoxy, cycloalkyl, heterocyclyl and heterocyclyloxy, or an acyl radical or $R^1$ and $R^2$ together with the nitrogen atom of the group $NR^1R^2$ are a heterocyclic radical having 3 to 6 ring atoms and 1 to 2 hetero ring atoms, the optional further hetero ring atom, besides the nitrogen atom, being selected from the group consisting of N, O and S and the radical being unsubstituted or substituted by one or more radicals selected from the group consisting of halogen, ($C_1$–$C_4$)alkyl and oxo.

$R^1$ and $R^2$ are preferably hydrogen, amino, alkylamino or dialkylamino having in each case 1 to 2 carbon atoms in the alkyl radical or ($C_1$–$C_6$)alkyl, ($C_2$–$C_6$)alkenyl, ($C_2$–$C_6$)alkynyl, each of the last-mentioned 3 radicals being unsubstituted or substituted by one or more radicals selected from the group consisting of halogen, cyano, thiocyanato, nitro, ($C_1$–$C_4$)alkoxy, ($C_1$–$C_4$)alkylthio, ($C_1$–$C_4$)haloalkyl, ($C_1$–$C_4$)haloalkoxy, mono- and di[($C_1$–$C_4$)alkyl]amino, ($C_3$–$C_9$)cycloalkyl, heterocyclyl having 3 to 9 ring atoms, phenyl, phenoxy, each of the last-mentioned 4 radicals being unsubstituted or substituted, or ($C_3$–$C_8$)cycloalkyl which is unsubstituted or substituted by one or more radicals selected from the group consisting of halogen, ($C_1$–$C_4$)alkyl, ($C_1$–$C_4$)haloalkyl, ($C_1$–$C_4$)haloalkoxy, ($C_1$–$C_4$)alkoxy and ($C_1$–$C_4$)alkylthio, or phenyl which is unsubstituted or substituted by one or more radicals, or a heterocyclic radical having 3 to 9 ring atoms and 1 to 3 hetero ring atoms selected from the group consisting of N, O and S, the radical being unsubstituted or substituted by one or more radicals, or an acyl radical.

Also of special interest are compounds of the formula (I) according to the invention or salts thereof in which $R^4$ is hydrogen, amino, alkylamino or dialkylamino having in each case 1 to 6 carbon atoms in the alkyl radical, or an acyclic or cyclic hydrocarbon radical or hydrocarbon-oxy radical having in each case 1 to 6 carbon atoms or a heterocyclyl radical, heterocyclyloxy radical or heterocyclylamino radical having in each case 3 to 6 ring atoms and 1 to 3 hetero ring atoms selected from the group consisting of N, O and S, each of the five last-mentioned radicals being unsubstituted or substituted by one or more radicals selected from the group consisting of halogen, ($C_1$–$C_4$)alkoxy, ($C_1$–$C_4$)haloalkoxy, ($C_1$–$C_4$)alkylthio, ($C_2$–$C_4$)alkenyl, ($C_2$–$C_4$)alkynyl, ($C_2$–$C_4$)alkenyloxy, ($C_2$–$C_4$)alkynyloxy, hydroxyl, amino, acylamino, mono- and dialkylamino, nitro, carboxyl, cyano, azido, [($C_1$–$C_4$)alkoxy]carbonyl, [($C_1$–$C_4$)alkyl]carbonyl, formyl, carbamoyl, mono- and di[($C_1$–$C_4$)alkyl]aminocarbonyl, ($C_1$–$C_4$)alkylsulfinyl, ($C_1$–$C_4$)haloalkylsulfinyl, ($C_1$–$C_4$)alkylsulfonyl, ($C_1$–$C_4$)haloalkylsulfonyl and, in the case of cyclic radicals, also ($C_1$–$C_4$)alkyl and ($C_1$–$C_4$)haloalkyl or substituted by an unsubstituted or substituted radical selected from the group consisting of phenyl, phenoxy, cycloalkyl, heterocyclyl and heterocyclyloxy, or an acyl radical.

For example, compounds of the formula (I) according to the invention or salts thereof are compounds in which $R^1$ $R^2$ independently of one another are hydrogen, amino, formyl, aminocarbonyl, ($C_1$–$C_4$)alkyl, cyano-($C_1$–$C_4$)alkyl, ($C_1$–$C_4$)alkylamino, di[($C_1$–$C_4$)alkyl]amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkenyl, ($C_2$–$C_6$)haloalkenyl, ($C_2$–$C_6$)alkynyl, ($C_2$–$C_6$)haloalkynyl, ($C_1$–$C_4$)alkylamino-($C_1$–$C_4$)alkyl, di[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl having 3 to 9 ring members, the cyclic groups in the last-mentioned 3 radicals being unsubstituted or substituted by one or more radicals, preferably up to three radicals, selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, mono- or di[($C_1$–$C_4$)alkyl]aminocarbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, heterocyclyl in the radicals containing in each case 3 to 9 ring atoms and 1 to 3 hetero ring atoms selected from the group consisting of N, O and S, or $R^1$ and $R^2$ together with the nitrogen atom of the group $NR^1R^2$ is a heterocyclic radical having 3 to 6 ring atoms and 1 to 2 hetero ring atoms, the optional further hetero ring atom, besides the nitrogen atom, being selected from the group consisting of N, O and S and the radical being unsubstituted or substituted by one or more radicals selected from the group consisting of halogen, $(C_1-C_4)$alkyl and oxo, $R^3$ is hydrogen, hydroxyl, amino, carboxyl, cyano, thiocyanato, formyl, aminocarbonyl, $(C_1-C_8)$alkyl, cyano-$C_1-C_4$)alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]-amino-$(C_1-C_4)$alkyl, $(C_3-C_9)$cycloalkylamino-$(C_1-C_4)$alkyl, $(C_3-C_9)$cycloalkyl, $(C_3-C_9)$cycloalkyl-$(C_1-C_4)$alkyl, heterocyclyl-$(C_1-C_4)$alkyl having 3 to 9 ring members, the cyclic groups in the last-mentioned 4 radicals being unsubstituted or substituted by one or more radicals, preferably up to three radicals, selected from the group consisting of $(C_1-C_4)$alkyl, halogen and cyano, or phenyl, phenylcarbonyl, phenoxycarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, mono- or di[$(C_1-C_4)$alkyl]aminocarbonyl, phenoxy-$(C_1-C_4)$alkyl, phenyl-$(C_1-C_4)$alkyl, heterocyclyl, heterocyclylamino, heterocyclyloxy, heterocyclylthio or one of the last-mentioned 17 radicals which is substituted in the acyclic moiety or, preferably, in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and $(C_1-C_4)$alkoxy, heterocyclyl in the radicals containing in each case 3 to 9 ring atoms and 1 to 3 hetero ring atoms selected from the group consisting of N, O and S, $R^4$ is hydrogen, amino, formyl, aminocarbonyl, $(C_1-C_4)$alkyl, cyano-$(C_1-C_4)$alkyl, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last-mentioned 3 radicals being unsubstituted or substituted by one or more radicals, preferably up to three radicals, selected from the group consisting of $(C_1-C_4)$alkyl, halogen and cyano, or phenyl, phenoxy, phenylcarbonyl, phenoxycarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, mono- or di[$(C_1-C_4)$alkyl]aminocarbonyl, phenoxy-$(C_1-C_4)$alkyl, phenyl-$(C_1-C_4)$alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals containing in each case 3 to 9 ring atoms and 1 to 3 hetero ring atoms selected from the group consisting of N, O and S, $R^5$ is hydrogen, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy$(C_1-C_4)$alkyl, $(C_1-C_4)$alkoxy-$(C_1-C_4)$alkyl, halo$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last-mentioned 3 radicals being unsubstituted or substituted by one or more radicals, preferably up to three radicals, selected from the group consisting of $(C_1-C_4)$alkyl, halogen and cyano, or phenyl, phenoxy, phenylcarbonyl, phenoxycarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, mono- or di[$(C_1-C_4)$alkyl]aminocarbonyl, phenoxy$(C_1-C_4)$alkyl, phenyl$(C_1-C_4)$alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and $(C_1-C_4)$alkoxy, heterocyclyl in the radicals containing in each case 3 to 9 ring atoms and 1 to 3 hetero ring atoms selected from the group consisting of N, O and S, $R^6$, if n is 1, and the radicals $R^6$, in each case independently of one another, when n is greater than 1, is, or are, halogen, hydroxyl, amino, nitro, formyl, carboxyl, cyano, thiocyanato, aminocarbonyl, $(C_1-C_4)$alkyl, cyano$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy$(C_1-C_4)$alkyl, $(C_1-C_4)$alkoxy-$(C_1-C_4)$alkyl, halo$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last-mentioned 3 radicals being unsubstituted or substituted by one or more radicals, preferably up to three radicals, selected from the group consisting of $(C_1-C_4)$alkyl, halogen and cyano, or phenyl, phenoxy, phenylcarbonyl, phenoxycarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, di[$(C_1-C_4)$alkyl]aminocarbonyl, phenoxy$(C_1-C_4)$alkyl, phenyl-$(C_1-C_4)$alkyl, heterocyclyl, heterocyclylamino, heterocyclyloxy, heterocyclylthio or one of the last-mentioned 17 radicals which is substituted in the acyclic moiety or, preferably, in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$ haloalkoxy, formyl, $(C_1-C_4)$alkylcarbonyl, $(C_1-C_4)$ alkoxycarbonyl and $(C_1-C_4)$alkoxy, heterocyclyl in the radicals having in each case 3 to 9 ring atoms and 1 to 3 hetero ring atoms selected from the group consisting of N, O and S or two adjacent radicals $R^9$ together being a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$ alkyl and oxo, $Y^1, Y^2$ and $Y^3$ and further groups $Y^2$ if m is 2, 3 or 4 in each case independently of one another are a divalent group of the formula $CR^aR^b$, $R^a$ and $R^b$ being identical or different and being in each case a radical as defined further below, or a divalent group of the formula —O—, —S—, —SO—, $SO_2$, —CO—, —CS—, —CH(OR*)—, —C(=NR*)—, —NR*— or —N(O)—, R being hydrogen or alkyl having 1 to 4 carbon atoms, or $Y^1$ or $Y^3$ are a direct bond, two oxygen atoms of the groups yl to $Y^3$ not being adjacent, $R^a$, $R^b$ are hydrogen, formyl, carboxyl, cyano, thiocyanato, aminocarbonyl, $(C_1-C_4)$alkyl, cyano $(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy $(C_1-C_4)$alkyl, $(C_1-C_4)$alkoxy-$(C_1-C_4)$alkyl, halo $(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$ alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl] amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last-mentioned 3 radicals being unsubstituted or substituted by one or more, preferably up to three, radicals selected from the group consisting of $(C_1-C_4)$alkyl, halogen and cyano, or phenyl, phenoxy, phenylcarbonyl, phenoxycarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$ alkylcarbonyl, $(C_1-C_4)$alkoxycarbonyl, mono- or di[$(C_1-C_4)$alkyl]aminocarbonyl, phenoxy-$(C_1-C_4)$ alkyl, phenyl-$(C_1-C_4)$alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, $(C_1-C_4)$ alkyl, $(C_1-C_4)$alkoxy, $(C_1-C_4)$alkylthio, $(C_1-C_4)$ haloalkyl, $(C_1-C_4)$haloalkoxy, formyl, $(C_1-C_4)$ alkylcarbonyl, $(C_1-C_4)$alkoxycarbonyl and $(C_1-C_4)$ alkoxy, heterocyclyl in the radicals containing in each case 3 to 9 ring atoms and 1 to 3 hetero ring atoms selected from the group consisting of N, O and S, m is 0, 1, 2, 3 or 4, in particular 1 or 2, and n is 0, 1, 2, 3 or 4, in particular 0, 1 or 2.

Preferred compounds of the formula (I) according to the invention and salts thereof are those in which $R^1, R^2$ independently of one another are hydrogen, amino, formyl, $(C_1-C_4)$alkyl, $(C_1-C_4)$alkylcarbonyl, $(C_1-C_4)$ alkoxycarbonyl or aminocarbonyl or $R^1$ and $R^2$ together with the nitrogen atom of the group $NR^1R^2$ are a heterocyclic radical having 3 to 6 ring atoms and 1 to 2 hetero ring atoms, the optional further hetero ring atom, besides the nitrogen atom, being selected from the group consisting of N, O and S and the radical being unsubstituted or substituted by one or more radicals selected from the group consisting of halogen, $(C_1-C_4)$alkyl and oxo, $R^3$ is hydrogen, carboxyl, cyano, $(C_1-C_8)$alkyl, cyano $(C_1-C_4)$alkyl, halo-$(C_1-C_4)$alkyl, hydroxy$(C_1-C_4)$ alkyl, $(C_1-C_4)$alkoxy-$(C_1-C_4)$alkyl, halo-$(C_1-C_4)$ alkoxy-$(C_1-C_4)$alkyl, $(C_2-C_6)$alkenyl, halo-$(C_2-C_6)$ alkenyl, $(C_1-C_4)$alkylamino-$(C_1-C_4)$alkyl, di[$(C_1-C_4)$ alkyl]amino-$(C_1-C_4)$alkyl, $(C_3-C_9)$cycloalkylamino-$(C_1-C_4)$alkyl, $(C_3-C_9)$cycloalkyl, $(C_3-C_9)$cycloalkyl-$(C_1-C_4)$alkyl, heterocyclyl-$(C_1-C_4)$alkyl having 3 to 9 ring members, the cyclic groups being unsubstituted in the last-mentioned 4 radicals or substituted by one or more radicals, preferably up to three radicals, selected from the group consisting of $(C_1-C_4)$alkyl and halogen, or phenyl, phenylcarbonyl, phenyl-carbonyl-$(C_1-C_4)$ alkyl, $(C_1-C_4)$alkoxycarbonyl-$(C_1-C_4)$alkyl, $(C_1-C_4)$ alkylaminocarbonyl-$(C_1-C_4)$alkyl, $(C_1-C_4)$ alkylcarbonyl, $(C_1-C_4)$alkoxycarbonyl, phenoxy-$(C_1-C_4)$alkyl, phenyl-$(C_1-C_4)$alkyl, heterocyclyl, or one of the last-mentioned 10 radicals which is substituted in the acyclic moiety or, preferably, in the cyclic moiety by one or more radicals selected from the group consisting of halogen, nitro, $(C_1-C_4)$alkyl, $(C_1-C_4)$ alkoxy, $(C_1-C_4)$haloalkyl, $(C_1-C_4)$alkylcarbonyl, $(C_1-C_4)$alkoxycarbonyl and $(C_1-C_4)$alkoxy, heterocyclyl in the radicals containing in each case 3 to 7 ring atoms and 1 to 3 hetero ring atoms selected from the group consisting of N, O and S, $R^4$ is hydrogen, amino, formyl, aminocarbonyl, $(C_1-C_4)$ alkyl, cyano-$(C_1-C_4)$alkyl, $(C_1-C_4)$alkylamino, $(C_1-C_4)$alkoxy-$(C_1-C_4)$alkyl, $(C_2-C_6)$alkenyl, halo-$(C_2-C_6)$alkenyl, $(C_2-C_6)$alkynyl, phenyl, $(C_1-C_4)$ alkylcarbonyl, $(C_1-C_4)$alkoxycarbonyl, phenoxy-$(C_1-C_4)$alkyl, phenyl-$(C_1-C_4)$alkyl, or one of the last-mentioned 5 radicals which is substituted in the acyclic moiety or, preferably, in the cyclic moiety by one or more radicals selected from the group consisting of halogen, $(C_1-C_4)$alkyl and $(C_1-C_4)$alkoxy, $R^5$ is hydrogen, $(C_1-C_4)$alkyl, $(C_2-C_6)$alkenyl or $(C_2-C_6)$ alkynyl, $R^6$, if n is 1, and the radicals $R^6$ in each case independently of one another, if n is greater than 1, is, or are, halogen, hydroxyl, amino, nitro, formyl, carboxyl, cyano, $(C_1-C_4)$alkyl, cyano$(C_1-C_4)$alkyl, $(C_1-C_4)$ alkoxy, $(C_1-C_4)$alkylamino, halo-$(C_1-C_4)$alkyl, hydroxy-$(C_1-C_4)$alkyl, $(C_1-C_4)$alkoxy-$(C_1-C_4)$akyl, $(C_2-C_6)$alkenyl, $(C_2-C_6)$alkynyl, $(C_1-C_4)$alkylamino-$(C_1-C_4)$alkyl or phenyl, phenoxy, phenylcarbonyl or one of the last-mentioned 3 radicals which is substituted by one or more radicals selected from the group consisting of halogen, $(C_1-C_4)$alkyl and $(C_1-C_4)$ alkoxy, $Y^1$ is a direct bond or $CH_2$, $(Y^2)_m$ is a divalent radical of the formula —$CH_2$—, —$CH(CH_3)$—, —$C(CH_3)_2$—, —$CH_2CH_2$—, —CH $(CH_3)$—$CH_2$—, —$CH(CH_3)$—$CH(CH_3)$—, —$CH_2CH$ $(CH_3)$—, —$CH(C_6H_5)$—$CH_2$—, —$CH_2CH(C_6H_5)$— or —$CH(CH_3)$—$CH(C_6H_5)$—, $Y^3$ is a direct bond or a divalent radical of the formula $CH_2$, —$CH(CH_3)$—, —$C(CH_3)_2$—, $CH(OH)$, —O—, —S—, CO, SO$_2$, NH, N(CH$_3$), N(C$_2$H$_5$), N(n-C$_3$H$_7$), N(i-C$_3$H$_7$), N(n-C$_4$H$_9$), N(i-C$_4$H$_9$), N(s-C$_4$H$_9$), N(t-C$_4$H$_9$), N(C$_6$H$_5$) preferably a direct bond, CH$_2$, —O— or —S—, and n is 0, 1, 2 or 3.

Especially preferred compounds of the formula (I) according to the invention and salts thereof are those in which R$^1$, R$^2$ independently of one another are hydrogen or (C$_1$–C$_4$)alkyl or R$^1$ and R$^2$ together with the nitrogen atom of the group NR$^1$R$^2$ are a saturated heterocyclic radical having 3 to 6 ring atoms and 1 to 2 hetero ring atoms, the optional further hetero ring atom, besides the nitrogen atom, being selected from the group consisting of N and O, R$^3$ is (C$_1$–C$_8$)alkyl, cyano(C$_1$–C$_4$)alkyl, (C$_1$–C$_4$) haloalkyl, hydroxy-(C$_1$–C$_4$)alkyl, (C$_1$–C$_4$)alkoxy-(C$_1$–C$_4$)alkyl, halo(C$_1$–C$_4$)alkoxy-(C$_1$–C$_4$)alkyl, (C$_2$–C$_6$)alkenyl, halo-(C$_2$–C$_6$)alkenyl, (C$_1$–C$_4$) alkylamino-(C$_1$–C$_4$)alkyl, di[(C$_1$–C$_4$)alkyl]amino-(C$_1$–C$_4$)alkyl, (C$_3$–C$_9$)cycloalkylamino-(C$_1$–C$_4$)alkyl, (C$_3$–C$_9$)cycloalkyl, (C$_3$–C$_9$)cycloalkyl-(C$_1$–C$_4$)alkyl, saturated heterocyclyl(C$_1$–C$_4$)alkyl, the cyclic groups in the last-mentioned 4 radicals being unsubstituted or substituted by one or more radicals, preferably up to three radicals, selected from the group consisting of (C$_1$–C$_4$)alkyl and halogen, or phenyl, phenylcarbonyl-(C$_1$–C$_4$)alkyl, (C$_1$–C$_4$)alkoxycarbonyl-(C$_1$–C$_4$)alkyl, (C$_1$–C$_4$)alkylaminocarbonyl-C$_1$–C$_4$)alkyl, phenoxy-(C$_1$–C$_4$)alkyl, phenyl-(C$_1$–C$_4$)alkyl, heterocyclyl, or one of the last-mentioned 7 radicals which is substituted in the acyclic moiety or, preferably, in the cyclic moiety by one or more radicals selected from the group consisting of halogen, nitro, (C$_1$–C$_4$)alkyl, (C$_1$–C$_4$) alkoxy, (C$_1$–C$_4$)haloalkyl, (C$_1$–C$_4$)alkylcarbonyl, (C$_1$–C$_4$)alkoxycarbonyl and (C$_1$–C$_4$)alkoxy, heterocyclyl in the radicals containing in each case 3 to 7 ring atoms and 1 to 3 hetero ring atoms selected from the group consisting of N, O and S, R$^4$ is hydrogen, amino, formyl, aminocarbonyl, (C$_1$–C$_4$) alkyl, cyano-(C$_1$–C$_4$)alkyl, (C$_1$–C$_4$)alkylamino, (C$_1$–C$_4$)alkoxy-(C$_1$–C$_4$)alkyl, (C$_2$–C$_6$)alkenyl, halo (C$_2$–C$_6$)alkenyl, (C$_2$–C$_6$)alkynyl, phenyl, (C$_1$–C$_4$) alkylcarbonyl, (C$_1$–C$_4$)alkoxycarbonyl, phenoxy (C$_1$–C$_4$)alkyl, phenyl-(C$_1$–C$_4$)alkyl, or one of the last-mentioned 5 radicals which is substituted in the acyclic moiety or, preferably, in the cyclic moiety by one or more radicals selected from the group consisting of halogen, (C$_1$–C$_4$)alkyl and (C$_1$–C$_4$)alkoxy, R$^5$ is hydrogen or (C$_1$–C$_4$)alkyl, R$^6$, if n is 1, and the radicals R$^6$ in each case independently of one another, if n is greater than 1, is, or are, halogen, (C$_1$–C$_4$)alkyl, (C$_1$–C$_4$)alkoxy or halo(C$_1$–C$_4$) alkyl, Y$^1$ is a direct bond or CH$_2$, (Y$^2$)$_m$ is a divalent radical of the formula CH$_2$ or CH$_2$CH$_2$, preferably CH$_2$CH$_2$, Y$^3$ is a direct bond, CH$_2$, —O— or —S—, preferably CH$_2$, and n is 0, 1, 2 or 3.

The present invention also relates to a process for the preparation of the compounds of the formula (I) or salts thereof, which comprises a) reacting a compound of the formula (II)

R$^3$—R$^{13}$ (II)

in which R$^{13}$ is a functional group selected from the group consisting of carboxyl and carboxyl group derivatives, for example carboxylic esters, carboxylic ortho esters, carboxylic acid chloride, carboxamide, carboxylic acid anhydride, trichloromethylketo and trichloromethyl with a biguanidide of the formula (III) or an acid addition salt thereof

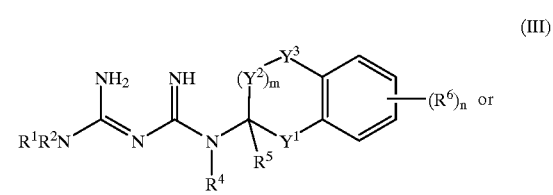

b) reacting a compound of the formula (IV)

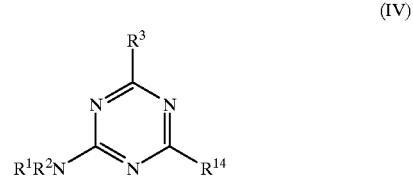

in which R$^{14}$ is an exchangeable radical or a leaving group, for example a leaving group such as chlorine, trichloromethyl, (C$_1$–C$_4$)alkylsulfonyl and unsubstituted or substituted phenyl-(C$_1$–C$_4$)alkylsulfonyl or (C$_1$–C$_4$)alkylphenylsulfonyl, with a suitable amine of the formula (V) or an acid addition salt thereof

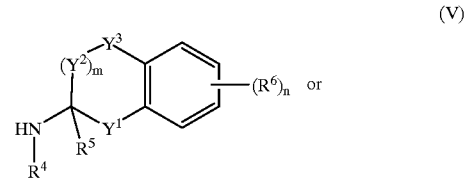

c) reacting a diamino-1,3,5-trianzine of the formula (VI)

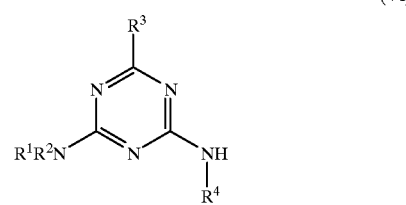

with an isocyanate of the formula (VII)

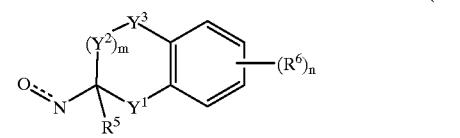

the radicals R$^1$, R$^2$, R$^3$, R$^4$, R$^5$ and R$^6$, and Y$^1$, Y$^2$, Y$^3$, m and n in formulae (II), (III), (IV), (V), (VI) and (VII) being as defined in formula (I).

The compounds of the formulae (II) and (III) are preferably reacted with base catalysis in an inert organic solvent, for example tetrahydrofuran (THF), dioxane, acetonitrile, dimethylformamide (DMF), methanol and ethanol, at temperatures between −10° C. and the boiling point of the solvent, preferably at 20° C. to 60° C.; if acid addition salts of the formula (III) are used, they are generally liberated in situ with the aid of a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-Miazabicylco[5.4.0]undec-7-ene (DBU). The base in question is employed, for example, in a range of from 0.1 to 3 mol equivalents based on the compound of the formula (III). Relative to the compound of the formula (III), the compound of the formula (II) can be employed, for example, in equimolar amounts or in an excess of up to 2 mol equivalents. The processes are known from the literature by way of analogy (compare: Comprehensive Heterocyclic Chemistry, A. R. Katritzky, C. W. Rees, Pergamon Press, Oxford, N.Y., 1984, Vol.3; Part 2B; ISBN 0-08/030703-5, p.290).

The compounds of the formulae (IV) and (V) are preferably reacted with base catalysis in an inert organic solvent, for example THF, dioxane, acetonitrile, DMF, methanol and ethanol, at temperatures between −10° C. and the boiling point of the respective solvent or solvent mixture, preferably at 20° C. to 60° C.; if the compound of the formula (V) is used in the form of the acid addition salt, it is, if appropriate, liberated in situ with the aid of a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0]undec-7-ene (DBU). The base in question is generally employed in a range of from 1 to 3 mol equivalents based on the compound of the formula (IV); relative to the compound of the formula (V), the compound of the formula (IV) can be employed, for example, in equimolar amounts or in an excess of up to 2 mol equivalents. The corresponding processes are known in principle from the literature (cf. Comprehensive Heterocyclic Chemistry, A. R. Katritzky, C. W. Rees, Pergamon Press, Oxford, N.Y., 1984, Vol.3; Part 2B; ISBN 0-08-030703-5, p. 482).

The diamino-1,3,5-triazines of the formula (VI) and isocyanates of the formula (VII) are preferably reacted with base catalysis in an inert organic solvent, for example tetrahydrofuran (THF), dioxane, acetonitrile, dimethylformamide (DMF), at temperatures between −10° C. and the boiling point of the solvent, preferably at 20° C. to 60° C. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0] undec-7-ene (DBU).

The base in question is employed, for example, in a range of from 0.5 to 3 mol equivalents based on the compound of the formula (VI). Relative to the compound of the formula (VI), the compound of the formula (VII) can be employed, for example, in equimolar amounts or in a small excess. The corresponding processes for acyclic and aromatic derivatives are known in principle from the literature (cf. B. Singh; Heterocycles, 1993, 34, p. 929–935).

The starting materials of the formulae (II), (III), (IV), (V), (VI) and (VII) are either commercially available or can be prepared by or analogously to processes known from the literature. For example, the compounds can also be prepared by one of the processes described hereinbelow.

The biguanidines of the formula (III) can be obtained, for example, by reacting cyanoguanidines of the formula

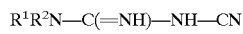

R$^1$R$^2$N—C(=NH)—NH—CN in which R$^1$ and R$^2$ are as defined in formula (I) with amines of the abovementioned formula (V), preferably in the form of the hydrohalides or other acid addition salts. To this end, it is possible, for example, to heat both reactants in an inert solvent, for example a higher-boiling, optionally chlorinated hydrocarbon such as dichlorobenzene, to 100 to 190° C., and the biguanidines, which are obtained as salts, can be isolated by filtration with suction. Similar processes are known; see, for example, L. L. Shapiro, V. A. Parrino, L. Freedmann in JACS 81 (1959) 3728 or H. M. Eisa, A. S. Tantawy and M. M. Kerdawy in Pharmazie 46 (1991) 182 et seq. If appropriate, the reactions can be catalyzed by adding metal salts such as copper(II) sulfate, zinc(II) chloride or iron(II) chloride (T. Suyama, T. Soga, K. Miauchi in NIPPON KAGAKU KAISHI (1989), (5), 884–887), in which case the reaction can be carried out in most cases at low temperatures in the range from 50° C. to the reflux point of the solvents in question. If appropriate, the reaction can be carried out in a large number of solvents such as tetrahydrofuran (THF), dioxane, alcohols or ethers.

The amines of the formula (V), which are employed for the preparation of the biguanidines of the formula (III), are also employed in process b), which is an alternative for the preparation of compounds (I) (see below).

The compound of the formula (IV), or a direct precursor thereof, can be prepared for example as follows:

1. The reaction of a compound of the formula (II) with an amidonothiourea derivative of the formula (VIII),

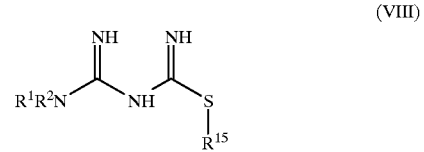

(VIII)

in which R$^{15}$ is (C$_1$–C$_4$)alkyl or phenyl-(C$_1$–C$_4$)alkyl and R$^1$ and R$^2$ are as defined in formula (I) gives compounds of the formula (IV) in which R$^{14}$ is —SR$^{15}$.

2. The reaction of a cyclic amidine of the formula (IX) or of an acid addition salt thereof

(IX)

in which R$^3$ is as defined in formula (I) with an N-cyanodithioiminocarbonate of the formula (X)

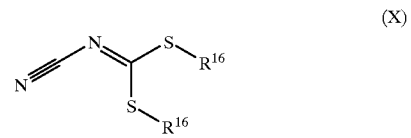

(X)

in which R$^{16}$ is (C$_1$–C$_4$)alkyl or phenyl-(C$_1$–C$_4$)alkyl gives compounds of the formula (IV) in which R$^{14}$ is —S—R$^{16}$.

3. The reaction of an alkali metal dicyanamide with a cyclic carboxylic acid derivative of the abovementioned formula (II) gives compounds of the formula (IV) in which $R^{14}$ is $NH_2$.

4. The reaction of trichloroacetonitrile with a carbonitrile of the formula (XI)

(XI)

in which $R^3$ is as defined in formula (I) first gives compounds of the formula (XII)

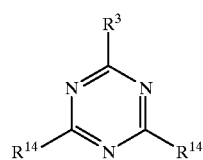
(XII)

in which $R^{14}$ is $CCl_3$, and these are subsequently reacted with compounds of the formula $HNR^1R^2$ ($R^1$ and $R^2$ as in formula (I)), to give compounds of the formula (IV), in which $R^{14}$ is $CCl_3$.

If appropriate, other intermediates of the formula (XII) which have 2 exchangeable groups $R^{14}$ may also be prepared analogously to the above processes under 1.–4. (cf. formula (IV)), and the exchangeable groups can be substituted in succession by suitable amines or ammonia to obtain compounds of the formula (IV) or the formula (I) analogously to generally known procedures. Equally, commercially available compounds or other compounds of the formula (XII) which can be prepared by other processes can be modified analogously.

If appropriate, intermediates of the formula (IV) or (XII) in which $R^{14}$ is $(C_1-C_4)$alkylthio or phenyl-$(C_1-C_4)$alkylthio and which have been obtained analogously to the above processes under 1.–4. can be converted into more reactive derivatives of the formulae (VI) or (XII) by chlorination or oxidation.

The reaction of the carboxylic acid derivatives of the formula (II) with the amidinothiourea derivatives of the formula (VIII) is preferably carried out with base catalysis in an organic solvent, for example acetone, THF, dioxane, acetonitrile, DMF, methanol or ethanol, at temperatures from −10° C. to the boiling point of the solvent, preferably at 0° C. to 20° C. Alternatively, the reaction can be carried out in water or in aqueous solvent mixtures with one or more of the abovementioned organic solvents. If (VIII) is employed in the form of an acid addition salt, it can be liberated in situ with a base, if appropriate. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0]undec-7ene (DBU). The base in question is employed in a range of from 1 to 3 mol equivalents based on the compound of the formula (VIII). Compounds of the formula (II) and (VIII) can be employed, for example, in equimolar amounts or in an excess of up to 2 mol equivalents of compound of the formula (II) (for analogous processes, compare: H. Eilingsfeld, H Scheuermann, Chem. Ber.; 1967, 100, 1874).

The reaction of the amidines of the formula (IX) with the N-cyanodithioimino-carbonates of the formula (X) is preferably carried out with base catalysis in an inert organic solvent, for example acetonitrile, DMF, dimethylacetamide (DMA), N-methylpyrrolidone (NMP), methanol and ethanol, at temperatures from −10° C. to the boiling point of the solvent, preferably at 20° C. to 80° C. If (IX) is employed in the form of an acid addition salt, it can be liberated in situ with a base, if appropriate. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0]undec-7ene (DBU). The base in question is employed in a range of from 1 to 3 mol equivalents based on the compound of the formula (X); compounds of the formula (IX) and (X) can generally be employed in equimolar amounts or in an excess of 2 mol equivalents of compound of the formula (IX) (for analogous processes, see: T. A. Riley, W. J. Henney, N. K. Dalley, B. E. Wilson, R. K. Robins; J. Heterocyclic Chem.; 1986, 23 (6), 1706–1714).

The preparation of intermediates of the formula (XII) where $R^{14}$ is chlorine can be effected by reacting alkali metal dicyanamide with a carboxylic acid derivative of the formula (II), in which case $R^{13}$ is preferably the functional group carboxylic acid chloride or carboxamide. The reaction of the reactants is carried out for example with acid catalysis in an inert organic solvent, for example toluene, chlorobenzene or chlorinated hydrocarbons, at temperatures between −10° C. and the boiling point of the solvent, preferably at 20° C. to 80° C., it being possible for the resulting intermediates to be chlorinated in situ with a suitable chlorinating reagent, such as phosphorus oxychloride. Examples of suitable acids are hydrohalic acids such as HCl or else Lewis acids, for example $AlCl_3$ or $BF_3$ (compare U.S. Pat. No. 5,095,113, DuPont).

The preparation of intermediates of the formula (XII) where $R^{14}$ is trihalomethyl can be effected by reacting the corresponding trihaloacetonitriles with a carbonitrile of the formula (XI). The reactants are reacted for example with acid catalysis in an inert organic solvent, for example toluene, chlorobenzene or chlorinated hydrocarbons, at temperatures between −40° C. and the boiling point of the solvent, preferably at −10° C. to 30° C. Examples of suitable acids are hydrohalic acids such as HCl or else Lewis acids, for example $AlCl_3$ or $BF_3$ (cf. EP-A-130939, Ciba Geigy).

Intermediates of the formulae (IV) or (XII) in which $R^{14}$ is $(C_1-C_4)$alkylmercapto or unsubstituted or substituted phenyl-$(C_1-C_4)$alkylmercapto can be converted into more reactive chlorotriazines of the formula (IV) or (XII) in which $R^{14}$ is chlorine with a suitable chlorinating reagent, for example elemental chlorine or phosphorus oxychloride in an inert organic solvent, for example toluene, chlorobenzene, chlorinated hydrocarbons or others at temperatures between −40° C. and the boiling point of the solvent, preferably at 20° C. to 80° C. (cf. J. K Chakrabarti, D. E. Tupper; Tetrahedron 1975, 31(16), 1879–1882).

Intermediates of the formulae (IV) or (XII) in which $R^{14}$ is $(C_1-C_4)$alkylmercapto or unsubstituted or substituted phenyl-$(C_1-C_4)$alkylmercapto or $(C_1-C_4)$alkylphenylthio can be oxidized with a suitable oxidant, for example m-chloroperbenzoic acid, hydrogen peroxide or potassium peroxomonosulfate, in a suitable solvent, for example chlorinated hydrocarbons, acetic acid, water, alcohols, acetones or mixtures of these, at temperatures between 0° C. and the boiling point of the solvent, preferably from 20° C. to 80° C. (cf.: T. A. Riley, W. J. Henney, N. K. Dalley, B. E. Wilson, R. K. Robins; J. Heterocyclic Chem.; 1986, 23 (6), 1706–1714).

Compounds which are analogous to those of the formula (IV) are also obtained by selective nucleophilic substitution of compounds (XII) with amines of the formula $R^1R^2NH$ or salts thereof, during which process the salt is liberated in situ. To this end, one of the exchangeable groups of the compounds of the formula (XII) in which $R^{14}$ is, for example, halogen, perhalomethyl, $(C_1-C_4)$alkylsulfinyl, $(C_1-C_4)$alkylsulfonyl or other leaving groups known from the literature, is reacted with the amine in a suitable solvent, for example THF, dioxane, alcohols, DMF or acetonitrile or mixtures of these, at temperatures between −10° C. and the boiling point of the solvent, preferably at 10° C. to 25° C., if appropriate under alkaline conditions. Bases which are suitable for this purpose are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0] undec-7-ene (DBU). The base in question is employed in a range of from 1 to 3 mol equivalents based on the compound of the formula (XII); the nucleophile is generally employed in equimolar amounts or in an excess of up to 2 mol equivalents and, if appropriate, may also be employed itself as the base (cf. analogous processes in: V.I. Kaelarev, Dibi Ammar, A. F. Lunin; Ximinya Geterosiki. Soedin., 1985, N11, 1557–1563).

Amines of the formula (V) can be prepared, for example, by hydrogenating the corresponding oximes which, in turn, can be prepared from the corresponding ketones. For example, A. B. Sen, S. B. Singh describe an analogous process in J. Ind. Chem. Soc. 43 (1966) 521, in which the reaction of sodium to sodium ethoxide is used as hydrogen source. Moreover, Sarges et al. describe a process in J. Med. Chem. 16 (1973) 1003–1008 for converting a ketone into the oxime and the palladium-catalyzed hydrogenation thereof to give a corresponding amine hydrochloride. Hydrogenations with Raney-Nickel are also known (D. Barbry, D. Couturier, N. Abdellatifi, D. Lesieur, C. Lespagnol; J. Heterocycl. Chem. 28 (1991) 449), as are hydrogenations with boron hydrides (A. K. Gosh, S. P. McKee, W. M. Sanders; Tetrahedron Lett. 32 (1991) 711–714). Furthermore, other processes are described for corresponding bicyclic derivatives which can be used for synthesizing amines of the formula (V).

The following acids are suitable for preparing the acid addition salts of the compounds of the formula (I): hydrohalic acids such as hydrochloric acid or hydrobromic acid, furthermore phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and sulfonic acids such as p-toluenesulfonic acid or 1,5-naphtalenedisulfonic acid. The acid addition compounds of the formula (I) can be obtained in a simple manner by the customary salt formation methods, for example by dissolving a compound of the formula (I) in a suitable organic solvent, for example methanol, acetone, methylene chloride or petroleum ether, and adding the acid at temperatures of from 0° to 100° C., and they can be isolated in a known manner, for example by filtration, and, if appropriate, purified by washing with an inert organic solvent.

The base addition salts of the compounds of the formula (I) are preferably prepared in inert polar solvents, for example water, methanol or acetone, at temperatures of from 0 to 100° C. Bases which are suitable for preparing the salts according to the invention are, for example, alkali metal carbonates, such as potassium carbonate, alkali metal and alkaline earth metal hydroxides, for example NaOH or KOH, alkali metal hydrides and alkaline earth metal hydrides, for example NaH, alkali metal alkoxides and alkaline earth metal alkoxides, for example sodium methoxide, potassium tert-butoxide, or ammonia or ethanolamine.

Solvents which have been termed "inert solvents" in the above process variants are to be understood as meaning in each case solvents which are inert under the prevailing reaction conditions, but which do not have to be inert under any selected reaction condition.

The compounds of the formula (I) according to the invention and the salts thereof, hereinbelow together termed compounds of the formula (I) (according to the invention) have an outstanding herbicidal activity against a broad spectrum of economically important monocotyledonous and dicotyledonous harmful plants. The active substances also act efficiently on perennial broad-leaved weeds which produce shoots from rhizomes, rootstocks or other perennial organs and which are difficult to control. In this context, it does not matter whether the substances are applied before sowing, preemergence or post-emergence.

Specifically, examples may be mentioned of some representatives of the monocotyledonous and dicotyledonous weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species. In the case of the dicotyledonous weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention also effect outstanding control of weeds which occur under the specific conditions of rice growing, such as, for example, Sagiftaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth equally stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledonous and dicotyledonous weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in areas under agricultural crops.

In addition, the substances according to the invention have outstanding growth-regulatory properties in crop plants. They engage in the plant metabolism in a regulating manner and can thus be employed for the targeted control of plant constituents and for facilitating harvesting, for example by triggering desiccation and stunted growth. Moreover, they are also suitable for the general control and inhibition of undesirable vegetative growth without destroying the plants in the process. The inhibition of vegetative growth is very important in a large number of monocotyledonous and dicotyledonous crops since it can reduce, or completely prevent, lodging.

The compounds according to the invention can be applied in the form of wettable powders, emulsifiable concentrates, sprayable solutions, dusts or granules in the customary preparations. The invention therefore also relates to herbicidal and plant-growth-regulating compositions which comprise the compounds of the formula (I). The compounds of the formula (I) can be formulated in various ways, depending on the prevailing biological and/or chemico-physical parameters. The following possibilities are suitable formulations: wettable powders (WP), water-soluble powders (SP), water-soluble concentrates, emulsifiable concentrates (EC), emulsions (EW)$_1$ such as oil-in-water and water-in-oil emulsions, sprayable solutions, suspension concentrates (SC), oil- or water-based dispersions, solutions which are miscible with oils, capsule suspensions (CS), dusts (DP), seed-ressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances, such as, for example, insecticides, acaricides, herbicides, fungicides, and also with safeners, fertilizers and/or growth regulators, for example in the form of a ready mix or a tank mix.

Wettable powders are preparations which are uniformly dispersible in water and which, besides the active substance, also comprise ionic and/or non-ionic surfactants (wetting agents, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyltaurinate, in addition to a diluent or inert substance. To prepare the wettable powders, the herbicidally active substances are ground finely, for example in customary equipment such as hammer mills, blower mills and air-jet mills, and simultaneously or subsequently mixed with the formulation auxiliaries.

Emulsifiable concentrates are prepared, for example, by dissolving the active substance in an organic solvent, for example butanol, cyclohexanone, dimethylformamide, xylene, or else higher-boiling aromatics or hydrocarbons or mixtures of the organic solvents with the addition of one or more ionic and/or non-ionic surfactants (emulsifiers). Examples of emulsifiers which can be used are: calcium salts of alkylarylsulfonic acids such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet grinding using commercially available bead mills with an optional addition of surfactants as they have already been mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants as they have already been mentioned for example above in the case of the other types of formulation.

Granules can be prepared either by spraying the active substance onto adsorptive granulated inert material or by applying active substance concentrates to the surface of carriers such as sand, kaolinites or of granulated inert material by means of binders, for example polyvinyl alcohol, sodium polyacrylate or else mineral oils. Suitable active substances can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fluidized-bed, extruder and spray granules, see, for example, the processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). The active substance concentration in wettable powders is, for example, approximately 10 to 90% by weight, the remainder to 100% by weight being composed of customary formulation components. In the case of emulsifiable concentrates, the active substance concentration may amount to approximately 1 to 90, preferably 5 to 80, % by weight. Formulations in the form of dusts comprise 1 to 30% by weight of active substance, in most cases preferably 5 to 20% by weight of active substance, and sprayable solutions comprise approximately 0.05 to 80, preferably 2 to 50, % by weight of active substance. The active substance content of water-dispersible granules depends partly on whether the active compound is in liquid or solid form and on which granulation auxiliaries, fillers and the like are being used. The active substance content of the water-dispersible granules amounts to, for example, between 1 and 95% by weight, preferably between 10 and 80% by weight.

Besides, the abovementioned formulations of active substances comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in the tank mix are, for example, known active substances as they are described, for example, in Weed Research 26, 441–445 (1986), or "The Pesticide Manual", 10th edition, The British Crop Protection Council and the Royal Soc. of Chemistry, 1994, and the literature cited therein. Examples of active substances which may be mentioned as herbicides which are known from the literature and which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, ie. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, ie. ammonium sulfamate; anilofos; asulam; atrazine; azimsulfurone (DPX-A8947); aziprotryn; barban; BAS 516 H, ie. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, ie. 2-chloro-N,N-di-2-propenylacetamide; CDEC, ie. 2-chloroallyl diethyldithiocarbamate; chlormethoxyfen; chloramben; chlorazifop-butyl, chlormesulon (ICI-A0051); chlorbromuron; chlorbufam; chlorfenac; chlorflurecolmethyl; chloridazon; chlorimuronethyl; chlomitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-1-12); cyperquat; cyprazine; cyprazole; daimuron; 2,4-DB; dalapon; desmedipham; desmetryn; di-allate; dicamba; dichlobenil; dichlorprop; diclofop and its esters, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, ie. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, ie. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S482); flumipropyn; flupoxam (KNW-739); fluorodifen; fluoroglycofen-ethyl; flupropacil (UBIC4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyidymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, ie. 6-chloro-N-(3-chloro-2-propenyl)-5-methyl-N-phenyl-3-pyridazinamine; MT 5950, ie. N-[3-chloro-4-(1-methylethyl)phenyl]-2-methylpentanamide; naproanilide; napropamide; naptalam; NC 310, d.h. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor, primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivates, for example quizalofop-ethyl; quizalofop-P-tefuryl and -ethyl; renriduron; rimsulfuron (DPX-E 9636); S 275, ie. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, ie. 2-[[7-[2-chloro-4-(trifluoromethyl)phenoxy]-2-naphthalenyl]oxy]propanoic acid and its methyl ester; sulcotrione, sulfentrazone (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, ie. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimine (SN-24085);

thifensulfuron-methyl; thiobencarb; tiocarbazil; tralkoxydim; tri-allate; triasulfuron; triazofenamide; tribenuronmethyl; triclopyr; tridiphane; trietazine; trifluralin; triflusulfuron and esters (for example methyl ester, DPX-66037); trimeturon; tsitodef; vemolate; WL 110547, ie. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are conventionally not diluted any further with inert substances prior to use.

The application rate required, of the compounds of the formula (I), varies with the external factors such as, inter alia, temperature, humidity and nature of the herbicide used. It can vary within wide limits, for example between 0.001 and 10.0 kg/ha or more of active substance, but it is preferably between 0.005 and 5 kg/ha.

A. CHEMICAL EXAMPLES

Example A1 (=Example 25 in Table 1)

2-Amino-4-(2-fluorophenyl)-6-(5,7-dimethyl-1,2,3,4-tetrahydronaphthalene-1-amino)-1,3,5-triazine a. 27.0 g (0.13 mol) of 1-amino-5,7-dimethyl-1,2,3,4-tetrahydronaphthalene-hydrochloride and 11.5 g (0.13 mol) of cyanoguanidine are homogenized and taken up in 60 ml of chlorobenzene. This mixture is heated for 150 minutes at 140–160° C.; first, a homogeneous mixture is formed, but this later separates. The mixture is cooled, 100 ml of toluene are added, and filtration with suction then gives 40.0 g (94% of theory with a purity over 90%) of 1-biguanidino-5,7-dimethyl-1,2,3,4-tetrahydronaphthalene hydrochloride of melting point 215–216° C.

b. A methoxide solution prepared with 0.96 g (0.04 mol) of sodium and 50 ml of methanol is added to 5.9 g (0.02 mol) of 1-biguanidino-5,7-dimethyl-1,2,3,4-tetrahydronaphthalene hydrochloride in 50 ml of methanol and 6 g of ground molecular sieve 3 Å. 4.4 g (0.026 mol) of ethyl 2-fluorobenzoate are subsequently added, and the mixture is stirred for 2 hours at 25° C. and then for 4 hours at 65° C. The reaction mixture is filtered, the filtrate is concentrated, and the residue is taken up in ethyl acetate. This solution is washed with water and the organic phase is separated off and dried with sodium sulfate. The desiccant is filtered off, and the ethyl acetate phase is evaporated. After separation by column chromatography over silica gel using ethyl acetate/heptane in a ratio of 7:3 as the eluent, 3.9 g (54% of theory) of 2-amino-4-(2-fluorophenyl)-6-(5,7dimethyl-1,2,3,4-tetrahydronaphthalene-1-amino)-1,3,5-triazine of melting point 85–88° C. are obtained.

Example A2 (=Example 38 in Table 1)

2-Amino-4-(2,3-dimethyl-2,3-epoxypropyl)-6-(5,7-dimethyl-1,2,3,4-tetrahydronaphthalene-1-amino)-1,3,5-triazine a. A suspension of 37.1 g (0.3 mol) of potassium tert-butoxide in 300 ml of THF is added dropwise to a mixture of 17.4 g (0.3 mol) of acetone and 36.8 g (0.3 mol) of methyl 2-chloropropionate, the mixture being cooled to 0–2° C. After the addition has ended, the mixture is allowed to come to room temperature, and stirring is continued for 60 minutes. After hydrolysis and extraction with diethyl ether, drying of the organic phase with sodium sulfate and evaporating it on a rotary evaporator, 34.2 g (75% of theory, purity approx. 95%) of methyl 2,3-epoxy-2,3-dimethylbutyrate are obtained. This product can be employed in the subsequent step without further purification.

b. A methoxide solution prepared with 0.84 g (0.035 mol) of sodium and 50 ml of methanol is added to 5.2 g (0.0175 mol) of 1-biguanidino-5,7-dimethyl-1,2,3,4-tetrahydronaphthalene hydrochloride in 50 ml of methanol and 6 g of ground molecular sieve 3 Å. 3.8 g (0.026 mol) of methyl 2,3-epoxy-2,3-dimethylbutyrate are subsequently added, and the mixture is stirred for 2 hours at 25° C. and then for 4 hours at 65° C. The reaction mixture is filtered, the filtrate is concentrated, and the residue is taken up in ethyl acetate. This solution is washed with water and the organic phase is separated off and dried with sodium sulfate. The desiccant is filtered off and the ethyl acetate phase is evaporated. After purification by column chromatography over silica gel using ethyl acetate as the eluent, 1.4 g (24% of theory) of 2-amino-4-(2,3-dimethyl-2,3-epoxypropyl)-6-(5,7-dimethyl-1,2,3,4-tetrahydronaphthalene-1-amino)-1,3,5-triazine of melting point 118–119° C. are obtained.

Example A3 (=Example 73 in Table 1)

2-Amino-4-(5,7-dimethylthiochromane-4-amino)-6-(1-methyl-1-hydroxyethyl)-1,3,5-triazine a. A suspension of 37.8 g of sodium acetate in water is added, at 50–60° C., to a suspension of 31.1 g (0.154 mol) of 5,7-dimethylthio-chroman-4-one and 18.5 g (0.261 mol) of hydroxylamine hydrochloride in 200 ml of ethanol. This mixture is subsequently refluxed for 30 minutes. After cooling, filtration with suction of the solid which has precipitated gives 22.2 g of 5,7-dimethylthiochroman-4-one oxime (66% of theory, purity approx. 95%) of melting point 170–174° C.

b. 21.0 g (0.101 mol) of 5,7-dimethylthiochroman-4-one oxime are suspended in 300 ml of ethanol, and 22.5 g (0.935 mol) of sodium are added in the course of a few hours, a little at a time. This mixture is stirred for some more time and then slightly concentrated. The residue is treated with water, this aqueous phase is then acidified with half-concentrated hydrochloric acid, and filtration with suction of the solid which has precipitated gives 11.5 g of 4-amino-5,7-dimethylthiochromane hydrochloride (47% of theory, purity approx. 95%) of melting point 275–280° C. The product can be employed in the next step without further purification.

c. 9.0 g (0.039 mol) of 4-amino-5,7-dimethylthiochromane hydrochloride and 3.4 g (0.039 mol) of cyanoguanidine are homogenized and taken up in 25 ml of chlorobenzene. This mixture is heated for 150 minutes at 140–160° C.; first, a homogeneous mixture is formed, but this later separates. After cooling and adding 30 ml of toluene, filtration with suction gives 10.9 g (84% of theory of a purity over 90%) of 4-biguanidino-5,7-dimethylthiochromane hydrochloride of melting point 210–211° C. The product can be employed in the next step without further purification.

d. 3.2 g (0.0108 mol) of 4-biguanidino-5,7-dimethylthiochromane hydrochloride and 5 g of ground molecular sieve 3 Å are added to 1.62 g (0.054 mol) of sodium hydride in 40 ml of acetonitrile. 3.8 g (0.027 mol) of ethyl 2-hydroxyisobutyrate are subsequently added, and the mixture is stirred for 2 hours at 25° C. and then for 8 hours at 65° C. The reaction mixture is hydrolyzed and filtered, and the filtrate is taken up in ethyl acetate. The organic phase is separated off and dried with sodium sulfate. The desiccant is filtered off and the ethyl acetate phase is evaporated. Purification by column chromatography over silica gel using ethyl acetate as the eluent gives 0.4 g (10% of theory) of 2-amino-(5,7-dimethylthiochromane-4-amino)-6-(1-methyl-1-hydroxyethyl)-1,3,5-triazine of melting point 231–232° C.

Example A4 (=Example 636 in Table 1)

2-Amino-4-ethyl-6-(1-indanylamino)-1,3,5-triazine a. 45 ml of an approximately 13-molar solution of ammonia in methanol is added at 10 to 15° C. to a suspension of 40.3 g (0 164 mol) of a 75% strength toluenic solution of 2,4-dichloro-6-ethyl-1,3,5-triazine in 250 ml of toluene, and the mixture is stirred for approximately 2 hours. This reaction mixture is hydrolyzed and extracted with ethyl acetate. The organic phase is dried with sodium sulfate, the desiccant is subsequently filtered off, and the ethyl acetate phase is evaporated. This gives 26.5 g (91% of theory, purity 90%) of 2-amino-4-chloro-4-thyl-1,3,5-triazine of melting point 125 to 126° C. This intermediate can be employed in the subsequent reaction without further purification.

b. 5.2 g (0.038 mol) of potassium carbonate are added to 3.0 g (0.017 mol, purity 90%) of 2-amino-4-chloro-6-ethyl-1,3,5-triazine and 2.5 g of 1-aminoindane in 30 ml of dimethylformamide, and this mixture is heated for 4 hours at 100° C. The reaction mixture is hydrolyzed and subsequently extracted with ethyl acetate. The organic phase is dried with sodium sulfate, the desiccant is subsequently filtered off, and the ethyl acetate phase is evaporated. After separation by column chromatography over silica gel using an ethyl acetatelhexane mixture in a ratio of 7:3 as the eluent, 3.2 g (70% of theory, purity 95%) of 2-amino-4-ethyl-6-(1-indanyl-amino)-1,3,5-triazine of melting point 175 to 178° C. are obtained.

The compounds described in Table 1 are obtained by or analogously to the above Examples A1 to A4. Abbreviations used in the table are given below.
Abbreviations in Table 1
No.=Example or Example Number
M.p.=Melting point in ° C., or another characteristic property of the compound in question (for example solid foam=s. foam)
Me=methyl
Et=ethyl
Pr=propyl=n-propyl
i-Pr=isopropyl
X-i-Pr=1-X-i-Pr 1-substituted isopropyl, for example F-i-Pr=1-fluoroisopropyl or $CF(CH_3)2$, the position of the radical ("yl") here being the position 1,
c-Pr=cyclopropyl
c-hexyl=cyclohexyl
1-Me-c-Pr=1-methylcyclopropyl, the position of the radical ("-yl") being the position 1.
t-Bu=tertiary butyl
Ph=phenyl
Bz=benzyl
Ac=acetyl
Numbers=1. Number preceding substituents denotes position of the substituent on the aromatic
2. Number preceding heterocycle radicals denotes position of the radical relative to the hetero atom, for example 2-pyridinyl=pyridin-2-yl
3. Number preceding substituents $R^6$ denotes position of the substituent on the aromatic to match the indication in formula (I')

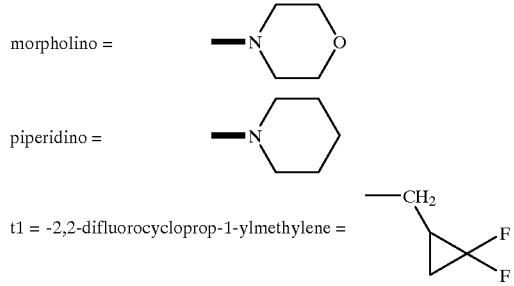

epoxy=1,2-epoxy-eth-1-yl=oxiranyl $(R^6)_n$=all substituents $R^6$; the case $(R^6)_n$=H denotes no substituents (n=0) $(Y^2)_m$=divalent group which, in the case of asymmetric substitution, such as —$CH_2$—CHPh—, is linked with the chain atom indicated on the right (here: right-hand side carbon atom) to the group $Y^3$.

TABLE 1

Compounds of the formula (I')

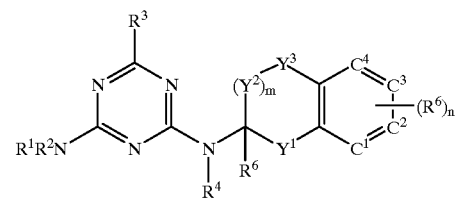

(I')

| No. | $NR^1R^2$ | $R^3$ | $R^4$ | $R^5$ | $(R^6)_n$ | $Y^1$ | $(Y^2)_m$ | $Y^3$ | Fp. (° C.) |
|---|---|---|---|---|---|---|---|---|---|
| 1 | $NH_2$ | $CF_3$ | H | H | 2-Me, 4-Me | — | —$CH_2$—$CH_2$— | —$CH_2$— | |
| 2 | $NH_2$ | $CF_2CF_2H$ | H | H | 2-Me, 4-Me | — | —$CH_2$—$CH_2$— | —$CH_2$— | 141–142 |
| 3 | $NH_2$ | F-i-Pr | H | H | 2-Me, 4-Me | — | —$CH_2$—$CH_2$— | —$CH_2$— | 128–130 |
| 4 | $NH_2$ | $CF_3$ | H | H | 2-Me, 4-Me | — | —$CH_2$—$CH_2$— | —O— | |
| 5 | $NH_2$ | $CF_2CF_2H$ | H | H | 2-Me, 4-Me | — | —$CH_2$—$CH_2$— | —O— | |

TABLE 1-continued

Compounds of the formula (I')

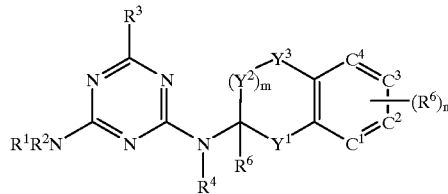

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 6 | NH$_2$ | F-i-Pr | H | H | 2-Me, 4-Me | — | —CH$_2$—CH$_2$— | —O— | |
| 7 | NH$_2$ | CF$_3$ | H | H | 2-Me, 4-Me | — | —CH$_2$—CH$_2$— | —NMe— | |
| 8 | NH$_2$ | CF$_2$CF$_2$H | H | H | 2-Me, 4-Me | — | —CH$_2$—CH$_2$— | —NMe— | |
| 9 | NH$_2$ | F-i-Pr | H | H | 2-Me, 4-Me | — | —CH$_2$—CH$_2$— | —NMe— | |
| 10 | NH$_2$ | CF$_3$ | H | H | 2-Me, 4-Me | — | —CH$_2$—CH$_2$— | —CO— | |
| 11 | NH$_2$ | CF$_2$CF$_2$H | H | H | 2-Me, 4-Me | — | —CH$_2$—CH$_2$— | —CO— | |
| 12 | NH$_2$ | F-i-Pr | H | H | 2-Me, 4-Me | — | —CH$_2$—CH$_2$— | —CO— | |
| 13 | NH$_2$ | CF$_3$ | H | H | 2-Me, 4-Me | — | —CH$_2$—CH$_2$— | —CHOH— | |
| 14 | NH$_2$ | CF$_2$CF$_2$H | H | H | 2-Me, 4-Me | — | —CH$_2$—CH$_2$— | —CHOH— | |
| 15 | NH$_2$ | F-i-Pr | H | H | 2-Me, 4-Me | — | —CH$_2$—CH$_2$— | —CHOH— | |
| 16 | NH$_2$ | CF$_3$ | H | H | 1-Me, 4-Me | — | —CH$_2$—CH$_2$— | —CH$_2$— | |
| 17 | NH$_2$ | CF$_2$CF$_2$H | H | H | 1-Me, 4-Me | — | —CH$_2$—CH$_2$— | —CH$_2$— | |
| 18 | NH$_2$ | F-i-Pr | H | H | 1-Me, 4-Me | — | —CH$_2$—CH$_2$— | —CH$_2$— | |
| 19 | NH$_2$ | CF$_3$ | H | H | 3-Me, 4-Me | — | —CH$_2$—CH$_2$— | —CH$_2$— | |
| 20 | NH$_2$ | CF$_2$CF$_2$H | H | H | 3-Me, 4-Me | — | —CH$_2$—CH$_2$— | —CH$_2$— | |
| 21 | NH$_2$ | F-i-Pr | H | H | 3-Me, 4-Me | — | —CH$_2$—CH$_2$— | —CH$_2$— | |
| 22 | NH$_2$ | CF$_3$ | H | H | 2-Et | — | —CH$_2$—CH$_2$— | —CH$_2$— | |
| 23 | NH$_2$ | CF$_2$CF$_2$H | H | H | 2-Et, 4-Me | — | —CH$_2$—CH$_2$— | —CH$_2$— | |
| 24 | NH$_2$ | F-i-Pr | H | H | 2-Et, 4-Me | — | —CH$_2$—CH$_2$— | —CH$_2$— | |
| 25 | NH$_2$ | 2-F—Ph | H | H | 2-Me, 4-Me | — | —CH$_2$—CH$_2$— | —CH$_2$— | 85–88 |
| 26 | NH$_2$ | 3-F—Ph | H | H | 2-Me, 4-Me | — | —CH$_2$—CH$_2$— | —CH$_2$— | |
| 27 | NH$_2$ | 4-F—Ph | H | H | 2-Me, 4-Me | — | —CH$_2$—CH$_2$— | —CH$_2$— | |
| 28 | NH$_2$ | 2-Me—Ph | H | H | 2-Me, 4-Me | — | —CH$_2$—CH$_2$— | —CH$_2$— | |
| 29 | NH$_2$ | 2-Et—Ph | H | H | 2-Me, 4-Me | — | —CH$_2$—CH$_2$— | —CH$_2$— | |
| 30 | NH$_2$ | 2-OH—Ph | H | H | 2-Me, 4-Me | — | —CH$_2$—CH$_2$— | —CH$_2$— | |
| 31 | NH$_2$ | 2-OMe—Ph | H | H | 2-Me, 4-Me | — | —CH$_2$—CH$_2$— | —CH$_2$— | |
| 32 | NH$_2$ | 2-CN—Ph | H | H | 2-Me, 4-Me | — | —CH$_2$—CH$_2$— | —CH$_2$— | |
| 33 | NH$_2$ | 2,4-F$_2$—Ph | H | H | 2-Me, 4-Me | — | —CH$_2$—CH$_2$— | —CH$_2$— | |
| 34 | NH$_2$ | t-Bu | H | H | 2-Me, 4-Me | — | —CH$_2$—CH$_2$— | —CH$_2$— | |
| 35 | NH$_2$ | epoxid | H | H | 2-Me, 4-Me | — | —CH$_2$—CH$_2$— | —CH$_2$— | |
| 36 | NH$_2$ | 1-Me-epoxid | H | H | 2-Me, 4-Me | — | —CH$_2$—CH$_2$— | —CH$_2$— | |
| 37 | NH$_2$ | 1-Me-2-Me-epoxid | H | H | 2-Me, 4-Me | — | —CH$_2$—CH$_2$— | —CH$_2$— | |
| 38 | NH$_2$ | 1,2,2-Me$_3$-epoxid | H | H | 2-Me, 4-Me | — | —CH$_2$—CH$_2$— | —CH$_2$— | 118–119 |
| 39 | NH$_2$ | 1-Me-2-Et-epoxid | H | H | 2-Me, 4-Me | — | —CH$_2$—CH$_2$— | —CH$_2$— | |
| 40 | NH$_2$ | 1-Me-2-n-Bu-epoxid | H | H | 2-Me, 4-Me | — | —CH$_2$—CH$_2$— | —CH$_2$— | |
| 41 | NH$_2$ | 2-Me-epoxid | H | H | 2-Me, 4-Me | — | —CH$_2$—CH$_2$— | —CH$_2$— | 91–93 |
| 42 | NH$_2$ | t1 | H | H | 2-Me, 4-Me | — | —CH$_2$—CH$_2$— | —CH$_2$— | |
| 43 | NH$_2$ | HO-i-Pr | H | H | 2-Me, 4-Me | — | —CH$_2$—CH$_2$— | —CH$_2$— | 191–193 |
| 44 | NH$_2$ | Cl-i-Pr | H | H | 2-Me, 4-Me | — | —CH$_2$—CH$_2$— | —CH$_2$— | |
| 45 | NH$_2$ | MeO-i-Pr | H | H | 2-Me, 4-Me | — | —CH$_2$—CH$_2$— | —CH$_2$— | |
| 46 | NH$_2$ | 1-HO—Et | H | H | 2-Me, 4-Me | — | —CH$_2$—CH$_2$— | —CH$_2$— | |
| 47 | NH$_2$ | 1-MeO—Et | H | H | 2-Me, 4-Me | — | —CH$_2$—CH$_2$— | —CH$_2$— | |
| 48 | NH$_2$ | 1-F—Et | H | H | 2-Me, 4-Me | — | —CH$_2$—CH$_2$— | —CH$_2$— | |
| 49 | NH$_2$ | 1-Cl—Et | H | H | 2-Me, 4-Me | — | —CH$_2$—CH$_2$— | —CH$_2$— | |
| 50 | NH$_2$ | 1-AcO—Et | H | H | 2-Me, 4-Me | — | —CH$_2$—CH$_2$— | —CH$_2$— | |
| 51 | NH$_2$ | HO-i-Pr | H | H | 1-Me, 4-Me | — | —CH$_2$—CH$_2$— | —CH$_2$— | |
| 52 | NH$_2$ | Cl-i-Pr | H | H | 3-Me, 4-Me | — | —CH$_2$—CH$_2$— | —CH$_2$— | |
| 53 | NH$_2$ | MeO-i-Pr | H | H | 2-Me, 3-Me | — | —CH$_2$—CH$_2$— | —CH$_2$— | |
| 54 | NH$_2$ | 2-Me—Bz | H | H | 2-Me, 4-Me | — | —CH$_2$—CH$_2$— | —CH$_2$— | |
| 55 | NH$_2$ | 1-Ph—Et | H | H | 2-Me, 4-Me | — | —CH$_2$—CH$_2$— | —CH$_2$— | |
| 56 | NH$_2$ | 1-Ph-c-Pr | H | H | 2-Me, 4-Me | — | —CH$_2$—CH$_2$— | —CH$_2$— | 74–75 |
| 57 | NH$_2$ | 1-Ph-c-Pr | H | H | 2-Me, 4-Me | — | —CH$_2$—CH$_2$— | —S— | |
| 58 | NH$_2$ | 1-Ph-c-Pr | H | H | 2-Me, 4-Me | — | —CH$_2$—CH$_2$— | —O— | |
| 59 | NMe2 | 1-Ph-c-Pr | H | H | 2-Me, 4-Me | — | —CH$_2$—CH$_2$— | —CH$_2$— | |
| 60 | NH$_2$ | 1-Ph-c-Pr | H | H | 3-OMe | — | —CH$_2$—CH$_2$— | —CH$_2$— | |
| 61 | NH | 1-Ph-c-Pr | H | H | 3-Me, 4-OMe | — | —CH$_2$—CH$_2$— | —CH$_2$— | |
| 62 | NH$_2$ | c-Pr | H | H | 2-Me, 4-Me | — | —CH$_2$—CH$_2$— | —CH$_2$— | |
| 63 | NH$_2$ | 1-Me-c-Pr | H | H | 2-Me, 4-Me | — | —CH$_2$—CH$_2$— | —CH$_2$— | |
| 64 | NH$_2$ | 1-HO-c-Pr | H | H | 2-Me, 4-Me | — | —CH$_2$—CH$_2$— | —CH$_2$— | |

TABLE 1-continued

Compounds of the formula (I')

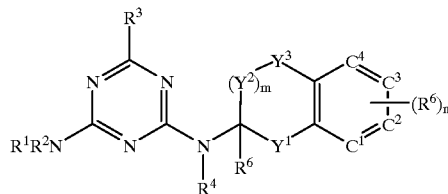

(I')

| No. | NR¹R² | R³ | R⁴ | R⁵ | (R⁶)ₙ | Y¹ | (Y²)ₘ | Y³ | Fp. (° C.) |
|---|---|---|---|---|---|---|---|---|---|
| 65 | NH₂ | 1-F-c-Pr | H | H | 2-Me, 4-Me | — | —CH₂—CH₂— | —CH₂— | |
| 66 | NH₂ | 1-Me-c-Pr | H | H | 2-Me, 4-Me | — | —CH₂—CH₂— | —S— | |
| 67 | NH₂ | 1-Me-c-Pr | H | H | 1-Me, 3-Me | — | —CH₂—CH₂— | —S— | 125–129 |
| 68 | NH₂ | 1-Me-c-Pr | H | H | 4-Me | — | —CH₂—CH₂— | —S— | |
| 69 | NH₂ | 1-Me-c-Pr | H | H | 1-Me, 4-Me | — | —CH₂—CH₂— | —S— | |
| 70 | NH₂ | 1-Me-c-Pr | H | H | 1-F, 3-F | — | —CH₂—CH₂— | —S— | |
| 71 | NH₂ | 1-F-i-Pr | H | H | 1-Me, 3-Me | — | —CH₂—CH₂— | —S— | 228–230 |
| 72 | NH₂ | 1-F-i-Pr | H | H | 1-Me, 4-Me | — | —CH₂—CH₂— | —S— | |
| 73 | NH₂ | 1-HO-i-Pr | H | H | 1-Me, 3-Me | — | —CH₂—CH₂— | —S— | 231–233 |
| 74 | NMe2 | 1-F-i-Pr | H | H | 1-Me, 3-Me | — | —CH₂—CH₂— | —S— | |
| 75 | Morpholino | 1-F-i-Pr | H | H | 1-Me, 3-Me | — | —CH₂—CH₂— | —S— | |
| 76 | NHAc | 1-F-i-Pr | H | H | 1-Me, 3-Me | — | —CH₂—CH₂— | —S— | |
| 77 | NHNH₂ | 1-F-i-Pr | H | H | 1-Me, 3-Me | — | —CH₂—CH₂— | —S— | |
| 78 | NHPiperidino | 1-F-i-Pr | H | H | 1-Me, 3-Me | — | —CH₂—CH₂— | —S— | |
| 79 | NH₂ | 1-F-i-Pr | H | H | 2-Me, 4-Me | — | —CH₂—CH₂— | —S— | 193–195 |
| 80 | NH₂ | 1-F-i-Pr | Et | H | 1-Me, 3-Me | — | —CH₂—CH₂— | —S— | |
| 81 | NH₂ | t1 | H | H | 1-Me, 3-Me | — | —CH₂—CHMe— | —S— | |
| 82 | NH₂ | 1-Me-c-Pr | H | H | 2-Me, 4-Me | — | —CH₂— | —S— | |
| 83 | NH₂ | 1-Me-c-Pr | H | H | 1-Me, 3-Me | — | —CMeH—CH₂— | —S— | |
| 84 | NH₂ | 1-Me-c-Pr | H | H | 4-Me | — | —CH₂—CHPh— | —S— | |
| 85 | NH₂ | 1-Me-c-Pr | H | H | 1-Me, 4-Me | — | —CH₂—CMe₂— | —S— | |
| 86 | NH₂ | 1-Me-c-Pr | H | H | 1-F, 3-F | — | —CH₂— | —S— | |
| 87 | NH₂ | 1-F-i-Pr | H | H | 1-Me, 3-Me | — | —CH₂— | —S— | |
| 88 | NH₂ | 1-F-i-Pr | H | H | 1-Me, 4-Me | — | —CH₂— | —S— | |
| 89 | NH₂ | 1-HO-i-Pr | H | H | 1-Me, 3-Me | — | —CH₂— | —S— | |
| 90 | NMe₂ | 1-F-i-Pr | H | H | 1-Me, 3-Me | —CH₂— | —CH₂— | —S— | |
| 91 | Morpholino | 1-F-i-Pr | H | H | 1-Me, 3-Me | — | —CH₂—CH₂— | —SO₂— | |
| 92 | NHAc | 1-F-i-Pr | H | H | 1-Me, 3-Me | — | —CH₂— | —S— | |
| 93 | NHNH₂ | 1-F-i-Pr | H | H | 1-Me, 3-Me | — | —CH₂— | —S— | |
| 94 | NHPiperidino | 1-F-i-Pr | H | H | 1-Me, 3-Me | — | —CH₂— | —S— | |
| 95 | NH₂ | 1-F-i-Pr | H | H | 2-Me, 4-Me | — | —CH₂— | —S— | |
| 96a | NH₂ | 1-F-i-Pr | H | H | 1-Me, 3-F | — | —CH₂— | —S— | |
| 97 | NH₂ | t1 | H | H | 1-Me, 3-Me | — | —CH₂— | —S— | |
| 98 | NH₂ | 1-Me-c-Pr | H | H | 2-Me, 4-Me | — | —CH₂— | —O— | |
| 99 | NH₂ | 1-Me-c-Pr | H | H | 1-Me, 3-Me | — | CMeHCH₂ | —O— | |
| 100 | NH₂ | 1-Me-c-Pr | H | H | 4-Me | — | CH₂CHPh— | —O— | |
| 101 | NH₂ | 1-Me-c-Pr | H | H | 1-Me, 4-Me | — | CH₂CMe₂— | —O— | |
| 102 | NH₂ | 1-Me-c-Pr | H | H | 1-F, 3-F | — | —CH₂— | —O— | |
| 103 | NH₂ | 1-F-i-Pr | H | H | 1-Me, 3-Me | — | —CH₂— | —O— | |
| 104 | NH₂ | 1-F-i-Pr | H | H | 1-Me, 4-Me | — | —CH₂— | —O— | |
| 105 | NH₂ | 1-HO-i-Pr | H | H | 1-Me, 3-Me | — | —CH₂— | —O— | |
| 106 | NMe₂ | 1-F-i-Pr | H | H | 1-Me, 3-Me | —CH₂— | —CH₂— | —O— | |
| 107a | Morpholino | 1-F-i-Pr | Me | H | 1-Me, 3-Me | — | —CH₂CH₂— | —O— | |
| 108 | NHAc | 1-F-i-Pr | H | H | 1-Me, 3-Me | — | —CH₂— | —O— | |
| 109 | NHNH₂ | 1-F-i-Pr | H | H | 1-Me, 3-Me | — | —CH₂— | —O— | |
| 110 | NHPiperidino | 1-F-i-Pr | H | H | 1-Me, 3-Me | — | —CH₂— | —O— | |
| 111 | NH₂ | 1-F-i-Pr | H | H | 2-Me, 4-Me | — | —CH₂— | —O— | |
| 112 | NH₂ | 1-F-i-Pr | H | Me | 1-Me, 3-Me | — | —CH₂— | —O— | |
| 113 | NH₂ | t1 | H | H | 1-Me, 3-Me | — | —CH₂— | —O— | |
| 114 | NH₂ | 1-Me-c-Pr | H | H | 2-Me, 4-Me | — | —CH₂—CH₂— | —O— | |
| 115 | NH₂ | 1-Me-c-Pr | H | H | 1-Me, 3-Me | — | —CH₂—CH₂— | —O— | |
| 116 | NH₂ | 1-Me-c-Pr | H | H | 4-Me | — | —CH₂—CH₂— | —O— | |
| 117 | NH₂ | 1-Me-c-Pr | H | H | 1-Me, 4-Me | — | —CH₂—CH₂— | —O— | |
| 118 | NH₂ | 1-Me-c-Pr | H | H | 1-F, 3-F | — | —CH₂—CH₂— | —O— | |
| 119 | NH₂ | 1-F-i-Pr | H | CH₂OMe | 1-Me, 3-Me | — | —CH₂—CH₂— | —O— | |
| 120 | NH₂ | 1-F-i-Pr | H | H | 1-Me, 4-Me | — | —CH₂—CH₂— | —O— | |
| 121 | NH₂ | 1-HO-i-Pr | H | H | 1-Me, 3-Me | — | —CH₂—CH₂— | —O— | |
| 122 | NMe₂ | 1-F-i-Pr | H | H | 1-Me, 3-Me | — | —CH₂—CH₂— | —O— | |
| 123 | Morpholino | 1-F-i-Pr | H | H | 1-Me, 3-Me | — | —CH₂—CH₂— | —O— | |
| 124 | NHAc | 1-F-i-Pr | H | H | 1-Me, 3-Me | — | —CH₂—CH₂— | —O— | |
| 125 | NHNH₂ | 1-F-i-Pr | H | H | 1-Me, 3-Me | — | —CH₂—CH₂— | —O— | |
| 126 | NHPiperidino | 1-F-i-Pr | H | H | 1-Me, 3-Me | — | —CH₂—CH₂— | —O— | |
| 127 | NH2 | 1-F-i-Pr | H | H | 2-Me, 4-Me | — | —CH₂—CH₂— | —O— | |

TABLE 1-continued

Compounds of the formula (I')

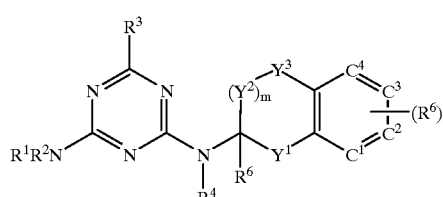

(I')

| No. | NR¹R² | R³ | R⁴ | R⁵ | (R⁶)ₙ | Y¹ | (Y²)ₘ | Y³ | Fp. (° C.) |
|---|---|---|---|---|---|---|---|---|---|
| 128a | NHPiperidino | 1-F-i-Pr | H | H | 2-Me, 3-Me | — | —CH₂—CH₂— | —O— | |
| 129 | NH₂ | t1 | H | H | 1-Me, 3-Me | — | —CH₂—CHMe— | —O— | |
| 130 | NH₂ | 1-Me-c-Pr | H | H | 2-Me, 4-Me | — | —CH₂—CH₂— | —NH— | |
| 131 | NH₂ | 1-Me-c-Pr | H | H | 1-Me, 3-Me | — | —CH₂—CH₂— | —NMe— | |
| 132 | NH₂ | 1-Me-c-Pr | H | H | 4-Me | — | —CH₂—CH₂— | —NH— | |
| 133 | NH₂ | 1-Me-c-Pr | H | H | 1-Me, 4-Me | — | —CH₂—CH₂— | —NAc— | |
| 134 | NH₂ | 1-Me-c-Pr | H | H | 1-F, 3-F | — | —CH₂—CH₂— | —NBz— | |
| 135 | NH₂ | 1-F-i-Pr | H | H | 1-Me, 3-Me | — | —CH₂—CH₂— | —NH— | |
| 136 | NH₂ | 1-F-i-Pr | H | H | 1-Me, 4-Me | — | —CH₂—CH₂— | —NO— | |
| 137 | NH₂ | 1-HO-i-Pr | H | H | 1-Me, 3-Me | — | —CH₂—CH₂— | —NH— | |
| 138 | NMe₂ | 1-F-i-Pr | H | H | 1-Me, 3-Me | — | —CH₂—CH₂— | —NPh— | |
| 139 | Morpholino | 1-F-i-Pr | H | H | 1-Me, 3-Me | — | —CH₂—CH₂— | —NEt— | |
| 140 | NHAc | 1-F-i-Pr | H | H | 1-Me, 3-Me | — | —CH₂—CH₂— | —N-i-Pr— | |
| 141 | NHNH₂ | 1-F-i-Pr | H | H | 1-Me, 3-Me | — | —CH₂—CH₂— | —N-n-Pr— | |
| 142 | NHPiperidino | 1-F-i-Pr | H | H | 1-Me, 3-Me | — | —CH₂—CH₂— | —NH— | |
| 143 | NH₂ | 1-F-i-Pr | H | H | 2-Me, 4-Me | — | —CH₂—CH₂— | —NH— | |
| 144 | NH₂ | 1-F-i-Pr | H | H | 1-Me, 3-Me | — | —CH₂—CH₂— | —N(CH₂-OMe)— | |
| 145 | NH₂ | t1 | H | H | 1-Me, 3-Me | — | —CH₂—CHMe— | —NPh— | |
| 146 | NH₂ | CF₃ | H | H | 2-Me, 4-Me | — | —CH₂—CH₂— | — | |
| 147 | NH₂ | CF₂CF₂H | H | H | 2-Me, 4-Me | — | —CH₂—CH₂— | — | |
| 148 | NH₂ | F-i-Pr | H | H | 2-Me, 4-Me | — | —CH₂—CH₂— | — | |
| 149 | NH₂ | 2-CF₃—Ph | H | H | 2-Me, 4-Me | — | —CH₂—CH₂— | — | |
| 150 | NHPiperidino | CF₂CF₂H | H | H | 2-Me, 4-Me | — | —CH₂—CH₂— | — | |
| 151 | NH₂ | F-i-Pr | H | H | 2-Me, 4-Ph | — | —CH₂— | —O— | |
| 152 | NH₂ | t-Bu | H | H | 2-Me, 4-Me | — | —CH₂—CH₂— | — | |
| 153 | NH₂ | CF₂CF₂H | H | H | 2-Ph, 4-Me | — | —CH₂—CH₂— | — | |
| 154a | NH₂ | F-i-Pr | H | H | 2,3,4-Me₃ | — | —CH₂—CH₂— | — | |
| 155 | NH₂ | 3-CF₃—Ph | H | H | 2-Me, 4-Me | — | —CH₂—CH₂— | — | |
| 156 | NH₂ | CFClCF₂H | H | H | 2-Me, 4-Me | — | —CH₂—CH₂— | — | |
| 157 | NH₂ | F-i-Pr | Me | Me | 2-Me, 4-Me | — | —CH₂—CH₂— | — | |
| 158 | NH₂ | Me | H | H | 2-Me, 4-Me | — | —CH₂—CH₂— | — | |
| 159 | NH₂ | CF₂CF₃ | H | H | 2-Me, 4-Me | — | —CH₂—CH₂— | — | |
| 160 | NH₂ | Et | H | H | 2-Me, 4-Me | — | —CMeH—CH₂— | — | |
| 161 | NH₂ | CF₂Me | H | H | 1-Me, 4-Me | — | —CH₂—CH₂— | — | |
| 162 | NH₂ | CF₂CF₂H | H | H | 1-Me, 4-Me | — | —CH₂—CH₂— | — | |
| 163 | NH₂ | F-i-Pr | H | H | 1-Me, 4-Me | — | —CH₂—CH₂— | — | |
| 164 | NH₂ | CCl₃ | H | H | 3-Me, 4-Me | — | —CH₂—CH₂— | — | |
| 165 | NH₂ | CF₂Ph | H | H | 3-Me, 4-Me | — | —CH₂—CH₂— | — | |
| 166 | NH₂ | CH₂COOMe | H | H | 3-Me, 4-Me | — | —CH₂—CH₂— | — | |
| 167 | NH₂ | CH₂CN | H | H | 2-Et | — | —CH₂—CH₂— | — | |
| 168 | NH₂ | CHMeCN | H | H | 2-Et, 4-Me | — | —CH₂—CH₂— | — | |
| 169 | NH₂ | 1-OMe—Et | H | H | 2-Et, 4-Me | — | —CH₂—CH₂— | — | |
| 170 | NH₂ | 2-F—Ph | H | H | 2-Me, 4-Me | — | —CH₂—CH₂— | — | |
| 171 | NH₂ | 3-F—Ph | H | H | 2-Me, 4-Me | — | —CH₂—CH₂— | — | |
| 172 | NH₂ | 4-F—Ph | H | H | 2-Me, 4-Me | — | —CH₂—CH₂— | — | |
| 173 | NH₂ | 2-Me—Ph | H | H | 2-Me, 4-Me | — | —CH₂—CH₂— | — | |
| 174 | NH₂ | 2-Et—Ph | H | H | 2-Me, 4-Me | — | —CH₂—CH₂— | — | |
| 175 | NH₂ | 2-OH—Ph | H | H | 2-Me, 4-Me | — | —CH₂—CH₂— | — | |
| 176 | NH₂ | 2-OMe—Ph | H | H | 2-Me, 4-Me | — | —CH₂—CH₂— | — | |
| 177 | NH₂ | 2-CN—Ph | H | H | 2-Me, 4-Me | — | —CH₂—CH₂— | — | |
| 178 | NH₂ | 2,4-F₂—Ph | H | H | 2-Me, 4-Me | — | —CH₂—CH₂— | — | |
| 179 | NH₂ | 1-F-c-Pr | H | H | 2-Me, 4-Me | — | —CH₂—CH₂— | — | |
| 180 | NH₂ | epoxid | H | H | 2-Me, 4-Me | — | —CH₂—CH₂— | — | |
| 181 | NH₂ | 1-Me-epoxid | H | H | 2-Me, 4-Me | — | —CH₂—CH₂— | — | |
| 182 | NH₂ | 1,2-Me₂-epoxid | H | H | 2-Me, 4-Me | — | —CH₂—CH₂— | — | |
| 183 | NH₂ | 1,2,2-Me₃-epoxid | H | H | 2-Me, 4-Me | — | —CH₂—CH₂— | — | |
| 184 | NH₂ | 1-Me-2-Et-epoxid | H | H | 2-Me, 4-Me | — | —CH₂—CH₂— | — | |
| 185 | NH₂ | 1-Me-2-n-Bu-epoxid | H | H | 2-Me, 4-Me | — | —CH₂—CH₂— | — | |
| 186 | NH₂ | 2-Me-epoxid | H | H | 2-Me, 4-Me | — | —CH₂—CH₂— | — | |

TABLE 1-continued

Compounds of the formula (I')

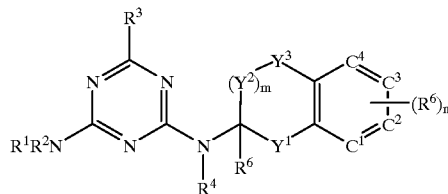

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 187 | NH$_2$ | t1 | H | H | 2-Me, 4-Me | — | —CH$_2$—CH$_2$— | — | |
| 188 | NH$_2$ | HO-i-Pr | H | H | 2-Me, 4-Me | — | —CH$_2$—CH$_2$— | — | |
| 189 | NH$_2$ | Cl-i-Pr | H | H | 2-Me, 4-Me | — | —CH$_2$—CH$_2$— | — | |
| 190 | NH$_2$ | MeO-i-Pr | H | H | 2-Me, 4-Me | — | —CH$_2$—CH$_2$— | — | |
| 191 | NH$_2$ | 1-HO—Et | H | H | 2-Me, 4-Me | — | —CH$_2$—CH$_2$— | — | |
| 192 | NH$_2$ | 1-MeO—Et | H | H | 2-Me, 4-Me | — | —CH$_2$—CH$_2$— | — | |
| 193 | NH$_2$ | 1-F—Et | H | H | 2-Me, 4-Me | — | —CH$_2$—CH$_2$— | — | |
| 194 | NH$_2$ | 1-Cl—Et | H | H | 2-Me, 4-Me | — | —CH$_2$—CH$_2$— | — | |
| 195 | NH$_2$ | 1-AcO—Et | H | H | 2-Me, 4-Me | — | —CH$_2$—CH$_2$— | — | |
| 196 | NH$_2$ | HO-i-Pr | H | H | 1-Me, 4-Me | — | —CH$_2$—CH$_2$— | — | |
| 197 | NH$_2$ | Cl-i-Pr | H | H | 3-Me, 4-Me | — | —CH$_2$—CH$_2$— | — | |
| 198 | NH$_2$ | CF$_3$ | H | H | H | — | —CH$_2$—CH$_2$— | — | |
| 199a | NH$_2$ | CHFCF$_3$ | H | H | H | — | —CH$_2$—CH$_2$— | — | f. Schaum |
| 200 | NH$_2$ | F-i-Pr | H | H | H | — | —CH$_2$—CH$_2$— | — | 166–169 |
| 201 | NH$_2$ | CF$_3$ | Ac | H | H | — | —CH$_2$—CH$_2$— | — | |
| 202 | NH$_2$ | CF$_2$CF$_2$H | H | H | H | — | —CH$_2$—CH$_2$— | — | |
| 203 | NH$_2$ | F-i-Pr | H | H | H | — | —CH$_2$— | —O— | |
| 204 | NH$_2$ | t-Bu | H | H | H | — | —CH$_2$—CH$_2$— | — | |
| 205a | NH$_2$ | CF$_2$CF$_2$H | H | H | H | — | —CHMeCH$_2$— | — | |
| 206 | NH$_2$ | F-i-Pr | Bz | H | H | — | —CH$_2$—CH$_2$— | — | |
| 207 | NH$_2$ | CF$_3$ | H | Me | H | — | —CH$_2$—CH$_2$— | — | |
| 208 | NH$_2$ | CFClCF$_2$H | H | H | H | — | —CH$_2$—CH$_2$— | — | |
| 209 | NH$_2$ | F-i-Pr | Ph | H | H | — | —CH$_2$—CH$_2$— | — | |
| 210 | NH$_2$ | Me | H | H | H | — | —CH$_2$—CH$_2$— | — | |
| 211 | NH$_2$ | CF$_2$CF$_3$ | H | H | H | — | —CH$_2$—CH$_2$— | — | |
| 212 | NH$_2$ | Et | H | H | H | — | —CMeH—CH$_2$— | — | |
| 213 | NH$_2$ | CF$_2$Me | H | H | H | — | —CH$_2$—CH$_2$— | — | |
| 214 | NH$_2$ | CF$_2$CF$_2$H | H | H | H | — | —CH$_2$—CH$_2$— | — | |
| 215 | NH$_2$ | F-i-Pr | CHO | H | H | — | —CH$_2$—CH$_2$— | — | |
| 216 | NH$_2$ | CCl$_3$ | H | H | H | — | —CH$_2$—CH$_2$— | — | |
| 217 | NH$_2$ | CF$_2$Ph | H | H | H | — | —CH$_2$—CH$_2$— | — | |
| 218 | NH$_2$ | CH$_2$COOMe | H | H | H | — | —CH$_2$—CH$_2$— | — | |
| 219 | NH$_2$ | CH$_2$CN | H | H | H | — | —CH$_2$—CH$_2$— | — | |
| 220 | NH$_2$ | CHMeCN | H | H | H | — | —CH$_2$—CH$_2$— | — | |
| 221 | NH$_2$ | 1-OMe—Et | H | H | H | — | —CH$_2$—CH$_2$— | — | |
| 222 | NH$_2$ | 2-F—Ph | H | H | H | — | —CH$_2$—CH$_2$— | — | |
| 223 | NH$_2$ | 3-F—Ph | H | H | H | — | —CH$_2$—CH$_2$— | — | |
| 224 | NH$_2$ | 4-F—Ph | H | H | H | — | —CH$_2$—CH$_2$— | — | |
| 225 | NH$_2$ | 2-Me—Ph | H | H | H | — | —CH$_2$—CH$_2$— | — | |
| 226 | NH$_2$ | 2-Et—Ph | H | H | H | — | —CH$_2$—CH$_2$— | — | |
| 227 | NH$_2$ | 2-OH—Ph | H | H | H | — | —CH$_2$—CH$_2$— | — | |
| 228 | NH$_2$ | 2-OMe—Ph | H | H | H | — | —CH$_2$—CH$_2$— | — | |
| 229 | NH$_2$ | 2-CN—Ph | H | H | H | — | —CH$_2$—CH$_2$— | — | |
| 230 | NH$_2$ | 2-F4-F—Ph | H | H | H | — | —CH$_2$—CH$_2$— | — | |
| 231 | NH$_2$ | 1-Me-c-Pr | H | H | H | — | —CH$_2$—CH$_2$— | — | f. Schaum |
| 232 | NH$_2$ | epoxid | H | H | H | — | —CH$_2$—CH$_2$— | — | |
| 233 | NH$_2$ | 1-Me-epoxid | H | H | H | — | —CH$_2$—CH$_2$— | — | |
| 234 | NH$_2$ | 1,2-Me$_2$-epoxid | H | H | H | — | —CH$_2$—CH$_2$— | — | |
| 235 | NH$_2$ | 1,2,2-Me$_3$-epoxid | H | H | H | — | —CH$_2$—CH$_2$— | — | |
| 236 | NH$_2$ | 1-Me-2-Et-epoxid | H | H | H | — | —CH$_2$—CH$_2$— | — | |
| 237 | NH$_2$ | 1-Me-2-n-Bu-epoxid | H | H | H | — | —CH$_2$—CH$_2$— | — | |
| 238 | NH$_2$ | 2-Me-epoxid | H | H | H | — | —CH$_2$—CH$_2$— | — | |
| 239 | NH$_2$ | t1 | H | H | H | — | —CH$_2$—CH$_2$— | — | |
| 240 | NH$_2$ | HO-i-Pr | H | H | H | — | —CH$_2$—CH$_2$— | — | 163–165 |
| 241 | NH$_2$ | Cl-i-Pr | H | H | H | — | —CH$_2$—CH$_2$— | — | |
| 242 | NH$_2$ | MeO-i-Pr | H | H | H | — | —CH$_2$—CH$_2$— | — | |
| 243 | NH$_2$ | 1-HO—Et | H | H | H | — | —CH$_2$—CH$_2$— | — | |
| 244a | NH$_2$ | 1-PhO—Et | H | H | H | — | —CH$_2$—CH$_2$— | — | |
| 245 | NH$_2$ | 1-F—Et | H | H | H | — | —CH$_2$—CH$_2$— | — | |
| 246 | NH$_2$ | 1-Cl—Et | H | H | H | — | —CH$_2$—CH$_2$— | — | |

TABLE 1-continued

Compounds of the formula (I')

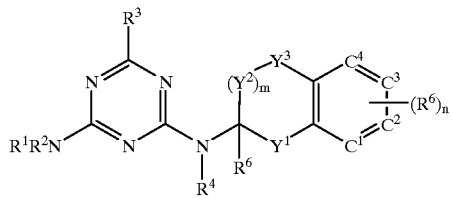

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 247 | NH$_2$ | 1-AcO—Et | H | H | H | — | —CH$_2$—CH$_2$— | — | |
| 248 | NH$_2$ | HO-i-Pr | H | CH$_2$OMe | H | — | —CH$_2$—CH$_2$— | — | |
| 249 | NH$_2$ | Cl-i-Pr | H | CH$_2$OMe | H | — | —CH$_2$—CH$_2$— | — | |
| 250 | NH$_2$ | Et | H | Me | H | — | CH$_2$ | O | |
| 251 | NH$_2$ | 1-Cl—Et | H | H | H | — | CH$_2$ | NMe | |
| 252 | NH$_2$ | 1-MeO—Et | H | H | 1-Me, 4-Me | CH$_2$ | CH$_2$ | O | |
| 253 | NH$_2$ | 2-MeO—Et | H | H | 1-Me, 4-F | — | CHMeCH$_2$ | | |
| 254 | NH$_2$ | c-Pr | Me | COOMe | 2-Me, 4-Cl | — | CH$_2$CPhH | O | |
| 255 | NH$_2$ | 1-Me-c-Pr | Me | CN | 2-Me, 4-Me | — | CH$_2$ | CH$_2$ | |
| 256 | NH$_2$ | 1-F-c-Pr | Ac | Ac | 2-Me, 4-Me | — | CH$_2$ | CH$_2$ | |
| 257 | NH$_2$ | 1-Cl-c-Pr | CHO | Me | 2-Me, 4-Me | — | CH$_2$ | CH$_2$ | |
| 258 | NMe$_2$ | Me | H | H | 2-Me, 4-Me | — | CH$_2$ | CH$_2$ | |
| 259 | NHCHO | F-i-Pr | CH$_2$OMe | H | 2-Me, 4-CF$_3$ | CH$_2$ | CH$_2$ | — | |
| 260 | Morpholino | F-i-Pr | Bz | Me | 1-Me, 4-OMe | — | CH$_2$—CHMe | NMe | |
| 261 | Piperidino | F-i-Pr | H | H | 3-OMe | — | CH$_2$—CH$_2$ | CHMe | |
| 262 | NHAc | F-i-Pr | H | H | 2-Me, 4-Me | — | CH$_2$—CHPh | — | |
| 263 | NHNH$_2$ | OH-i-Pr | Me | H | 3-Me, 4-Me | — | CH$_2$—CHMe | S | |
| 264 | NEt$_2$ | OH-i-Pr | H | H | 3-Me, 4-Et | — | CHMe—CH$_2$ | S | |
| 265 | NHPh | OH-i-Pr | H | H | 2-Ac, 4-Me | CO | CH$_2$—CH$_2$ | S | |
| 266 | NHBz | OMe-i-Pr | H | H | 3-OPh | CHMe | CH$_2$—CH$_2$ | S | |
| 267 | NHCOPh | Me | H | H | 3-OCOPh | CHEt | CH$_2$—CH$_2$ | O | |
| 268 | NH$_2$ | CF$_3$ | 4-Cl-Bz | H | 2-Me, 4-Me | — | CH$_2$—CH$_2$ | O | |
| 269 | NH$_2$ | CF$_2$CF$_2$H | H | Me | 2-Me, 4-Me | — | CH$_2$—CH$_2$ | S | |
| 270 | NH$_2$ | CH$_2$CF$_3$ | H | Et | 2-Me, 4-Me | — | CH$_2$—CH$_2$ | S | |
| 271 | NH$_2$ | 1-CF$_3$-c-Pr | H | H | 2-Me, 4-Me | — | CH$_2$—CH$_2$ | S | |
| 272 | NH$_2$ | CF$_3$ | H | H | H | —CH$_2$— | —CH$_2$—CH$_2$— | — | |
| 273 | NH$_2$ | CF$_2$CF$_2$H | H | H | H | —CH$_2$— | —CH$_2$—CH$_2$— | — | |
| 274 | NH$_2$ | F-i-Pr | H | H | H | —CH$_2$— | —CH$_2$—CH$_2$— | — | 72–75 |
| 275 | NH$_2$ | CF$_3$ | 3-Cl-Bz | H | H | —CH$_2$— | —CH$_2$—CH$_2$— | — | |
| 276 | NH$_2$ | CF$_2$CF$_2$H | H | Et | H | —CH$_2$— | —CH$_2$—CH$_2$— | — | |
| 277 | NH$_2$ | F-i-Pr | H | Me | H | —CH$_2$— | —CH$_2$— | —O— | |
| 278 | NH$_2$ | t-Bu | H | H | H | —CH$_2$— | —CH$_2$—CH$_2$— | — | |
| 279 | NH$_2$ | CF$_2$CF$_2$H | H | Me | H | —CH$_2$— | —CH$_2$—CH$_2$— | — | |
| 280 | NHNH-Ph | F-i-Pr | H | H | H | —CH$_2$— | —CH$_2$—CH$_2$— | — | |
| 281 | NH$_2$ | CF$_3$ | 4-Cl-Bz | H | H | —CH$_2$— | —CH$_2$—CH$_2$— | — | |
| 282 | NH$_2$ | CFClCF$_2$H | H | H | H | —CH$_2$— | —CH$_2$—CH$_2$— | — | |
| 283 | NH$_2$ | F-i-Pr | H | Ac | H | —CH$_2$— | —CH$_2$—CH$_2$— | — | |
| 284 | NH$_2$ | Me | H | H | H | —CH$_2$— | —CH$_2$—CH$_2$— | — | |
| 285 | NH$_2$ | CF$_2$CF$_3$ | H | H | H | —CH$_2$— | —CH$_2$—CH$_2$— | — | |
| 286 | NH$_2$ | Et | H | H | H | —CH$_2$— | —CMeH—CH$_2$— | — | |
| 287 | NH$_2$ | CF$_2$Me | H | H | H | —CH$_2$— | —CH$_2$—CH$_2$— | — | |
| 288 | NH$_2$ | CF$_2$CF$_2$H | H | H | H | —CH$_2$— | —CH$_2$—CH$_2$— | — | |
| 289 | NH$_2$ | F-i-Pr | H | Et | H | —CH$_2$— | —CH$_2$—CH$_2$— | — | |
| 290 | NH$_2$ | CCl$_3$ | H | H | H | —CH$_2$— | —CH$_2$—CH$_2$— | — | |
| 291 | NH$_2$ | CF$_2$Ph | H | H | H | —CH$_2$— | —CH$_2$—CH$_2$— | — | |
| 292 | NH$_2$ | CH$_2$COOMe | H | H | H | —CH$_2$— | —CH$_2$—CH$_2$— | — | |
| 293 | NH$_2$ | CH$_2$CN | H | H | H | —CH$_2$— | —CH$_2$—CH$_2$— | — | |
| 294 | NH$_2$ | CHMeCN | H | H | H | —CH$_2$— | —CH$_2$—CH$_2$— | — | |
| 295 | NH$_2$ | 1-OMe—Et | H | H | H | —CH$_2$— | —CH$_2$—CH$_2$— | — | |
| 296 | NH$_2$ | 2-F—Ph | H | H | H | —CH$_2$— | —CH$_2$—CH$_2$— | — | |
| 297 | NH$_2$ | 3-F—Ph | H | H | H | —CH$_2$— | —CH$_2$—CH$_2$— | — | |
| 298 | NH$_2$ | 4-F—Ph | H | H | H | —CH$_2$— | —CH$_2$—CH$_2$— | — | |
| 299 | NH$_2$ | 2-Me—Ph | H | H | H | —CH$_2$— | —CH$_2$—CH$_2$— | — | |
| 300 | NH$_2$ | 2-Et—Ph | H | H | H | —CH$_2$— | —CH$_2$—CH$_2$— | — | |
| 301 | NH$_2$ | 2-OH—Ph | H | H | H | —CH$_2$— | —CH$_2$—CH$_2$— | — | |
| 302 | NH$_2$ | 2-OMe—Ph | H | H | H | —CH$_2$— | —CH$_2$—CH$_2$— | — | |
| 303 | NH$_2$ | 2-CN—Ph | H | H | H | —CH$_2$— | —CH$_2$—CH$_2$— | — | |
| 304 | NH$_2$ | 2,4-F$_2$—Ph | H | H | H | —CH$_2$— | —CH$_2$—CH$_2$— | — | |
| 305 | NH$_2$ | 1-Me-c-Pr | H | H | H | —CH$_2$— | —CH$_2$—CH$_2$— | — | 153–154 |
| 306 | NH$_2$ | epoxid | H | H | H | —CH$_2$— | —CH$_2$—CH$_2$— | — | |
| 307 | NH$_2$ | 1-Me-epoxid | H | H | H | —CH$_2$— | —CH$_2$—CH$_2$— | — | |
| 308 | NH$_2$ | 1,2-Me$_2$-epoxid | H | H | H | —CH$_2$— | —CH$_2$—CH$_2$— | — | |

TABLE 1-continued

Compounds of the formula (I')

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 309 | NH$_2$ | 1,2,2-Me$_3$-epoxid | H | H | H | —CH$_2$— | —CH$_2$—CH$_2$— | — | |
| 310 | NH$_2$ | 1-Me-2-Et-epoxid | H | H | H | —CH$_2$— | —CH$_2$—CH$_2$— | — | |
| 311 | NH$_2$ | 1-Me-2-n-Bu-epoxid | H | H | H | —CH$_2$— | —CH$_2$—CH$_2$— | — | |
| 312 | NH$_2$ | 2-Me-epoxid | H | H | H | —CH$_2$— | —CH$_2$—CH$_2$— | — | |
| 313 | NH$_2$ | t1 | H | H | H | —CH$_2$— | —CH$_2$—CH$_2$— | — | |
| 314 | NH$_2$ | HO-i-Pr | H | H | H | —CH$_2$— | —CH$_2$—CH$_2$— | — | 145–146 |
| 315 | NH$_2$ | Cl-i-Pr | H | H | H | —CH$_2$— | —CH$_2$—CH$_2$— | — | |
| 316 | NH$_2$ | MeO-i-Pr | H | H | H | —CH$_2$— | —CH$_2$—CH$_2$— | — | |
| 317 | NH$_2$ | 1-HO—Et | H | H | H | —CH$_2$— | —CH$_2$—CH$_2$— | — | |
| 318 | NH$_2$ | 1-MeO—Et | H | H | H | —CH$_2$— | —CH$_2$—CH$_2$— | — | |
| 319 | NH$_2$ | 1-F—Et | H | H | H | —CH$_2$— | —CH$_2$—CH$_2$— | — | |
| 320 | NH$_2$ | 1-Cl—Et | H | H | H | —CH$_2$— | —CH$_2$—CH$_2$— | — | |
| 321 | NH$_2$ | 1-AcO—Et | H | H | H | —CH$_2$— | —CH$_2$—CH$_2$— | — | |
| 322 | NH$_2$ | HO-i-Pr | CH$_2$CN | H | H | —CH$_2$— | —CH$_2$—CH$_2$— | — | |
| 323 | NH$_2$ | Cl-i-Pr | CH$_2$CH$_2$—CN | H | H | —CH$_2$— | —CH$_2$—CH$_2$— | — | |
| 324 | NH$_2$ | CF$_3$ | H | H | 2-Me, 4-Me | —CH$_2$— | —CH$_2$—CH$_2$— | — | |
| 325 | NH$_2$ | CF$_2$CF$_2$H | H | H | 2-Me, 4-Me | —CH$_2$— | —CH$_2$—CH$_2$— | — | |
| 326 | NH$_2$ | F-i-Pr | H | H | 2-Me, 4-Me | —CH$_2$— | —CH$_2$—CH$_2$— | — | |
| 327 | NH$_2$ | CF$_3$ | CH$_2$OMe | H | 2-Me, 4-Me | —CH$_2$— | —CH$_2$—CH$_2$— | — | |
| 328 | NH-c-Pr | CF$_2$CF$_2$H | H | H | 2-Me, 4-Me | —CH$_2$— | —CH$_2$—CH$_2$— | — | |
| 329 | NH$_2$ | F-i-Pr | H | H | 2-Me, 4-Me | —CH$_2$— | —CH$_2$— | —O— | |
| 330 | NH$_2$ | t-Bu | H | H | 2-Me, 4-Me | —CH$_2$— | —CH$_2$—CH$_2$— | — | |
| 331 | NHNH-Me | CF$_2$CF$_2$H | H | H | 2-Me, 4-Me | —CH$_2$— | —CH$_2$—CH$_2$— | — | |
| 332 | NH$_2$ | F-i-Pr | CH$_2$OMe | H | 2-Me, 4-Me | —CH$_2$— | —CH$_2$—CH$_2$— | — | |
| 333a | NHMe | CF$_3$ | H | H | 2-Me, 4-Me | —CH$_2$— | —CH$_2$—CH$_2$— | — | |
| 334 | NH$_2$ | CFClCF$_2$H | H | Me | 2-Me, 4-Me | —CH$_2$— | —CH$_2$—CH$_2$— | — | |
| 335 | NH$_2$ | F-i-Pr | Et | H | 2-Me, 4-Me | —CH$_2$— | —CH$_2$—CH$_2$— | — | |
| 336 | NH$_2$ | Me | H | H | 2-Me, 4-Me | —CH$_2$— | —CH$_2$—CH$_2$— | — | |
| 337 | NH$_2$ | CF$_2$CF$_3$ | H | H | 2-Me, 4-Me | —CH$_2$— | —CH$_2$—CH$_2$— | — | |
| 338 | NH$_2$ | Et | H | H | 2-Me, 4-Me | —CH$_2$— | —CMeH—CH$_2$— | — | |
| 339 | NH$_2$ | CF$_2$Me | H | H | 1-Me, 4-Me | —CH$_2$— | —CH$_2$—CH$_2$— | — | |
| 340 | NH$_2$ | CF$_2$CF$_2$H | H | H | 1-Me, 4-Me | —CH$_2$— | —CH$_2$—CH$_2$— | — | |
| 341 | NH$_2$ | F-i-Pr | H | Me | 1-Me, 4-Me | —CH$_2$— | —CH$_2$—CH$_2$— | — | |
| 342 | NH$_2$ | CCl$_3$ | H | H | 3-Me, 4-Me | —CH$_2$— | —CH$_2$—CH$_2$— | — | |
| 343 | NH$_2$ | CF$_2$Ph | H | H | 3-Me, 4-Me | —CH$_2$— | —CH$_2$—CH$_2$— | — | |
| 344 | NH$_2$ | CH$_2$COOMe | H | H | 3-Me, 4-Me | —CH$_2$— | —CH$_2$—CH$_2$— | — | |
| 345 | NH$_2$ | CH$_2$CN | H | H | 2-Et | —CH$_2$— | —CH$_2$—CH$_2$— | — | |
| 346 | NH$_2$ | CHMeCN | H | H | 2-Et, 4-Me | —CH$_2$— | —CH$_2$—CH$_2$— | — | |
| 347 | NH$_2$ | 1-OMe—Et | H | H | 2-Et, 4-Me | —CH$_2$— | —CH$_2$—CH$_2$— | — | |
| 348 | NH$_2$ | 2-F—Ph | H | H | 2-Me, 4-Me | —CH$_2$— | —CH$_2$—CH$_2$— | — | |
| 349 | NH$_2$ | 3-F—Ph | H | H | 2-Me, 4-Me | —CH$_2$— | —CH$_2$—CH$_2$— | — | |
| 350 | NH$_2$ | 4-F—Ph | H | H | 2-Me, 4-Me | —CH$_2$— | —CH$_2$—CH$_2$— | — | |
| 351 | NH$_2$ | 2-Me—Ph | H | H | 2-Me, 4-Me | —CH$_2$— | —CH$_2$—CH$_2$— | — | |
| 352 | NH$_2$ | 2-Et—Ph | H | H | 2-Me, 4-Me | —CMe$_2$— | —CH$_2$—CH$_2$— | — | |
| 353 | NH$_2$ | 2-OH—Ph | H | H | 2-Me,4-Me | CMeH— | —CH$_2$—CH$_2$— | — | |
| 354 | NH$_2$ | 2-OMe—Ph | H | H | 2-Me, 4-Me | —CH$_2$— | —CH$_2$—CH$_2$— | — | |
| 355 | NH$_2$ | 2-CN—Ph | H | H | 2-Me, 4-Me | —CH$_2$— | —CH$_2$—CH$_2$— | — | |
| 356 | NH$_2$ | 2,4-F$_2$—Ph | H | H | 2-Me, 4-Me | —CH$_2$— | —CH$_2$—CH$_2$— | — | |
| 357 | NH$_2$ | 1-F-c-Pr | H | H | 2-Me, 4-Me | CHOH | —CH$_2$—CH$_2$— | — | |
| 358 | NH$_2$ | epoxid | H | H | 2-Me, 4-Me | —CH$_2$— | —CH$_2$—CH$_2$— | — | |
| 359 | NH$_2$ | 1-Me-epoxid | H | H | 2-Me, 4-Me | —CH$_2$— | —CH$_2$—CH$_2$— | — | |
| 360 | NH$_2$ | 1,2-Me$_2$-epoxid | H | H | 2-Me, 4-Me | —CH$_2$— | —CH$_2$—CH$_2$— | — | |
| 361 | NH$_2$ | 1,2,2-Me$_3$-epoxid | H | H | 2-Me, 4-Me | —CH$_2$— | —CH$_2$—CH$_2$— | — | |
| 362 | NH$_2$ | 1-Me-2-Et-epoxid | H | H | 2-Me, 4-Me | —CH$_2$— | —CH$_2$—CH$_2$— | — | |
| 363 | NH$_2$ | 1-Me-2-n-Bu-epoxid | H | H | 2-Me, 4-Me | —CH$_2$— | —CH$_2$—CH$_2$— | — | |
| 364 | NH$_2$ | 2-Me-epoxid | H | H | 2-Me, 4-Me | —CH$_2$— | —CH$_2$—CH$_2$— | — | |

TABLE 1-continued

Compounds of the formula (I')

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 365 | NH$_2$ | t1 | H | H | 2-Me, 4-Me | —CH$_2$— | —CH$_2$—CH$_2$— | — | |
| 366 | NH$_2$ | HO-i-Pr | H | H | 2-Me, 4-Me | —CH$_2$— | —CH$_2$—CH$_2$— | — | |
| 367 | NH$_2$ | Cl-i-Pr | H | H | 2-Me, 4-Me | —CH$_2$— | —CH$_2$—CH$_2$— | — | |
| 368 | NH$_2$ | MeO-i-Pr | H | H | 2-Me, 4-Me | —CH$_2$— | —CH$_2$—CH$_2$— | — | |
| 369 | NH$_2$ | 1-HO—Et | H | H | 2-Me, 4-Me | —CH$_2$— | —CH$_2$—CH$_2$— | — | |
| 370 | NH$_2$ | 1-MeO—Et | H | H | 2-Me, 4-Me | —CH$_2$— | —CH$_2$—CH$_2$— | — | |
| 371 | NH$_2$ | 1-F—Et | H | H | 2-Me, 4-Me | —CH$_2$— | —CH$_2$—CH$_2$— | — | |
| 372 | NH$_2$ | 1-Cl—Et | H | H | 2-Me, 4-Me | —CH$_2$— | —CH$_2$—CH$_2$— | — | |
| 373 | NH$_2$ | 1-AcO—Et | H | H | 2-Me, 4-Me | —CH$_2$— | —CH$_2$—CH$_2$— | — | |
| 374 | NH$_2$ | HO-i-Pr | H | H | 1-Me, 4-Me | —CH$_2$— | —CH$_2$—CH$_2$— | — | |
| 375 | NH$_2$ | Cl-i-Pr | H | H | 3-Me, 4-Me | —CH$_2$— | —CH$_2$—CH$_2$— | — | |
| 376 | NH$_2$ | CF$_3$ | H | H | H | —CH$_2$— | —CH$_2$— | — | |
| 377 | NH$_2$ | CF$_2$CF$_2$H | H | H | H | —CH$_2$— | —CH$_2$— | — | |
| 378 | NH$_2$ | F-i-Pr | H | H | H | —CH$_2$— | —CH$_2$— | — | 168–170 |
| 379 | NH$_2$ | CF$_3$ | H | CH$_2$OMe | H | —CH$_2$— | —CH$_2$— | — | |
| 380 | NH$_2$ | CF$_2$CF$_2$H | H | CH$_2$OMe | H | —CH$_2$— | —CH$_2$— | — | |
| 381 | NH$_2$ | F-i-Pr | H | CH$_2$OMe | H | —CO— | —CH$_2$— | — | |
| 382 | NH$_2$ | t-Bu | H | H | H | —CH$_2$— | —CH$_2$— | — | |
| 383 | NH$_2$ | CF$_2$CF$_2$H | H | Me | H | —CH$_2$— | —CH$_2$— | — | |
| 384 | NH$_2$ | F-i-Pr | H | CH$_2$OMe | H | —CH$_2$— | —CH$_2$— | — | |
| 385 | NH$_2$ | CF$_3$ | H | Me | H | —CH$_2$— | —CH$_2$— | — | |
| 386 | NH$_2$ | CFClCF$_2$H | H | H | H | —CH$_2$— | —CH$_2$— | — | |
| 387 | NH$_2$ | F-i-Pr | H | Ph | H | —CH$_2$— | —CH$_2$— | — | |
| 388 | NH$_2$ | Me | H | H | H | —CH$_2$— | —CH$_2$— | — | |
| 389 | NH$_2$ | CF$_2$CF$_3$ | H | H | H | —CH$_2$— | —CH$_2$— | — | |
| 390 | NH$_2$ | Et | H | H | H | —CH$_2$— | —CH$_2$— | — | |
| 391 | NH$_2$ | CF$_2$Me | H | H | H | —CH$_2$— | —CH$_2$— | — | |
| 392 | NH$_2$ | CF$_2$CF$_2$H | Bz | H | H | —CH$_2$— | —CH$_2$— | — | |
| 393 | NH$_2$ | F-i-Pr | H | i-Pr | H | —CH$_2$— | —CH$_2$— | — | |
| 394 | NH$_2$ | CCl$_3$ | H | H | H | —CH$_2$— | —CH$_2$— | — | |
| 395 | NH$_2$ | CF$_2$Ph | H | H | H | —CH$_2$— | —CH$_2$— | — | |
| 396 | NH$_2$ | CH$_2$COOMe | H | H | H | —CH$_2$— | —CH$_2$— | — | |
| 397 | NH$_2$ | CH$_2$CN | H | H | H | —CH$_2$— | —CH$_2$— | — | |
| 398 | NH$_2$ | CHMeCN | H | H | H | —CH$_2$— | —CH$_2$— | — | |
| 399 | NH$_2$ | 1-OMe—Et | H | H | H | —CH$_2$— | —CH$_2$— | — | |
| 400 | NH$_2$ | 2-F—Ph | H | H | H | —CH$_2$— | —CH$_2$— | — | |
| 401 | NH$_2$ | 3-F—Ph | H | H | H | —CH$_2$— | —CH$_2$— | — | |
| 402 | NH$_2$ | 4-F—Ph | H | H | H | —CH$_2$— | —CH$_2$— | — | |
| 403 | NH$_2$ | 2-Me—Ph | H | H | H | —CH$_2$— | —CH$_2$— | — | |
| 404 | NH$_2$ | 2-Et—Ph | H | H | H | —CH$_2$— | —CH$_2$— | — | |
| 405 | NH$_2$ | 2-OH—Ph | H | H | H | —CH$_2$— | —CH$_2$— | — | |
| 406 | NH$_2$ | 2-OMe—Ph | H | H | H | —CH$_2$— | —CH$_2$— | — | |
| 407 | NH$_2$ | 2-CN—Ph | H | H | H | —CH$_2$— | —CH$_2$— | — | |
| 408 | NH$_2$ | 2,4-F$_2$—Ph | H | H | H | —CH$_2$— | —CH$_2$— | — | |
| 409 | NH$_2$ | 1-Me-c-Pr | H | H | H | —CH$_2$— | —CH$_2$— | — | 120–123 |
| 410 | NH$_2$ | epoxid | H | H | H | —CH$_2$— | —CH$_2$— | — | |
| 411 | NH$_2$ | 1-Me-epoxid | H | H | H | —CH$_2$— | —CH$_2$— | — | |
| 412 | NH$_2$ | 1,2-Me$_2$-epoxid | H | H | H | —CH$_2$— | —CH$_2$— | — | |
| 413 | NH$_2$ | 1,2,2-Me$_3$-epoxid | H | H | H | —CH$_2$— | —CH$_2$— | — | |
| 414 | NH$_2$ | 1-Me-2-Et-epoxid | H | H | H | —CH$_2$— | —CH$_2$— | — | |
| 415 | NH$_2$ | 1-Me-2-n-Bu-epoxid | H | H | H | —CH$_2$— | —CH$_2$— | — | |
| 416 | NH$_2$ | 2-Me-epoxid | H | H | H | —CH$_2$— | —CH$_2$— | — | |
| 417 | NH$_2$ | t1 | H | H | H | —CH$_2$— | —CH$_2$— | — | |
| 418 | NH$_2$ | HO-i-Pr | H | H | H | —CH$_2$— | —CH$_2$— | — | 188–190 |
| 419 | NH$_2$ | Cl-i-Pr | H | H | H | —CH$_2$— | —CH$_2$— | — | |
| 420 | NH$_2$ | MeO-i-Pr | H | H | H | —CH$_2$— | —CH$_2$— | — | |
| 421 | NH$_2$ | 1-HO—Et | H | H | H | —CH$_2$— | —CH$_2$— | — | |
| 422 | NH$_2$ | 1-MeO—Et | H | H | H | —CH$_2$— | —CH$_2$— | — | |
| 423 | NH$_2$ | 1-F—Et | H | H | H | —CH$_2$— | —CH$_2$— | — | |
| 424 | NH$_2$ | 1-Cl—Et | H | H | H | —CH$_2$— | —CH$_2$— | — | |

TABLE 1-continued

Compounds of the formula (I')

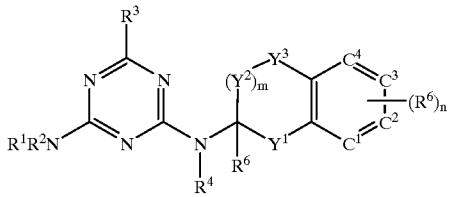

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 425 | NH$_2$ | 1-AcO—Et | H | H | H | —CH$_2$— | —CH$_2$— | — | |
| 426 | NH$_2$ | HO-i-Pr | H | H | H | —CH$_2$— | —CHPh— | — | |
| 427 | NH$_2$ | Cl-i-Pr | H | H | H | —CH$_2$— | —CHPh— | — | |
| 428 | NH$_2$ | CF$_3$ | H | H | 2-Me, 4-Me | —CH$_2$— | —CH$_2$— | — | |
| 429 | NH$_2$ | CF$_2$CF$_2$H | Me | H | 2-Me, 4-Me | —CH$_2$— | —CH$_2$— | — | |
| 430 | NH$_2$ | F-i-Pr | H | H | 2-Me, 4-Me | —CH$_2$— | —CH$_2$— | — | |
| 431 | NH$_2$ | CF$_3$ | Me | H | 2-Me, 4-Me | —CH$_2$— | —CH$_2$— | — | |
| 432 | NH$_2$ | CF$_2$CF$_2$H | H | H | 2-Me, 4-Me | —CH$_2$— | —CH$_2$— | — | |
| 433 | NH$_2$ | F-i-Pr | Me | H | 2-Me, | —CH$_2$— | —CH$_2$— | — | |
| 434 | NH$_2$ | t-Bu | H | H | 2-Me, 4-Me | —CH$_2$— | —CH$_2$— | — | |
| 435 | NH$_2$ | CF$_2$CF$_2$H | Ac | H | 2-Me, 4-Me | —CH$_2$— | —CH$_2$— | — | |
| 436 | NH$_2$ | F-i-Pr | Et | H | 2-Me, 4-Me | —CH$_2$— | —CH$_2$— | — | |
| 437a | NH-i-Pr | CF$_3$ | CH$_2$OMe | H | 2-Me, 4-Me | —CH$_2$— | —CH$_2$— | — | |
| 438 | NH$_2$ | CFClCF$_2$H | H | H | 2-Me, 4-Me | —CH$_2$— | —CH$_2$— | — | |
| 439 | NH$_2$ | F-i-Pr | Ac | H | 2-Me, 4-Me | —CH$_2$— | —CH$_2$— | — | |
| 440 | NH$_2$ | Me | H | H | 2-Me, 4-Me | —CH$_2$— | —CH$_2$— | — | |
| 441 | NH$_2$ | CF$_2$CF$_3$ | H | H | 2-Me, 4-Me | —CH$_2$— | —CH$_2$— | — | |
| 442 | NH$_2$ | Et | H | H | 2-Me, 4-Me | —CH$_2$— | —CH$_2$— | — | |
| 443 | NH$_2$ | CF$_2$Me | H | H | 1-Me, 4-Me | —CH$_2$— | —CH$_2$— | — | |
| 444 | NH$_2$ | CF$_2$CF$_2$H | H | H | 1-Me, 4-Me | —CH$_2$— | —CH$_2$— | — | |
| 445 | NH$_2$ | F-i-Pr | H | H | 1-Me, 4-Me | —CH$_2$— | —CH$_2$— | — | |
| 446 | NH$_2$ | CCl$_3$ | H | H | 3-Me, 4-Me | —CH$_2$— | —CH$_2$— | — | |
| 447 | NH$_2$ | CF$_2$Ph | H | H | 3-Me, 4-Me | —CH$_2$— | —CH$_2$— | — | |
| 448 | NH$_2$ | CH$_2$COOMe | H | H | 3-Me, 4-Me | —CH$_2$— | —CH$_2$— | — | |
| 449 | NH$_2$ | CH$_2$CN | H | H | 2-Et | —CH$_2$— | —CH$_2$— | — | |
| 450 | NH$_2$ | CHMeCN | H | H | 2-Et, 4-Me | —CH$_2$— | —CH$_2$— | — | |
| 451 | NH$_2$ | 1-OMe—Et | H | H | 2-Et, 4-Me | —CH$_2$— | —CH$_2$— | — | |
| 452 | NH$_2$ | 2-F—Ph | H | H | 2-Me, 4-Me | —CH$_2$— | —CH$_2$— | — | |
| 453 | NH$_2$ | 3-F—Ph | H | H | 2-Me, 4-Me | —CH$_2$— | —CH$_2$— | — | |
| 454 | NH$_2$ | 4-F—Ph | H | H | 2-Me, 4-Me | —CH$_2$— | —CH$_2$— | — | |
| 455 | NH$_2$ | 2-Me—Ph | H | H | 2-Me, 4-Me | —CH$_2$— | —CH$_2$— | — | |
| 456 | NH$_2$ | 2-Et—Ph | H | H | 2-Me, 4-Me | —CMe$_2$— | —CH$_2$— | — | |
| 457 | NH$_2$ | 2-OH—Ph | H | H | 2-Me, 4-Me | —CMeH— | —CH$_2$— | — | |
| 458 | NH$_2$ | 2-OMe—Ph | H | H | 2-Me, 4-Me | —CH$_2$— | —CH$_2$— | — | |
| 459 | NH$_2$ | 2-CN—Ph | H | H | 2-Me, 4-Me | —CH$_2$— | —CH$_2$— | — | |
| 460 | NH$_2$ | 2-F4-F—Ph | H | H | 2-Me, 4-Me | —CH$_2$— | —CH$_2$— | — | |
| 461 | NH$_2$ | 1-F-c-Pr | H | H | 2-Me, 4-Me | —COHH— | —CH$_2$— | — | |
| 462 | NH$_2$ | epoxid | H | H | 2-Me, 4-Me | —CH$_2$— | —CH$_2$— | — | |
| 463 | NH$_2$ | 1-Me-epoxid | H | H | 2-Me, 4-Me | —CH$_2$— | —CH$_2$— | — | |
| 464 | NH$_2$ | 1-Me-2-Me-epoxid | H | H | 2-Me,4-Me | —CH$_2$— | —CH$_2$— | — | |
| 465 | NH$_2$ | 1,2,2-Me$_3$-epoxid | H | H | 2-Me, 4-Me | | | | |
| 466 | NH$_2$ | 1-Me-2-Et-epoxid | H | H | 2-Me, 4-Me | —CH$_2$— | —CH$_2$— | — | |
| 467 | NH$_2$ | 1-Me-2-n-Bu-epoxid | H | H | 2-Me, 4-Me | —CH$_2$— | —CH$_2$— | — | |
| 468 | NH$_2$ | 2-Me-epoxid | H | H | 2-Me, 4-Me | —CH$_2$— | —CH$_2$— | — | |
| 469 | NH$_2$ | t1 | H | H | 2-Me, 4-Me | —CH$_2$— | —CH$_2$— | — | |
| 470 | NH$_2$ | HO-i-Pr | H | H | 2-Me, 4-Me | —CH$_2$— | —CH$_2$— | — | |
| 471 | NH$_2$ | Cl-i-Pr | H | H | 2-Me, 4-Me | —CH$_2$— | —CH$_2$— | — | |
| 472 | NH$_2$ | MeO-i-Pr | H | H | 2-Me, 4-Me | —CH$_2$— | —CH$_2$— | — | |
| 473 | NH$_2$ | 1-HO—Et | H | H | 2-Me, 4-Me | —CH$_2$— | —CH$_2$— | — | |
| 474 | NH$_2$ | 1-MeO—Et | H | H | 2-Me, 4-Me | —CH$_2$— | —CH$_2$— | — | |
| 475 | NH$_2$ | 1-F—Et | H | H | 2-Me, 4-Me | —CH$_2$— | —CH$_2$— | — | |
| 476 | NH$_2$ | 1-Cl—Et | H | H | 2-Me, 4-Me | —CH$_2$— | —CH$_2$— | — | |
| 477 | NH$_2$ | 1-AcO—Et | H | H | 2-Me, 4-Me | —CH$_2$— | —CH$_2$— | — | |
| 478 | NH$_2$ | HO-i-Pr | H | H | 1-Me, 4-Me | —CH$_2$— | —CH$_2$— | — | |
| 479 | NH$_2$ | Cl-i-Pr | H | H | 3-Me, 4-Me | —CH$_2$— | —CH$_2$— | — | |
| 480 | NH$_2$ | CF$_3$ | H | H | H | — | —CH$_2$—CHPh— | —O— | |
| 481 | NH$_2$ | CF$_2$CF$_2$H | H | H | H | — | —CH$_2$—CHPh— | —O— | |

TABLE 1-continued

Compounds of the formula (I')

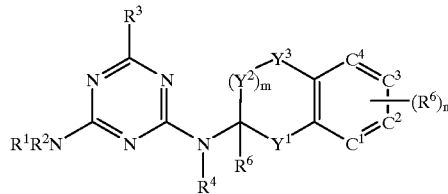

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 482 | NH$_2$ | F-i-Pr | H | H | 1-Me, 4-Me | — | —CH$_2$—CHPh— | —O— | |
| 483 | NH$_2$ | CF$_3$ | H | H | H | — | —CH$_2$—CHPh— | —S— | |
| 484 | NH$_2$ | CF$_2$CF$_2$H | H | H | 1-Me, 4-Me | — | —CH$_2$—CHPh— | —S— | |
| 485 | NH$_2$ | F-i-Pr | H | Me | 2-Me, 4-Me | — | —CH$_2$—CHPh— | —S— | |
| 486 | NH$_2$ | t-Bu | H | H | H | — | —CH$_2$—CHPh— | —O— | |
| 487 | NH$_2$ | CF$_2$CF$_2$H | H | Me | 2-Me, 4-Me | — | —CH$_2$—CHPh— | —O— | |
| 488 | NH$_2$ | F-i-Pr | H | H | 2-Me | — | —CH$_2$—CHPh— | —O— | |
| 489 | NHAC | CF$_3$ | H | H | H | — | —CH$_2$—CHPh— | —O— | |
| 490 | NEt2 | CFClCF$_2$H | H | H | H | — | —CH$_2$—CHPh— | —O— | |
| 491 | NH$_2$ | F-i-Pr | H | Ac | H | — | —CH$_2$—CHPh— | —O— | |
| 492 | NH$_2$ | Me | H | H | H | — | —CH$_2$—CHPh— | —O— | |
| 493 | NH$_2$ | CF$_2$CF$_3$ | H | H | H | — | —CH$_2$—CHPh— | —O— | |
| 494 | NH$_2$ | Et | H | H | H | — | —CH$_2$—CHPh— | —O— | |
| 495 | NH$_2$ | CF$_2$Me | H | H | H | — | —CH$_2$—CHPh— | —O— | |
| 496 | NH$_2$ | CF$_2$CF$_2$H | 4-Cl-Bz | H | H | — | —CH$_2$—CHPh— | —O— | |
| 497 | NH$_2$ | F-i-Pr | H | Et | H | — | —CH$_2$—CHPh— | —O— | |
| 498 | NH$_2$ | CCl$_3$ | H | H | H | — | —CH$_2$—CHPh— | —O— | |
| 499 | NH$_2$ | CF$_2$Ph | H | H | H | — | —CH$_2$—CHPh— | —O— | |
| 500 | NH$_2$ | CH$_2$COOMe | H | H | H | — | —CH$_2$—CHPh— | —O— | |
| 501 | NH$_2$ | CH$_2$CN | H | H | H | — | —CH$_2$—CHPh— | —O— | |
| 502 | NH$_2$ | CHMeCN | H | H | H | — | —CH$_2$—CHPh— | —O— | |
| 503 | NH$_2$ | 1-OMe—Et | H | H | H | — | —CH$_2$—CHPh— | —O— | |
| 504 | NH$_2$ | 2-F—Ph | H | H | H | — | —CH$_2$—CHPh— | —O— | |
| 505 | NH$_2$ | 3-F—Ph | H | H | H | — | —CH$_2$—CHPh— | —O— | |
| 506 | NH$_2$ | 4-F—Ph | H | H | H | — | —CH$_2$—CHPh— | —O— | |
| 507 | NH$_2$ | 2-Me—Ph | H | H | H | — | —CH$_2$—CHPh— | —O— | |
| 508 | NH$_2$ | 2-Et—Ph | H | H | H | — | —CH$_2$—CHPh— | —O— | |
| 509 | NH$_2$ | 2-OH—Ph | H | H | H | — | —CH$_2$—CHPh— | —O— | |
| 510 | NH$_2$ | 2-OMe—Ph | H | H | H | — | —CH$_2$—CHPh— | —O— | |
| 511 | NH$_2$ | 2-CN—Ph | H | H | H | — | —CH$_2$—CHPh— | —O— | |
| 512 | NH$_2$ | 2,4-F$_2$—Ph | H | H | H | — | —CH$_2$—CHPh— | —O— | |
| 513 | NH$_2$ | 1-Me-c-Pr | H | H | H | — | —CH$_2$—CHPh— | —O— | |
| 514 | NH$_2$ | epoxid | H | H | H | — | —CH$_2$—CHPh— | —O— | |
| 515 | NH$_2$ | 1-Me-epoxid | H | H | H | — | —CH$_2$—CHPh— | —O— | |
| 516 | NH$_2$ | 1,2-Me$_2$-epoxid | H | H | H | — | —CH$_2$—CHPh— | —O— | |
| 517 | NH$_2$ | 1,2,2-Me$_3$-epoxid | H | H | H | — | —CH$_2$—CHPh— | —O— | |
| 518 | NH$_2$ | 1-Me-2-Et-epoxid | H | H | H | — | —CH$_2$—CHPh— | —O— | |
| 519 | NH$_2$ | 1-Me-2-n-Bu-epoxid | H | H | H | — | —CH$_2$—CHPh— | —O— | |
| 520 | NH$_2$ | 2-Me-epoxid | H | H | H | — | —CH$_2$—CHPh— | —O— | |
| 521 | NH$_2$ | t1 | H | H | H | — | —CH$_2$—CHPh— | —O— | |
| 522 | NH$_2$ | HO-i-Pr | H | H | H | — | —CH$_2$—CHPh— | —O— | |
| 523 | NH$_2$ | Cl-i-Pr | H | H | H | — | —CH$_2$—CHPh— | —O— | |
| 524 | NH$_2$ | MeO-i-Pr | H | H | H | — | —CH$_2$—CHPh— | —O— | |
| 525 | NH$_2$ | 1-HO—Et | H | H | H | — | —CH$_2$—CHPh— | —O— | |
| 526 | NH$_2$ | 1-MeO—Et | H | H | H | — | —CH$_2$—CHPh— | —O— | |
| 527 | NH$_2$ | 1-F—Et | H | H | H | — | —CH$_2$—CHPh— | —O— | |
| 528 | NH$_2$ | 1-Cl—Et | H | H | H | — | —CH$_2$—CHPh— | —O— | |
| 529 | NH$_2$ | 1-AcO—Et | H | H | H | — | —CH$_2$—CHPh— | —O— | |
| 530 | NMe$_2$ | HO-i-Pr | H | H | H | — | —CH$_2$—CHPh— | —O— | |
| 531 | NHBz | Cl-i-Pr | H | H | H | — | —CH$_2$—CHPh— | —O— | |
| 532 | NH$_2$ | CF$_3$ | H | H | H | — | —CH$_2$—CH$_2$— | —CH$_2$— | |
| 533 | NH$_2$ | CF$_2$CF$_2$H | H | H | H | — | —CH$_2$—CH$_2$— | —CH$_2$— | |
| 534 | NH$_2$ | F-i-Pr | H | H | H | — | —CH$_2$—CH$_2$— | —CH$_2$— | |
| 535 | NH$_2$ | CF$_3$ | H | H | 2-thien-2-yl | — | —CH$_2$—CH$_2$— | —CH$_2$— | |
| 536a | NH$_2$ | CF$_2$CF$_2$H | Me | H | 2-Me, 4-Me | — | —CH$_2$—CH$_2$— | —CH$_2$— | |
| 537 | NH$_2$ | F-i-Pr | H | Me | 2-Me, 4-Me | — | —CH$_2$—CH$_2$— | —CH$_2$— | |
| 538a | NH$_2$ | t-Bu | Me | H | H | — | —CH$_2$—CH$_2$— | —CH$_2$— | |
| 539 | NH$_2$ | CF$_2$CF$_2$H | H | Me | 2-Me, 3-Me | — | —CH$_2$—CH$_2$— | —CH$_2$— | |
| 540 | NH$_2$ | F-i-Pr | H | H | 2-Me, | — | —CH$_2$—CH$_2$— | —CH$_2$— | |
| 541a | NH$_2$ | CF$_3$ | H | H | 2-Me, 4-Me | — | —CH$_2$—CH$_2$— | —CHPh— | |

TABLE 1-continued

Compounds of the formula (I')

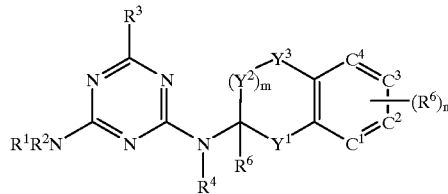

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 542 | NH$_2$ | CFClCF$_2$H | H | H | H | — | —CH$_2$—CH$_2$— | —CH$_2$— | |
| 543 | NH$_2$ | F-i-Pr | H | Ac | 3-OMe | — | —CH$_2$—CH$_2$— | —CH$_2$— | |
| 544 | NH$_2$ | Me | H | H | H | — | —CH$_2$—CH$_2$— | —CH$_2$— | |
| 545 | NH$_2$ | CF$_2$CF$_3$ | H | H | H | — | —CH$_2$—CH$_2$— | —CH$_2$— | |
| 546 | NH$_2$ | Et | H | H | H | — | —CH$_2$—CH$_2$— | —CH$_2$— | |
| 547 | NH$_2$ | CF$_2$Me | H | H | H | — | —CH$_2$—CH$_2$— | —CH$_2$— | |
| 548 | NH$_2$ | CF$_2$CF$_2$H | H | H | 1-Me, 4-Me | — | —CH$_2$—CH$_2$— | —CH$_2$— | |
| 549 | NH$_2$ | F-i-Pr | H | Et | 1-Me, 4-Me | — | —CH$_2$—CH$_2$— | —CH$_2$— | |
| 550 | NH$_2$ | CCl$_3$ | H | H | H | — | —CH$_2$—CH$_2$— | —CH$_2$— | |
| 551 | NH$_2$ | CF$_2$Ph | H | H | H | — | —CH$_2$—CH$_2$— | —CH$_2$— | |
| 552 | NH$_2$ | CH$_2$COOMe | H | H | H | — | —CH$_2$—CH$_2$— | —CH$_2$— | |
| 553 | NH$_2$ | CH$_2$CN | H | H | H | — | —CH$_2$—CH$_2$— | —CH$_2$— | |
| 554 | NH$_2$ | CHMeCN | H | H | H | — | —CH$_2$—CH$_2$— | —CH$_2$— | |
| 555 | NH$_2$ | 1-OMe—Et | H | H | H | — | —CH$_2$—CH$_2$— | —CH$_2$— | |
| 556 | NH$_2$ | 2-F—Ph | H | H | H | — | —CH$_2$—CH$_2$— | —CH$_2$— | |
| 557 | NH$_2$ | 3-F—Ph | H | H | H | — | —CH$_2$—CH$_2$— | —CH$_2$— | |
| 558 | NH$_2$ | 4-F—Ph | H | H | H | — | —CH$_2$—CH$_2$— | —CH$_2$— | |
| 559 | NH$_2$ | 2-Me—Ph | H | H | H | — | —CH$_2$—CH$_2$— | —CH$_2$— | |
| 560 | NH$_2$ | 2-Et—Ph | H | H | H | — | —CH$_2$—CH$_2$— | —CH$_2$— | |
| 561 | NH$_2$ | 2-OH—Ph | H | H | H | — | —CH$_2$—CH$_2$— | —CH$_2$— | |
| 562 | NH$_2$ | 2-OMe—Ph | H | H | H | — | —CH$_2$—CH$_2$— | —CH$_2$— | |
| 563 | NH$_2$ | 2-CN—Ph | H | H | H | — | —CH$_2$—CH$_2$— | —CH$_2$— | |
| 564 | NH$_2$ | 2-F4-F—Ph | H | H | H | — | —CH$_2$—CH$_2$— | —CH$_2$— | |
| 565 | NH$_2$ | 1-Me-c-Pr | H | H | H | — | —CH$_2$—CH$_2$— | —CH$_2$— | |
| 566 | NH$_2$ | epoxid | H | H | H | — | —CH$_2$—CH$_2$— | —CH$_2$— | |
| 567 | NH$_2$ | 1-Me-epoxid | H | H | H | — | —CH$_2$—CH$_2$— | —CH$_2$— | |
| 568 | NH$_2$ | 1,2-Me$_2$-epoxid | H | H | H | — | —CH$_2$—CH$_2$— | —CH$_2$— | |
| 569 | NH$_2$ | 1,2,2-Me$_3$-epoxid | H | H | H | — | —CH$_2$—CH$_2$— | —CH$_2$— | |
| 570 | NH$_2$ | 1-Me-2-Et-epoxid | H | H | H | — | —CH$_2$—CH$_2$— | —CH$_2$— | |
| 571 | NH$_2$ | 1-Me-2-n-Bu-epoxid | H | H | H | — | —CH$_2$—CH$_2$— | —CH$_2$— | |
| 572 | NH$_2$ | 2-Me-epoxid | H | H | H | — | —CH$_2$—CH$_2$— | —CH$_2$— | |
| 573 | NH$_2$ | t1 | H | H | H | — | —CH$_2$—CH$_2$— | —CH$_2$— | |
| 574 | NH$_2$ | HO-i-Pr | H | H | H | — | —CH$_2$—CH$_2$— | —CH$_2$— | |
| 575 | NH$_2$ | Cl-i-Pr | H | H | H | — | —CH$_2$—CH$_2$— | —CH$_2$— | |
| 576 | NH$_2$ | MeO-i-Pr | H | H | H | — | —CH$_2$—CH$_2$— | —CH$_2$— | |
| 577 | NH$_2$ | 1-HO—Et | H | H | H | — | —CH$_2$—CH$_2$— | —CH$_2$— | |
| 578 | NH$_2$ | 1-MeO—Et | H | H | H | — | —CH$_2$—CH$_2$— | —CH$_2$— | |
| 579 | NH$_2$ | 1-F—Et | H | H | H | — | —CH$_2$—CH$_2$— | —CH$_2$— | |
| 580 | NH$_2$ | 1-Cl—Et | H | H | H | — | —CH$_2$—CH$_2$— | —CH$_2$— | |
| 581 | NH$_2$ | 1-AcO—Et | H | H | H | — | —CH$_2$—CH$_2$— | —CH$_2$— | |
| 582 | NH$_2$ | HO-i-Pr | H | H | H | CO | —CH$_2$—CH$_2$— | —CH$_2$— | |
| 583 | NH$_2$ | Cl-i-Pr | H | H | H | CO | —CH$_2$—CH$_2$— | —CH$_2$— | |
| 584 | NH$_2$ | 1-OH-2-MeO—Et | H | H | 2-Me-4-Me | — | CH$_2$—CH$_2$— | —CH$_2$— | |
| 585 | NH$_2$ | CF$_3$ | H | H | 3-MeO, 4-F | — | —CH$_2$CH$_2$— | —CH$_2$— | |
| 586 | NH$_2$ | CF$_3$ | H | H | 1-Me, 4-Me | — | —CH$_2$CH$_2$— | S | 176–178 |
| 587 | NH$_2$ | i-Pr | H | H | 2-Me, 4-Me | — | —CH$_2$CH$_2$— | —CH$_2$— | fest |
| 588 | NH$_2$ | CH$_2$CH(OH)—CF$_3$H | H | H | 2-Me, 4-Me | — | — | —CH$_2$— | fest |
| 589 | NH$_2$ | —CMe═CH$_2$ | H | H | 2-Me, 4-Me | — | —CH$_2$—CH$_2$— | —CH$_2$— | 156–157 |
| 590 | NH$_2$ | Me | H | H | 2-Me, 4-Me | — | —CH$_2$—CH$_2$— | —CH$_2$— | 100–101 |
| 591 | NH$_2$ | CH$_2$—CMe$_2$OMe | H | H | 2-Me, 4-Me | — | —CH$_2$—CH$_2$— | —CH$_2$— | fest |
| 592 | NH$_2$ | CH$_2$—OMe | H | H | 2-Me, 4-Me | — | —CH$_2$—CH$_2$— | —CH$_2$— | 198–199 |
| 593 | NH$_2$ | CH$_2$-t-Bu | H | H | 2-Me, 4-Me | — | —CH$_2$—CH$_2$— | —CH$_2$— | |
| 594 | NH$_2$ | NH$_2$ | H | H | 2-Me, 4-Me | — | —CH$_2$—CH$_2$— | —CH$_2$— | |
| 595 | NH$_2$ | OMe | H | H | 2-Me, 4-Me | — | —CH$_2$—CH$_2$— | —CH$_2$— | 180–182 |
| 596 | NH$_2$ | SMe | H | H | 2-Me, 4-Me | — | —CH$_2$—CH$_2$— | —CH$_2$— | |
| 597 | NH$_2$ | SEt | H | H | 2-Me, 4-Me | — | —CH$_2$—CH$_2$— | —CH$_2$— | |
| 598 | NH$_2$ | 1-F-c-Pr | H | H | 2-Me, 4-Me | — | —CH$_2$—CH$_2$— | —CH$_2$— | 65–70 |

TABLE 1-continued

Compounds of the formula (I')

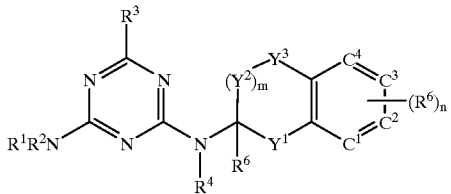

(I')

| No. | NR$^1$R$^2$ | R$^3$ | R$^4$ | R$^5$ | (R$^6$)$_n$ | Y$^1$ | (Y$^2$)$_m$ | Y$^3$ | Fp. (° C.) |
|---|---|---|---|---|---|---|---|---|---|
| 599 | NH$_2$ | CH$_2$CH(OMe)—CF$_3$ | H | H | 2-Me, 4-Me | — | —CH$_2$—CH$_2$— | —CH$_2$— | |
| 600 | NH$_2$ | CH$_2$CH(OMe)—CF$_3$ | H | H | 2-Me, 4-Me | — | —CH$_2$CH$_2$— | — | fest |
| 601 | NH$_2$ | 1-F-i-Pr | H | H | H | — | —CH$_2$—CH$_2$— | —O— | 191–193 |
| 602 | NH$_2$ | CHCF$_3$CH$_2$OMe | H | H | 2-Me, 4-Me | — | —CH$_2$—CH$_2$— | —CH$_2$— | |
| 603 | NH$_2$ | CHMeCH$_2$OMe | H | H | 2-Me, 4-Me | — | —CH$_2$—CH$_2$— | —CH$_2$— | |
| 604 | NH$_2$ | 1-Me-c-Bu | H | H | H | — | —CH$_2$—CH$_2$— | — | 148–150 |
| 605 | NH$_2$ | 1-Me-c-Bu | H | H | 2-Me, 4-Me | — | —CH$_2$—CH$_2$— | —CH$_2$— | fest |
| 606 | NH$_2$ | CH$_2$CH$_2$CF$_3$ | H | H | 2-Me, 4-Me | — | —CH$_2$—CH$_2$— | —CH$_2$— | 55–60 |
| 607 | NH$_2$ | CHMeCH$_2$CF$_3$ | H | H | 2-Me, 4-Me | — | —CH$_2$—CH$_2$— | —CH$_2$— | fest |
| 608 | NH$_2$ | CMe=CHCF$_3$ | H | H | 2-Me, 4-Me | — | —CH$_2$—CH$_2$— | —CH$_2$— | fest |
| 609 | NH$_2$ | CH$_2$CH$_2$CF$_3$ | H | H | H | — | —CH$_2$—CH$_2$— | — | 86–90 |
| 610 | NH$_2$ | 1-F-i-Pr | H | H | 2-F | — | —CH$_2$—CH$_2$ | —S— | 149–150 |
| 611 | NH$_2$ | C(OH)Et$_2$ | H | H | 2-Me, 4-Me | — | —CH$_2$—CH$_2$— | —CH$_2$— | fest |
| 612 | NH$_2$ | 1-F-c-Pr | H | H | 2-Me, 4-Me | — | —CH$_2$—CH$_2$— | —O— | 215–220 |
| 613 | NH$_2$ | 2,2,3,3-Me$_4$-c-Pr | H | H | 2-Me, 4-Me | — | —CH$_2$—CH$_2$— | —CH$_2$— | |
| 614 | NH$_2$ | 1-Et-c-Bu | H | H | 2-Me, 4-Me | — | —CH$_2$—CH$_2$— | —CH$_2$— | |
| 615 | NH$_2$ | F-i-Pr | H | H | H | — | —CH$_2$— | —CHPh— | 93–95 |
| 616 | NH$_2$ | F-i-Pr | H | H | 1-Me, 3-Me | — | —CH$_2$—CH$_2$— | —O— | 214–216 |
| 617 | NH$_2$ | F-i-Pr | H | H | 4-Me | — | —CH$_2$—CH$_2$— | — | 140–144 |
| 618 | NH$_2$ | CHOHPh | H | H | H | — | —CH$_2$—CH$_2$— | — | |
| 619 | NH$_2$ | CHOHPh | H | H | 2-Me, 4-Me | — | —CH$_2$—CH$_2$— | —CH$_2$— | |
| 620 | NH$_2$ | CH$_2$OMe | H | H | H | — | —CH$_2$—CH$_2$— | — | 197–198 |
| 621 | NH$_2$ | CH$_2$OMe | H | H | 2-Me, 4-Me | — | —CH$_2$—CH$_2$— | —O— | 180–182 |
| 622 | NH$_2$ | CH$_2$CH$_2$—CH=CH$_2$ | H | H | 2-Me, 4-Me | — | —CH$_2$—CH$_2$— | —CH$_2$ | fest |
| 623 | NH$_2$ | CH(OMe)Ph | H | H | 2-Me, 4-Me | — | —CH$_2$—CH$_2$— | —CH$_2$— | fest |
| 624 | NH$_2$ | CH$_2$-c-Pr | H | H | 2-Me, 4-Me | — | —CH$_2$—CH$_2$— | —CH$_2$— | fest |
| 625 | NH$_2$ | -5-Isoxazolyl | H | H | 2-Me, 4-Me | — | —CH$_2$—CH$_2$— | —CH$_2$— | fest |
| 626 | NH$_2$ | i-Pr | H | H | 2-Me, 4-Me | — | —CH$_2$—CH$_2$— | — | fest |
| 627 | NH$_2$ | NMe$_2$ | H | H | 2-Me, 4-Me | — | —CH$_2$—CH$_2$— | —CH$_2$— | 155–160 |
| 628 | NMePh | F | H | H | 2-Me, 4-Me | — | —CH$_2$—CH$_2$— | —CH$_2$— | 146–148 |
| 629 | NH$_2$ | 1-F-i-Pr | H | H | 2-Me, 4-Me | — | —CH(3,5-Me$_2$—Bz) | —CH$_2$— | fest |
| 630 | NH$_2$ | i-Pr | H | H | H | — | —CH$_2$—CH$_2$— | — | 173–175 |
| 631 | NH$_2$ | 1-F-i-Pr | H | H | 2-MeO | — | —CH$_2$—CH$_2$— | —CH$_2$— | 172–173 |
| 632 | NH$_2$ | 1-F-i-Pr | H | H | 4-MeO, 2F | — | —CH$_2$—CH$_2$— | —CH$_2$— | |
| 633 | NH$_2$ | CF$_3$ | H | H | 4-MeO, 2F | — | —CH$_2$—CH$_2$— | —CH$_2$— | |
| 634 | NH$_2$ | c-Pr | H | H | 4-MeO | — | —CH$_2$—CH$_2$— | —CH$_2$— | 89–94 |
| 635 | NH$_2$ | CH$_2$OMe | H | H | 4-MeO | — | —CH$_2$—CH$_2$— | —CH$_2$— | 158–160 |
| 636 | NH$_2$ | Et | H | H | H | — | —CH$_2$—CH$_2$— | — | 175–178 |
| 637 | NH$_2$ | Et | H | H | 2-Me, 4-Me | — | —CH$_2$—CH$_2$— | —CH$_2$— | 76–80 |
| 638 | NH$_2$ | CHOME-i-Pr | H | H | 2-Me, 4-Me | — | —CH$_2$—CH$_2$— | — | fest |
| 639 | NH$_2$ | CH$_2$Bz | H | H | H | — | —CH$_2$—CH$_2$— | — | 96–98 |
| 640 | NH$_2$ | CH$_2$Bz | H | H | 2-Me, 4-Me | — | —CH$_2$—CH$_2$— | —CH$_2$— | 70–74 |
| 641 | NH$_2$ | 1-F-i-Pr | H | H | 1-Me, 3-Me | — | —CH$_2$—CH$_2$— | — | |
| 642 | NH$_2$ | CF$_3$ | H | H | 1-Me, 3-Me | — | —CH$_2$—CH$_2$— | — | |
| 643 | NH$_2$ | n-Pr | H | H | 2-Me, 4-Me | — | —CH$_2$—CH$_2$— | —CH$_2$— | 75–77 |
| 644 | NH$_2$ | n-Pentyl | H | H | 2-Me, 4-Me | — | —CH$_2$—CH$_2$— | —CH$_2$— | 62–64 |
| 645 | NH$_2$ | c-Pr | H | H | H | — | —CH$_2$—CH$_2$— | — | |
| 646 | NH$_2$ | 1-F-i-Pr | H | H | 2-F | — | —CH$_2$—CH$_2$— | — | |
| 647 | NH$_2$ | Cl | H | H | 2-Me, 4-Me | — | —CH$_2$—CH$_2$— | —CH$_2$— | 225–226 |
| 648 | NH$_2$ | CH$_2$—CH=CH$_2$ | H | H | 2-Me, 4-Me | — | —CH$_2$—CH$_2$— | —CH$_2$— | |
| 649 | NH$_2$ | NMe$_2$ | H | H | H | — | —CH$_2$—CH$_2$— | — | 173–174 |
| 650 | NH$_2$ | OCH$_2$CCH | H | H | 2-Me, 4-Me | — | —CH$_2$—CH$_2$— | — | |
| 651 | NH$_2$ | 1-EtO—Et | H | H | 2-Me, 4-Me | — | —CH$_2$—CH$_2$— | —CH$_2$— | |
| 652 | NH$_2$ | CH$_2$-c-i-Pr | H | H | 2-Me, 4-Me | — | —CH$_2$—CH$_2$— | —CH$_2$— | 78–80 |
| 653 | NH$_2$ | CH$_2$-c-i-Pr | H | H | H | — | —CH$_2$—CH$_2$— | — | 65–67 |
| 654 | NH$_2$ | CH$_2$-c-Hexyl | H | H | H | — | —CH$_2$—CH$_2$— | — | 70–75 |
| 655 | NH$_2$ | CH$_2$-c-Hexyl | H | H | 2-Me, 4-Me | — | —CH$_2$—CH$_2$— | —CH$_2$— | 75–80 |
| 656 | NH$_2$ | i-Pr | H | H | 3-Me, 4-Me | — | —CH$_2$—CH$_2$— | — | 190–191 |

TABLE 1-continued

Compounds of the formula (I')

(I')

$$\text{R}^1\text{R}^2\text{N}-\underset{\underset{\text{N}}{\parallel}}{\text{C}}\underset{\text{N}}{\overset{\text{R}^3}{\underset{\parallel}{\text{C}}}}\text{N}-\underset{\text{R}^4}{\text{N}}-\underset{\text{R}^6}{\overset{(\text{Y}^2)_m}{\text{C}}}\text{Y}^1-\underset{\text{C}^2}{\overset{\text{Y}^3-\text{C}^4}{\overset{\parallel}{\text{C}^3}}}(\text{R}^6)_n$$

| No. | NR¹R² | R³ | R⁴ | R⁵ | (R⁶)ₙ | Y¹ | (Y²)ₘ | Y³ | Fp. (° C.) |
|---|---|---|---|---|---|---|---|---|---|
| 657 | NH₂ | i-Pr | H | H | 4-Me | — | —CH₂—CH₂— | — | 60–65 |
| 658 | NH₂ | F-i-Pr | H | H | H | — | —CH₂—CHPh— | —O— | 104–105 |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable power which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of alkylphenyl polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Granules which are dispersible in water are obtained by mixing
- 75 parts by weight of a compound of the formula (I),
- 10 parts by weight of calcium lignosulfonate,
- 5 parts by weight of sodium lauryl sulfate,
- 3 parts by weight of polyvinyl alcohol and
- 7 parts by weight of kaolin, grinding the mixture on a pinned-disk mill and granulating the powder in a fluidized bed by spraying on water as granulation liquid.

f) Water-dispersible granules are also obtained by homogenizing, on a colloid mill,
- 25 parts by weight of a compound of the formula (I),
- 5 parts by weight of sodium 2,2'-dinaphthylmethane-6,6'-disulfonate,
- 2 parts by weight of sodium oleoylmethyltaurate,
- 1 part by weight pf polyvinyl alcohol,
- 17 parts by weight of calcium carbonate and
- 50 parts by weight of water, precomminuting the mixture, subsequently grinding it on a bead mill and atomizing and drying the resulting suspension is a spray tower by means of a single-substance nozzle.

C. BIOLOGICAL EXAMPLES

1. Pre-emergence Effect in Weeds

Seeds or rhizome pieces of monocotyledonous and dicotyledonous weed plants are placed in sandy loam soil in plastic pots and covered with soil. The compounds according to the invention which were formulated in the form of wettable powders or emulsion concentrates are then applied to the surface of the soil cover in the form of aqueous suspensions or emulsions at an application rate of 600 to 800 l of water/ha (converted), in various dosages. After the treatment, the pots are placed in a greenhouse and kept under good growth conditions for the weeds. After the test plants have emerged, the damage to the plants or the negative effect on the emergence is scored visually by comparison with untreated controls. As shown by the test results, the compounds according to the invention have a good herbicidal pre-emergence activity against a broad spectrum of grass weeds and broad-leaved weeds. For example, Examples No. 2, 3, 38, 43, 199, 200, 231, 240, 482 (see Table 1) show a very good herbicidal activity in the test against harmful plants such as *Sinapis alba, Chrysanthemum segetum, Avena sativa, Stellaria media, Echinochloa crus-galli, Lolium multiflorum*, Setaria spp., *Abutilon theophrasti, Amaranthus retroflexus* and *Panicum miliaceum* when applied pre-emergence at a rate of application of 0.5 kg and less of active ingredient per hectare.

2. Post-emergence Effect on Weeds

Seeds or rhizome pieces of monocotyledonous and dicotyledonous weeds are placed in sandy loam soil in plastic pots, covered with soil and grown in a greenhouse under good growth conditions. Three weeks after sowing, the test plants are treated in the three-leaf stage. The compounds according to the invention which are formulated as wettable powders or as emulsion concentrates are sprayed in various dosages onto the green parts of the plants at an application rate of 600 to 800 l of water/ha (converted). After the test plants have remained in the greenhouse for about 3 to 4 weeks under ideal growth conditions, the effect of the preparations is scored visually by comparison with untreated controls. The agents according to the invention also have a good herbicidal post-emergence activity against a broad range of economically important grass weeds and broad-leaved weeds. For example, Examples No. 2, 3, 38, 43, 199, 200, 231, 240, 482 (see Table 1) show a very good herbicidal activity in the test against harmful plants such as *Sinapis alba, Echinochloa crus-galli, Lolium multiflorum, Chrysanthemum segetum*, Setaria spp., *Abutilon theophrasti, Amaranthus retroflexus, Panicum miliaceum* and *Avena*

*sativa* when applied post-emergence at an application rate of 0.5 kg and less of active ingredient per hectare.

3. Activity Against Harmful Plants in Rice

Transplanted and sown rice and weeds typically found in rice, are grown in the greenhouse until they have reached the three-leaf stage (Echinochloa 1.5 leaves) under paddy rice conditions (level of flooding of water: 2–3 cm) in closed plastic pots. They are then treated with the compounds according to the invention. To this end, the formulated active substances are suspended, dissolved or emulsified in water and applied by pouring into the flooding water of the test plants at various dosages. After this treatment, the test plants are placed in a greenhouse under ideal growth conditions and kept like this during the entire test period. Approximately three weeks after application, they are evaluated by means of visually scoring the damage to the plants in comparison with untreated controls, and a very good herbicidal activity against harmful plants which are typical for rice crops is shown, for example, by Compounds No. 2, 3, 38, 43, 199, 200, 231, 240, 482 (see Table 1), for example *Cyperus monti, Echinochloa crus-galli, Eleocharis acicularis* and *Sagittaria pygmaea*.

4. Tolerance by Crop Plants

In further greenhouse experiments, seeds of a substantial number of crop plants and weeds are placed in sandy loam substrate and covered with soil. Some of the pots are treated immediately as described in Section 1, and the remaining pots are placed in a greenhouse until the plants have developed two to three true leaves and then sprayed with various dosages of the substances of the formula (I') according to the invention as described in Section 2. Visual scoring four to five weeks after application and after the plants had remained in the greenhouse revealed that the compounds according to the invention do not inflict any damage to dicotyledonous crops such as soy beans, cotton, oil seed rape, sugarbeet and potatoes when used pre- and post-emergence, even when high dosages of active substance are used. Moreover, some substances also leave Gramineae crops such as barley, wheat, rye, Sorghum species, maize or rice unharmed. Some of the compounds amongst, inter alia, Nos. 2, 3, 38, 43, 199, 200, 231, 240, 482 of Table 1 of the formula (I') have a high selectivity and are therefore suitable for controlling undesirable vegetation in agricultural crops.

We claim:

1. A compound of the formula (I) or a salt thereof

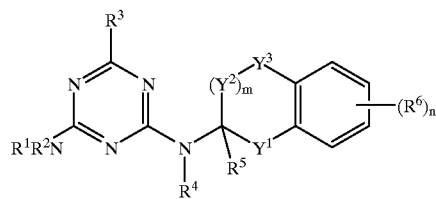

in which

R$^1$ and R$^2$ independently of one another are hydrogen, amino, alkylamino or dialkylamino having in each case 1 to 6 carbon atoms in the alkyl radical, an acyclic or cyclic hydrocarbon radical or hydrocarbon-oxy radical having in each case 1 to 10 carbon atoms or a heterocyclyl radical, heterocyclyloxy radical, heterocyclylthio radical or heterocyclylamino radical each of the five last mentioned radicals being unsubstituted or substituted, or are an acyl radical, the heterocyclyl in the radical having in each case 3 to 6 ring atoms and 1 hetero ring atom selected form the group consisting of N,O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, or R$^1$ and R$^2$ together with the nitrogen atom of the group NR$^1$R$^2$ are a saturated heterocyclic radical being unsubstituted or substituted, the heterocyclic radical having 3 to 6 ring atoms and 1 hetero ring atom selected from the group consisting of N, O and S, or the heterocyclic radical being selected from the group consisting of piperazinyl and morpholinyl, R$^3$ is halogen, cyano, thiocyanato, nitro or a radical of the formula —Z$^1$—R$^7$, R$^4$ is hydrogen, amino, alkylamino or dialkylarnino having in each case 1 to 6 carbon atoms in the alkyl radical, an acyclic or cyclic hydrocarbon radical or hydrocarbon-oxy radical having in each case 1 to 10 carbon atoms or a heterocyclyl radical, heterocyclyloxy radical or heterocyclylamino radical each of the five last mentioned radicals being unsubstituted or substituted, or are an acyl radical, the heterocyclyl in the radicals having in each case 3 to 6 ring atoms and 1 hetero ring atom selected form the group consisting of N, O, and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, R$^5$ is halogen, cyano, thiocyanato, nitro or a radical of the formula —Z$^2$—R$^8$, R$^6$, if n=1, or the radicals R$^6$ in each case independently of one another, if n is greater than 1, is, or are, halogen, cyano, thiocyanato, nitro or a group of the formula —Z$^3$—R$^9$, R$^7$, R$^8$ and R$^8$ in each case independently of one another are hydrogen or an acyclic hydrocarbon radical having 1 to 20 carbon atoms, it being possible for carbon atoms in the chain to be substituted by hetero atoms selected from the group consisting of N, O and S, or a cyclic hydrocarbon radical having 3 to 8 carbon atoms, or a heterocyclic radical having 3 to 9 ring atoms and 1 hetero ring atom selected from the group consisting of N, O and S, or a heterocyclic radical being selected from the group consisting of pyrimidinyl, pyridazinyl, pyrazinyl, thiazolyl, oxazolyl, pyrazolyl, imidazolyl, piperazinyl, dioxolanyl and morpholinyl, each of the acyclic hydrocarbon, cyclic hydrocarbon and heterocyclic radicals being unsubstituted or substituted, Z$^1$, Z$^2$, Z$^3$ in each case independently of one another are a direct bond or a divalent group of the formula —O—, —S(O)$_p$—, —S(O)$_p$—O—, —O—S(O)$_p$—, —CO—, —CS—, —S—CO—, —CO—S—, —O—CS—, —CS—O—, —S—CS—, —CS—S—, —O—CO—, —CO—O—, —NR'—, —O—NR'—, —NR'—O—, —NR'—CO— or —CO—NR'—, p being 0, 1 or 2 and R' being hydrogen, alkyl having 1 to 6 carbon atoms, phenyl, benzyl, cycloalkyl having 3 to 6 carbon atoms or alkanoyl having 1 to 6 carbon atoms, Y$^1$, Y$^2$, Y$^3$ and further groups Y$^2$, if m is 2, 3 or 4 are in each case independently of one another a divalent group of the formula CR$^a$R$^b$, R$^a$ and R$^b$ being identical or different and in each case a radical selected from the group consisting of the radicals which are possible for $R^7$ to $R^9$, or a divalent group of the formula —O—, —CO—, CS, —CH(OR*)—, C(=NR*)—, —S(O)q—, —NR*— or —N(O)—, q being 0, 1 or 2 and R* being hydrogen or alkyl having 1 to 4 carbon atoms, or $Y^1$ or $Y^3$ are a direct bond, two oxygen atoms of the groups $Y^2$ and $Y^3$ not being adjacent, m is 1, 2, 3 or 4, n is 0, 1, 2, 3 or 4.

2. A compound of the formula (I) as claimed in claim 1 or a salt thereof, wherein $R^1$ and $R^2$ in each case independently of one another are hydrogen, amino, alkylamino or dialkylamino having in each case 1 to 6 carbon atoms in the alkyl radical or an acyclic or cyclic hydrocarbon radical or hydrocarbon-oxy radical having in each case 1 to 6 carbon atoms or a heterocyclyl radical, heterocyclyloxy radical or heterocyclylamino radical, each of the five last mentioned radicals being unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy$]$carbonyl, $[(C_1-C_4)$alkyl$]$carbonyl, formyl, carbamoyl, mono and di-$[(C_1-C_4)$alkyl$]$aminocarbonyl, phenylcarbonyl, phenoxycarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl or substituted by an unsubstituted or substituted radical selected from the group consisting of phenyl, phenoxy, cycloalkyl, heterocyclyl and heterocyclyloxy, or an acyl radical, the heterocyclyl in the radicals having in each case 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, or $R^1$ and $R^2$ together with the nitrogen atom of the group $NR^1R^2$ are a saturated heterocyclic radical being unsubstituted or substituted by one or more radicals selected from the group consisting of halogen, $(C_1-C_4)$ alkyl and oxo, the heterocyclic radical having 3 to 6 ring atoms and 1 hetero ring atom selected from the group consisting of N, O, and S, or the heterocyclic radical being selected from the group consisting of piperazinyl and morpholinyl, $R^4$ is hydrogen, amino, alkylamino or dialkylamino having in each case 1 to 6 carbon atoms in the alkyl radical, an acyclic or cyclic hydrocarbon radical or hydrocarbon-oxy radical having in each case 1 to 6 carbon atoms or a heterocyclyl radical, heterocyclyloxy radical or heterocyclylamino radical, each of the five last-mentioned radicals being unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy$]$carbonyl, $[(C_1-C_4)$alkyl$]$carbonyl, formyl, carbamoyl, mono- and di-$[(C_1-C_4)$alkyl$]$aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl or substituted by an unsubstituted or substituted radical selected from the group consisting of phenyl, phenoxy, cycloalkyl, heterocyclyl and heterocyclyloxy, or an acyl radical, the heterocyclyl in the radicals having in each case 3 to 6 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^7$, $R^8$, $R^9$ in each case independently of one another are hydrogen or $(C_1-C_6)$alkyl, $(C_2-C_6)$alkenyl, $(C_2-C_6)$alkynyl, each of the last-mentioned 3 radicals being unsubstituted or substituted by one or more radicals selected from the group consisting of halogen, cyano, thiocyanato, nitro and radicals of the formula —$Z^4$—$R^{10}$, or $(C_3-C_8)$cycloalkyl which is unsubstituted or substituted by one or more radicals selected from the group consisting of halogen, $(C_1-C_6)$alkyl, $(C_1-C_6)$haloalkyl, $(C_1-C_6)$haloalkoxy, $(C_1-C_6)$alkoxy, $(C_1-C_6)$alkylthio, $(C_2-C_6)$alkenyl, $(C_2-C_6)$-alkynyl, $(C_3-C_4)$alkenyloxy and $(C_3-C_4)$alkynyloxy, or phenyl which is unsubstituted or substituted by one or more radicals selected from the group consisting of halogen, cyano, thiocyanato, nitro and radicals of the formula —$Z^5$—$R^{11}$, or a heterocyclic radical having 3 to 9 ring atoms and 1 hetero ring atom selected from the group consisting of N, O and S, or a heterocyclic radical being selected from the group consisting of pyrimidinyl, pyridazinyl, pyrazinyl, thiazolyl, oxazolyl, pyrazolyl, imidazolyl, piperazinyl, dioxolanyl and morpholinyl, the heterocyclic radical being unsubstituted or substituted by one or more radicals selected from the group consisting of halogen, cyano, thiocyanato, nitro and radicals of the formula —$Z^6R^{12}$, and $Z^1$, $Z^2$, $Z^3$, $Z^4$, $Z^5$, $Z^6$ in each case independently of one another are a direct bond or a divalent group of the formula —O—, —S(O)$_p$—, —S(O)$_p$—O—, —O—S(O)$_p$—, —CO—, —CS—, —S—CO—, —CO—S—, —O—CO—, —CO—O—, —NR'—, —O—NR'—, —NR'—O—, —NR'—CO— or —CO—NR'—, p being 0, 1 or 2 and R' being hydrogen, alkyl having 1 to 6 carbon atoms, phenyl, benzyl, cycloalkyl having 3 to 6 carbon atoms or alkanoyl having 1 to 6 carbon atoms, and $R^{10}$, $R^{11}$, $R^{12}$, in each case independently of one another are hydrogen, $(C_1-C_6)$ alkyl, $(C_2-C_6)$alkenyl, $(C_2-C_6)$alkynyl, each of the last-mentioned 3 radicals being unsubstituted or substituted by one or more radicals selected from the group consisting of halogen, $(C_1-C_4)$alkoxy and $(C_1-C_4)$alkylthio, or are $(C_3-C_8)$cycloalkyl, phenyl, heterocyclyl having 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, each of the cycloalkyl, phenyl or heterocyclyl radicals being unsubstituted or substituted, or
in each case two radicals —$Z^4$—$R^{10}$ or —$Z^5$—$R^{11}$ or —$Z^6$—$R^{12}$
together with the linkage element or the respective linkage elements are a cycle having 3 to 8 ring atoms which is carbocyclic or contains hetero ring atoms selected from the group consisting of O, S and N and which is unsubstituted or substituted by one or more radicals selected from the group consisting of halogen, ($C_1$–$C_4$) alkyl and oxo.

3. A compound of the formula (I) or a salt thereof as claimed in claim 1, wherein $R^1$, $R^2$ independently of one another are hydrogen, amino, formyl, aminocarbonyl, ($C_1$–$C_4$)alkyl, cyano($C_1$–$C_4$) alkyl, ($C_1$–$C_4$)alkylamino, di-[($C_1$–$C_4$)alkyl]amino, halo-($C_1$–$C_4$)alkyl, hydroxy-($C_1$–$C_4$)alkyl, ($C_1$–$C_4$) alkoxy-($C_1$–$C_4$)alkyl, halo($C_1$–$C_4$)alkoxy-($C_1$–$C_4$) alkyl, ($C_2$–$C_6$)alkenyl, ($C_2$–$C_6$)haloalkenyl, ($C_2$–$C_6$) alkynyl, ($C_2$–$C_6$)haloalkynyl, ($C_1$–$C_4$)alkylamino-($C_1$–$C_4$)alkyl, di-[($C_1$–$C_4$)alkyl]-amino-($C_1$–$C_4$)alkyl, ($C_3$–$C_9$)cycoalkylamino-($C_1$–$C_4$)alkyl, ($C_3$–$C_9$) cycloalkyl, heterocyclyl-($C_1$–$C_4$)alkyl, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$) alkylaminocarbonyl-($C_1$–$C_4$)alkyl, ($C_1$–$C_4$) alkylcarbonyl, ($C_1$–$C_4$)alkoxycarbonyl, mono- or di-[($C_1$–$C_4$)alkyl]aminocarbonyl, phenoxy($C_1$–$C_4$)alkyl, phenyl($C_1$–$C_4$)alkyl, heterocyclyl, heterocyclylarnino, heterocyclyloxy, heterocyclylthio, or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$)alkoxy, ($C_1$–$C_4$) alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, the heterocyclyl in the radicals having in each case 3 to 9 ring atoms and 1 hetero ring atoms selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^1$ and $R^2$ together with the nitrogen atom of the group $NR^1R^2$ are a saturated heterocyclic radical being unsubstituted or substituted by one or more radicals selected from the group consisting of halogen, ($C_1$–$C_4$) alkyl and oxo, the heterocyclic radical having 3 to 6 ring atoms and 1 hetero ring atom selected from the group consisting of N, O and S, or the heterocyclic radical being selected from the group consisting of piperazinyl and morpholinyl, $R^3$ is hydrogen, hydroxyl, amino, carboxyl, cyano, thiocyanato, formyl, aminocarbonyl, ($C_1$–$C_8$)alkyl, cyano-($C_1$–$C_4$)alkyl, ($C_1$–$C_4$)alkoxy, ($C_1$–$C_4$) alkylamino, di[($C_1$–$C_4$)alkyl]amino, halo-($C_1$–$C_4$) alkyl, hydroxy($C_1$–$C_4$)alkyl, ($C_1$–$C_4$)alkoxy-($C_1$–$C_4$) alkyl, halo-($C_1$–$C_4$)alkoxy-($C_1$–$C_4$)alkyl, ($C_1$–$C_4$) alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$) alkynyl, ($C_1$–$C_4$)alkylamino-($C_1$–$C_4$)alkyl, di[($C_1$–$C_4$) alkyl]-amino-($C_1$–$C_4$)alkyl, ($C_3$–$C_9$)cycloalkylamino-($C_1$–$C_4$)alkyl, ($C_3$–$C_9$)cycloalkyl, ($C_3$–$C_9$)cycloalkyl-($C_1$–$C_4$)alkyl, heterocyclyl-($C_1$–$C_4$)alkyl, the cyclic groups in the last-mentioned 4 radicals being unsubstituted or substituted by one or more radicals selected from the group consisting of ($C_1$–$C_4$)alkyl, halogen and cyano, or phenyl, phenylcarbonyl, phenoxycarbonyl, phenylcarbonyl-($C_1$–$C_4$)alkyl, ($C_1$–$C_4$) alkoxycarbonyl-($C_1$–$C_4$)alkyl, ($C_1$–$C_4$) alkylaminocarbonyl-($C_1$–$C_4$)alkyl, ($C_1$–$C_4$) alkylcarbonyl, ($C_1$–$C_4$)alkoxycarbonyl, mono- or di[($C_1$–$C_4$)alkyl]aminocarbonyl, phenoxy-($C_1$–$C_4$) alkyl, phenyl-($C_1$–$C_4$)alkyl, heterocyclyl, heterocyclylamino, heterocyclyloxy, heterocyclylthio or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$) alkoxy, ($C_1$–$C_4$)alkylthio, ($C_1$–$C_4$)haloalkyl, ($C_1$–$C_4$) haloalkoxy, formyl, ($C_1$–$C_4$)alkylcarbonyl, ($C_1$–$C_4$) alkoxycarbonyl and ($C_1$–$C_4$)alkoxy, the heterocyclyl in the radicals having in each case 3 to 9 ring atoms and I hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^4$ is hydrogen, amino, formyl, aminocarbonyl, ($C_1$–$C_4$) alkyl, cyano-($C_1$–$C_4$)alkyl, ($C_1$–$C_4$)alklylamino, di[($C_1$–$C_4$)alkyl]amino, halo-($C_1$–$C_4$)alkyl, hydroxy-($C_1$–$C_4$)alkyl, ($C_1$–$C_4$)alkoxy-($C_1$–$C_4$)alkyl, halo-($C_1$–$C_4$)alkoxy-($C_1$–$C_4$)alkyl, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di[($C_1$–$C_4$)alkyl] amino-($C_1$–$C_4$)alkyl, ($C_3$–$C_9$)cycloalkylamino-($C_1$–$C_4$)alkyl and ($C_3$–$C_9$)cycloalkyl, heterocyclyl-($C_1$–$C_4$)alkyl, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$) alkylcarbonyl, ($C_1$–$C_4$)alkoxycarbonyl, mono- or di[($C_1$–$C_4$)alkyl]aminocarbonyl, phenoxy($C_1$–$C_4$) alkyl, phenyl($C_1$–$C_4$)alkyl, heterocyclyl, heterocyclylamino, heterocyclyloxy, heterocyclylthio, or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$) alkoxy, ($C_1$–$C_4$)alkylthio, ($C_1$–$C_4$)haloalkyl, ($C_1$–$C_4$) haloalkoxy, formyl, ($C_1$–$C_4$)alkylcarbonyl, ($C_1$–$C_4$) alkoxycarbonyl, ($C_1$–$C_4$)alkoxy, the heterocyclyl in the radicals having in each case 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^5$ is hydrogen, formyl, carboxyl, cyano, thiocyanato, aminocarbonyl, ($C_1$–$C_4$)alkyl, cyano-($C_1$–$C_4$)alkyl, ($C_1$–$C_4$)alkoxy, ($C_1$–$C_4$)alkylamino, di[($C_1$–$C_4$)alkyl] amino, halo-($C_1$–$C_4$)alkyl, hydroxy-($C_1$–$C_4$)alkyl, ($C_1$–$C_4$)alkoxy-($C_1$–$C_4$)alkyl, halo-($C_1$–$C_4$)alkoxy-($C_1$–$C_4$)alkyl, ($C_1$–$C_4$)alkylthio, halo-($C_1$–$C_4$) alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$) alkylamino-($C_1$–$C_4$)alkyl, di[($C_1$–$C_4$)alkyl]amino- ($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, mono- or di[($C_1$–$C_4$)alkyl]aminocarbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, the heterocyclyl in the radicals having in each case 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^6$, if n is 1, and the radicals $R^6$, in each case independently of one another, when n is greater than 1, is, or are, halogen, hydroxyl, amino, nitro, formyl, carboxyl, cyano, thiocyanato, aminocarbonyl, ($C_1$–$C_4$)alkyl, cyano-($C_1$–$C_4$)alkyl, ($C_1$–$C_4$)alkoxy, ($C_1$–$C_4$)alkylamino, di[($C_1$–$C_4$)alkyl]amino, halo-($C_1$–$C_4$)alkyl, hydroxy-($C_1$–$C_4$)alkyl, ($C_1$–$C_4$)alkoxy-($C_1$–$C_4$)alkyl, halo-($C_1$–$C_4$)alkoxy-($C_1$–$C_4$)alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di[($C_1$–$C_4$)alkyl]amino-($C_1$–$C_4$)alkyl, ($C_3$–$C_9$)cycloalkylamino-($C_1$–$C_4$)alkyl, ($C_3$–$C_9$)cycloalkyl, heterocyclyl($C_1$–$C_4$)alkyl, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, mono- or di[($C_1$–$C_4$)alkyl]aminocarbonyl, phenoxy-($C_1$–$C_4$)alkyl, phenyl-($C_1$–$C_4$)alkyl, heterocyclyl, heterocyclylamino, heterocyclyloxy, heterocyclylthio or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, the heterocyclyl in the radicals having in each case 3 to 9 ring atoms and 1 hetero ring atom selected from the group consisting of N, O and S or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, or two adjacent radicals $R^6$ together being a fused cycle having 4 to 6 ring atoms which is carbocyclic or contains hetero ring atoms selected from the group consisting of O, S and N and which is unsubstituted or substituted by one or more radicals selected from the group consisting of halogen, ($C_1$–$C_4$)alkyl and oxo, $Y^1$, $Y^2$ and $Y^3$ and further groups $Y^2$ if m is 2, 3 or 4 in each case independently of one another are
  a divalent group of the formula $CR^aR^b$, $R^a$ and $R^b$ being identical or different and being in each case a radical as defined further below, or
  a divalent group of the formula —O—, —S—, —SO—, $SO_2$, —CO—, —CS—, —CH(OR*)—, —C(=NR*)—, —NR*— or —N(O)—, R* being hydrogen or alkyl having 1 to 4 carbon atoms, or
  $Y^1$ or $Y^3$ are a direct bond,
two oxygen atoms of the groups $Y^1$ to $Y^3$ not being adjacent,
  $R^a$, $R^b$ are hydrogen, formyl, carboxyl, cyano, thiocyanato, aminocarbonyl, ($C_1$–$C_4$)alkyl, cyano-($C_1$–$C_4$)alkyl, ($C_1$–$C_4$)alkoxy, ($C_1$–$C_4$)alkylamino, di[($C_1$–$C_4$)alkyl]amino, halo-($C_1$–$C_4$)alkyl, hydroxy-($C_1$–$C_4$)alkyl, ($C_1$–$C_4$)alkoxy-($C_1$–$C_4$)alkyl, halo-($C_1$–$C_4$)alkoxy-($C_1$–$C_4$)alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di[($C_1$–$C_4$)alkyl]amino-($C_1$–$C_4$)alkyl, ($C_3$–$C_9$)cycloalkylamino-($C_1$–$C_4$)alkyl, ($C_3$–$C_9$)cycloalkyl, heterocyclyl-($C_1$–$C_4$)alkyl, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, mono- or di[($C_1$–$C_4$)alkyl]aminocarbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, the heterocyclyl in the radicals having in each case 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, m is , 1, 2, 3 or 4, and n is 0, 1, 2, 3 or 4.

4. A compound of the formula (I) or a salt thereof as claimed in claim 1, wherein $R^1$, $R^2$ independently of one another are hydrogen, amino, formyl, ($C_1$–$C_4$)alkyl, ($C_1$–$C_4$)alkylcarbonyl, ($C_1$–$C_4$)alkoxycarbonyl or aminocarbonyl or $R^1$ and $R^2$ together with the nitrogen atom of the group $NR^1R^2$ are a saturated heterocyclic radical being unsubstituted or substituted by one or more radicals selected from the group consisting of halogen, ($C_1$–$C_4$)alkyl and oxo, the heterocyclic radical having 3 to 6 ring atoms and 1 hetero ring atom selected from the group consisting of N, O and S, or the heterocyclic radical being selected from the group consisting of piperazinyl and morpholinyl, $R^3$ is hydrogen, carboxyl, cyano, ($C_1$–$C_8$)alkyl, cyano ($C_1$–$C_4$)alkyl, halo-($C_1$–$C_4$)alkyl, hydroxy-($C_1$–$C_4$)

alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, $(C_3-C_9)$cycloalkyl-$(C_1-C_4)$alkyl, heterocyclyl-$(C_1-C_4)$alkyl, the cyclic groups being unsubstituted in the last-mentioned 4 radicals or substituted by one or more radicals selected from the group consisting of $(C_1-C_4)$alkyl and halogen, or phenyl, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, phenoxy $(C_1-C_4)$alkyl, phenyl$(C_1-C_4)$alkyl, heterocyclyl, or one of the last-mentioned 10 radicals which is substituted in the acyclic moiety or in the cyclic moiety by one or more radicals selected from the group consisting of halogen, nitro, $(C_1-C_4)$alkyl, $(C_1-C_4)$alkoxy, $(C_1-C_4)$haloalkyl, $(C_1-C_4)$alkylcarbonyl, $(C_1-C_4)$alkoxycarbonyl and $(C_1-C_4)$alkoxy, the heterocyclyl in the radicals having in each case 3 to 7 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^4$ is hydrogen, amino, formyl, aminocarbonyl, $(C_1-C_4)$alkyl, cyano-$(C_1-C_4)$alkyl, $(C_1-C_4)$alkylamino, $(C_1-C_4)$alkoxy-$(C_1-C_4)$alkyl, $(C_2-C_6)$alkenyl, halo-$(C_2-C_6)$alkenyl, $(C_2-C_6)$alkynyl, phenyl, $(C_1-C_4)$alkylcarbonyl, $(C_1-C_4)$alkoxycarbonyl, phenoxy-$(C_1-C_4)$alkyl, phenyl-$(C_1-C_4)$alkyl, or one of the last-mentioned 5 radicals which is substituted in the acyclic moiety or in the cyclic moiety by one or more radicals selected from the group consisting of halogen, $(C_1-C_4)$alkyl and $(C_1-C_4)$alkoxy, the heterocyclyl in the radicals having in each case 3 to 9 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^5$ is hydrogen, $(C_1-C_4)$alkyl, $(C_2-C_6)$alkenyl or $(C_2-C_6)$alkynyl, $R^6$, if n is 1, and the radicals $R^6$ in each case independently of one another, if n is greater than 1, is, or are, halogen, hydroxyl, amino, nitro, formyl, carboxyl, cyano, $(C_1-C_4)$alkyl, cyano-$(C_1-C_4)$alkyl, $(C_1-C_4)$alkoxy, $(C_1-C_4)$alkylamino, halo-$(C_1-C_4)$alkyl, hydroxy-$(C_1-C_4)$alkyl, $(C_1-C_4)$alkoxy-$(C_1-C_4)$alkyl, $(C_2-C_6)$alkenyl, $(C_2-C_6)$alkynyl, $(C_1-C_4)$alkylamino-$(C_1-C_4)$alkyl or phenyl, phenoxy, phenylcarbonyl or one of the last-mentioned 3 radicals which is substituted by one or more radicals selected from the group consisting of halogen, $(C_1-C_4)$alkyl and $(C_1-C_4)$alkoxy, $Y^1$ is a direct bond or $CH_2$, $(Y^2)_m$ is a divalent radical of the formula —$CH_2$—, —$CH(CH_3)$—, —$C(CH_3)_2$—, —$CH_2CH_2$—, —$CH(CH_3)$—$CH_2$—, —$CH(CH_3)$—$CH(CH_3)$—, —$CH(CH_3)CH(CH_3)$—, —$CH(C_6H_5)$—$CH_2$—, —$CH_2CH(C_6H_5)$— or —$CH(CH_3)$—$CH(C_6H_5)$—, $Y^3$ is a direct bond or a divalent radical of the formula $CH_2$, —$CH(CH_3)$—, —$C(CH_3)_2$—, $CH(OH)$, —O—, —S—, CO, $SO_2$, NH, $N(CH_3)$, $N(C_2H_5)$, $N(n-C_3H_7)$, $N(i-C_3H_7)$, $N(n-C_4H_9)$, $N(i-C_4H_9)$, $N(s-C_4H_9)$, $N(t-C_4H_9)$, $N(C_6H_5)$ or $N(CH_2C_6H_5)$ and n is 0, 1, 2 or 3.

5. A compound of the formula (I) or a salt thereof as claimed in claim 1, wherein $R^1$, $R^2$ independently of one another are hydrogen or $(C_1-C_4)$alkyl or $R^1$ and $R^2$ together with the nitrogen atom of the group $NR^1R^2$ are a saturated heterocyclic radical having 3 to 6 ring atoms and 1 hetero ring atom selected from the group consisting of N, O and S, or the heterocyclic radical being selected from the group consisting of piperazinyl and morpholinyl, $R^3$ is $(C_1-C_8)$alkyl, cyano-$(C_1-C_4)$alkyl, $(C_1-C_4)$haloalkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, $(C_3-C_9)$cycloalkyl-$(C_1-C_4)$alkyl, saturated heterocyclyl-$(C_1-C_4)$alkyl, the cyclic groups in the last-mentioned 4 radicals being unsubstituted or substituted by one or more radicals selected from the group consisting of $(C_1-C_4)$alkyl and halogen, or phenyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_1)$alkyl, phenoxy-$(C_1-C_4)$alkyl, phenyl-$(C_1-C_4)$alkyl, heterocyclyl, or one of the last-mentioned 7 radicals which is substituted in the acyclic moiety or in the cyclic moiety by one or more radicals selected from the group consisting of halogen, nitro, $(C_1-C_4)$alkyl, $(C_1-C_4)$alkoxy, $(C_1-C_4)$haloalkyl, $(C_1-C_4)$alkylcarbonyl, $(C_1-C_4)$alkoxycarbonyl and $(C_1-C_4)$alkoxy, the heterocyclyl in the radicals having in each case 3 to 7 ring atoms and 1 hetero ring atom selected from the group consisting of N, O and S, or heterocyclyl being selected from the group consisting of pyrimidinyl, pyridazinyl, pyrazinyl, thiazolyl, oxazolyl, pyrazolyl, imidazolyl, piperazinyl, dioxolanyl and morpholinyl, $R^4$ is hydrogen, amino, formyl, aminocarbonyl, $(C_1-C_4)$alkyl, cyano-$(C_1-C_4)$alkyl, $(C_1-C_4)$alkylamino, $(C_1-C_4)$alkoxy-$(C_1-C_4)$alkyl, $(C_2-C_6)$alkenyl, halo $(C_2-C_6)$alkenyl, $(C_2-C_6)$alkynyl, phenyl, $(C_1-C_4)$alkylcarbonyl, $(C_1-C_4)$alkoxycarbonyl, phenoxy-$(C_1-C_4)$alkyl, phenyl-$(C_1-C_4)$alkyl, or one of the last-mentioned 5 radicals which is substituted in the acyclic moiety or in the cyclic moiety by one or more radicals selected from the group consisting of halogen, $(C_1-C_4)$alkyl and $(C_1-C_4)$alkoxy, $R^5$ is hydrogen or $(C_1-C_4)$alkyl, $R^6$ if n is 1, and the radicals $R^6$ in each case independently of one another, if n is greater than 1, is, or are, halogen, $(C_1-C_4)$alkyl, $(C_1-C_4)$alkoxy or halo$(C_1-C_4)$alkyl, $Y^1$ is a direct bond or $CH_2$, $(Y^2)_m$ is a divalent radical of the formula $CH_2$ or $CH_2CH_2$, $Y^3$ is a direct bond, $CH_2$, —O— or —S—, and n is 0, 1, 2 or 3.

6. A herbicidal or plant-growth-regulating composition, which comprises one or more compounds of the formula (I) or a salt thereof as claimed in claim 1 and formulation auxiliaries conventionally used in crop protection.

7. A method for controlling harmful plants or for regulating the growth of plants, which comprises applying an effective amount of one or more compounds of the formula (I) or a salt thereof as claimed in claim 1 to the plants, seeds of the plants or the area under cultivation.

* * * * *